United States Patent
Levi et al.

(10) Patent No.: US 9,833,309 B2
(45) Date of Patent: Dec. 5, 2017

(54) THIN FILM VASCULAR STENT AND BIOCOMPATIBLE SURFACE TREATMENT

(75) Inventors: Daniel S. Levi, Pacific Palisades, CA (US); Gregory P. Carman, Los Angeles, CA (US); Youngjae Chun, Los Angeles, CA (US); Fernando Vinuela, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1312 days.

(21) Appl. No.: 13/224,103

(22) Filed: Sep. 1, 2011

(65) Prior Publication Data

US 2014/0249614 A1    Sep. 4, 2014

Related U.S. Application Data

(63) Continuation of application No. PCT/US2010/026430, filed on Mar. 5, 2010.
(Continued)

(51) Int. Cl.
*A61F 2/07* (2013.01)
*A61B 17/12* (2006.01)
(Continued)

(52) U.S. Cl.
CPC .......... *A61F 2/07* (2013.01); *A61B 17/12022* (2013.01); *A61B 17/12118* (2013.01);
(Continued)

(58) Field of Classification Search
CPC .... A61F 2/07; A61F 2/95; A61F 2/954; A61F 2/82; A61F 2/92; A61F 2/93; A61F 2/962;
(Continued)

(56) References Cited

U.S. PATENT DOCUMENTS 3,798,061 A * 3/1974 Yamazaki ............... 427/583
5,383,926 A * 1/1995 Lock ....................... A61F 2/92
606/198
(Continued)

FOREIGN PATENT DOCUMENTS

WO    WO 2006/034114 A2    3/2006
WO    WO 2007/051179 A2    5/2007
(Continued)

OTHER PUBLICATIONS

Korean Intellectual Property Office (KIPO), International Search Report and Written Opinion dated Nov. 26, 2010,(including claims searched), related PCT Application No. PCT/US2010/026430, pp. 1-23.
(Continued)

*Primary Examiner* — Jocelin Tanner
(74) *Attorney, Agent, or Firm* — Morgan, Lewis & Bockius LLP

(57) ABSTRACT

A vascular implant, comprising a sheet comprising thin film nickel titanium (NiTi), wherein the sheet has at least one super-hydrophilic surface having a water contact angle of less than approximately 5 degrees. The sheet is configured to have a compacted form having a first internal diameter and a deployed form having a second internal diameter larger than the first internal diameter. The sheet may be delivered into a blood vessel in the compacted form and expanded to its deployed form at a treatment location within the blood vessel, wherein the stent is configured to expand onto an internal surface of the blood vessel and exert a radial force on said internal surface.

59 Claims, 30 Drawing Sheets

Related U.S. Application Data

(60) Provisional application No. 61/158,200, filed on Mar. 6, 2009, provisional application No. 61/158,221, filed on Mar. 6, 2009.

(51) Int. Cl.
  *A61L 31/02* (2006.01)
  *A61F 2/95* (2013.01)
  *A61F 2/91* (2013.01)
  *A61F 2/92* (2013.01)
  *A61F 2/82* (2013.01)

(52) U.S. Cl.
  CPC .............. *A61F 2/95* (2013.01); *A61L 31/022* (2013.01); *A61B 2017/1205* (2013.01); *A61F 2/91* (2013.01); *A61F 2/92* (2013.01); *A61F 2002/077* (2013.01); *A61F 2002/823* (2013.01); *A61L 2400/18* (2013.01)

(58) Field of Classification Search
  CPC .... A61F 2/966; A61F 2/91; A61F 2/90; A61F 2002/072; A61F 2002/9534; A61F 2002/9522; A61F 2002/823; A61F 2002/825; A61L 33/0011; A61L 33/0017; A61L 33/0029; A61L 33/0076; A61L 33/022; A61L 2420/00; A61L 2420/02; B05D 1/18; C23C 8/02; C23C 8/10; C23C 30/00; C23C 30/005; C23C 4/105; C23C 28/00; C23C 28/30; C23C 28/3455; C23C 4/02; C23C 4/18; C23C 28/023; B22F 1/0088; Y02T 50/67; F01D 5/288; B32B 15/01
  See application file for complete search history.

(56) References Cited

U.S. PATENT DOCUMENTS

| | | | | |
|---|---|---|---|---|
| 5,578,075 | A * | 11/1996 | Dayton ............... | A61F 2/92 604/104 |
| 6,096,175 | A * | 8/2000 | Roth ............... | 204/192.15 |
| 6,120,535 | A * | 9/2000 | McDonald et al. ......... | 623/1.39 |
| 6,120,917 | A * | 9/2000 | Eda ............... | 428/846.1 |
| 6,245,102 | B1 | 6/2001 | Jayaraman | |
| 6,435,660 | B1 * | 8/2002 | Ozaki ............... | B41J 2/14129 347/45 |
| 6,540,849 | B2 | 4/2003 | DiCarlo et al. | |
| 6,790,372 | B2 | 9/2004 | Roy et al. | |
| 7,704,274 | B2 | 4/2010 | Boyle et al. | |
| 8,313,523 | B2 | 11/2012 | Banas et al. | |
| 8,690,938 | B2 | 4/2014 | Tenne | |
| 2001/0039449 | A1 * | 11/2001 | Johnson et al. ............. | 623/1.19 |
| 2002/0165600 | A1 | 11/2002 | Banas et al. | |
| 2003/0060782 | A1 | 3/2003 | Bose et al. | |
| 2003/0100945 | A1 | 5/2003 | Yodfat et al. | |
| 2003/0132193 | A1 * | 7/2003 | Okamoto ............... | 216/13 |
| 2004/0113542 | A1 * | 6/2004 | Hsiao ............... | H01L 51/5253 313/504 |
| 2004/0169007 | A1 * | 9/2004 | Sander et al. ............... | 216/33 |
| 2005/0033418 | A1 | 2/2005 | Banas et al. | |
| 2005/0186241 | A1 | 8/2005 | Boyle et al. | |
| 2005/0283220 | A1 | 12/2005 | Gobran et al. | |
| 2006/0128563 | A1 * | 6/2006 | Vogl ............... | B01J 35/004 502/350 |
| 2006/0142845 | A1 * | 6/2006 | Molaei et al. ............... | 623/1.22 |
| 2006/0259131 | A1 * | 11/2006 | Molaei et al. ............... | 623/1.44 |
| 2007/0059763 | A1 * | 3/2007 | Okano ............... | G01N 33/5061 435/7.1 |
| 2007/0073374 | A1 * | 3/2007 | Anderl ............... | A61F 2/91 623/1.2 |
| 2007/0225800 | A1 * | 9/2007 | Sahatjian et al. ............ | 623/1.42 |
| 2008/0004691 | A1 * | 1/2008 | Weber ............... | A61F 2/91 623/1.16 |
| 2008/0203012 | A1 * | 8/2008 | Yeager et al. ........... | 210/500.36 |
| 2009/0093871 | A1 | 4/2009 | Rea et al. | |
| 2009/0112306 | A1 * | 4/2009 | Bonsignore ............... | A61F 2/07 623/1.15 |
| 2010/0298515 | A1 | 11/2010 | Marchand et al. | |
| 2014/0249620 | A1 | 9/2014 | Carman et al. | |

FOREIGN PATENT DOCUMENTS

| | | |
|---|---|---|
| WO | WO 2008/151204 A1 | 12/2008 |
| WO | WO 2010/102254 A2 | 9/2010 |

OTHER PUBLICATIONS

Notice of Grant, Patent Certificate, EP10749417.1, dated Jul. 20, 2016, 1 pg.
Augsburger, L. et al., "Effect of flow diverter porosity on intraaneurysmal blood flow," Clinical Neuroradiology, Mar. 12, 2009, 11 pgs.
Carman, Office Action, U.S. Appl. No. 13/668,241, dated Jan. 2, 2015, 10 pgs.
Carman, Final Office Action, U.S. Appl. No. 13/668,241, dated May 1, 2015, 11 pgs.
Carman, Office Action, U.S. Appl. No. 13/668,241, dated Nov. 3, 2015, 12 pgs.
Carman, Final Office Action, U.S. Appl. No. 13/668,241, dated Mar. 29, 2016, 11 pgs.
Carman, Office Action, U.S. Appl. No. 13/668,241, dated Jul. 26, 2016, 10 pgs.
Chu, C.L. et al., "Surface oxidation of NiTi shape memory alloy in a boiling acqous solution containing hydrogen peroxide," Materials Science and Engineering, Oct. 4, 2005, 6 pgs.
Chun, Y.J. et al., "Novel micro-patterning processes for thin film NiTi vascular devices," Smart Mater, Struct., 19 (2010), Aug. 25, 2010, 3 pgs.
International Search Report and Written Opinion, PCT/US2011/037988, dated Feb. 9, 2012, 20 pgs.
Sergueeva et al., Structure and properties of amorphous and nanocrystalline NiTi prepared by severe plastic deformation and annealing; Materials Science and Engineering A339; 2003; pp. 159-165.
Tateshima et al., "Alteration of intraaneurysmal hemodynamics by placement of a self-expandable stent," J Neurosurg, vol. 11, Jul. 2009, 6 pgs.
The Regents of the University of California, Communication Pursuant to Article 94(3) EPC, EP10749417.1, dated Jul. 3, 2015, 4 pgs.
The Regents of the University of California, Decision to Grant, EP10749417.1, dated Jun. 23, 2016, 1 pg.
The Regents of the University of California, Office Action, app No. CA2,753,853, dated Jan. 29, 2016, 6 pgs.
The Regents of the University of California, Notice of Allowance, CA2,753,853, dated Oct. 18, 2016, 1 pg.

* cited by examiner

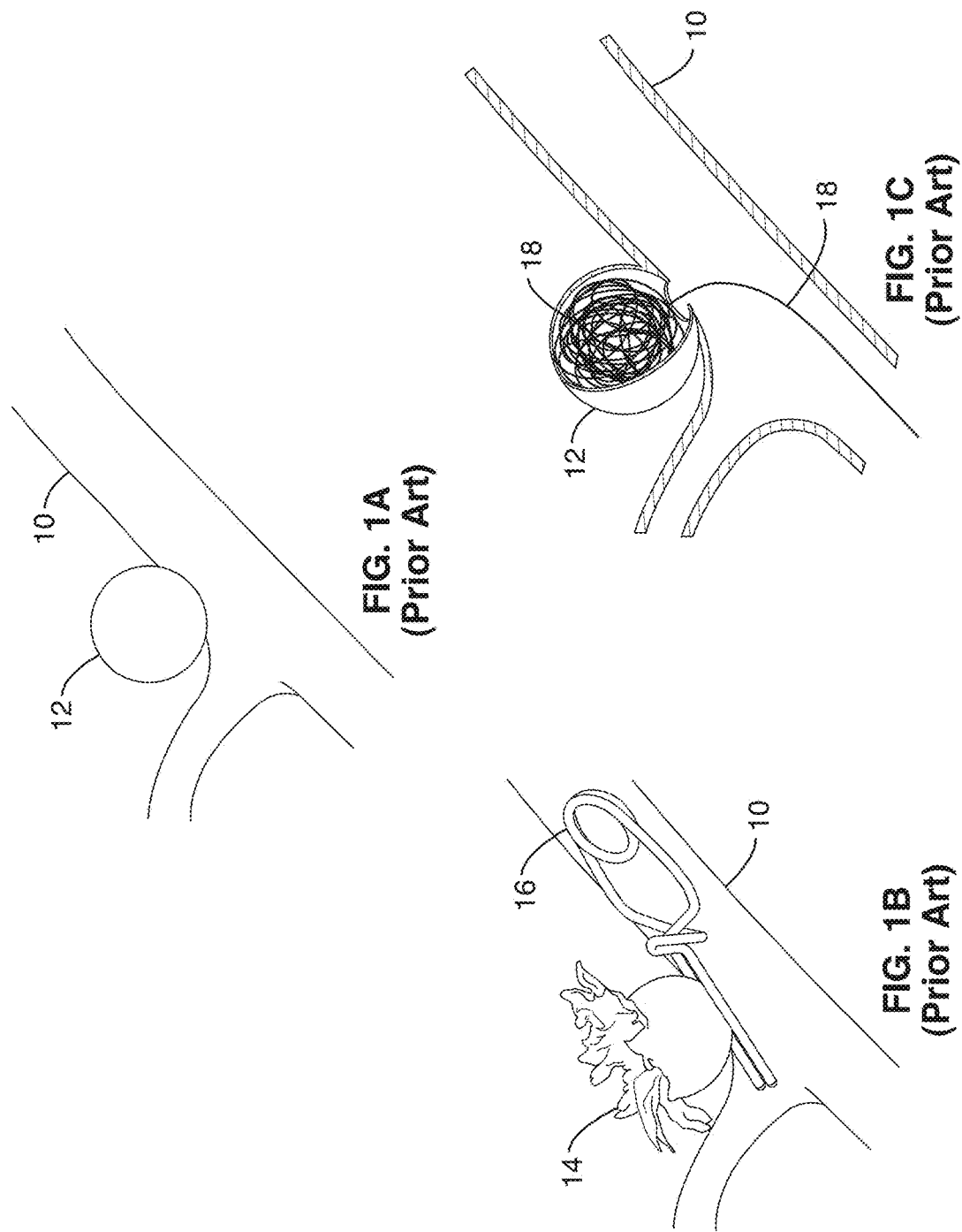

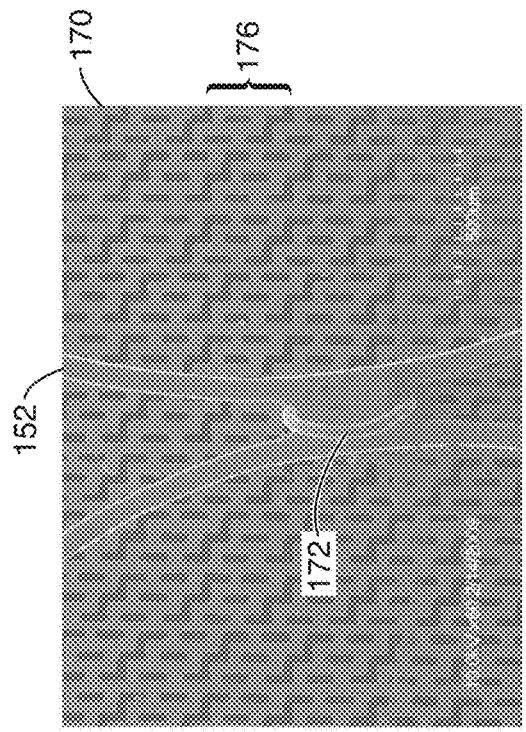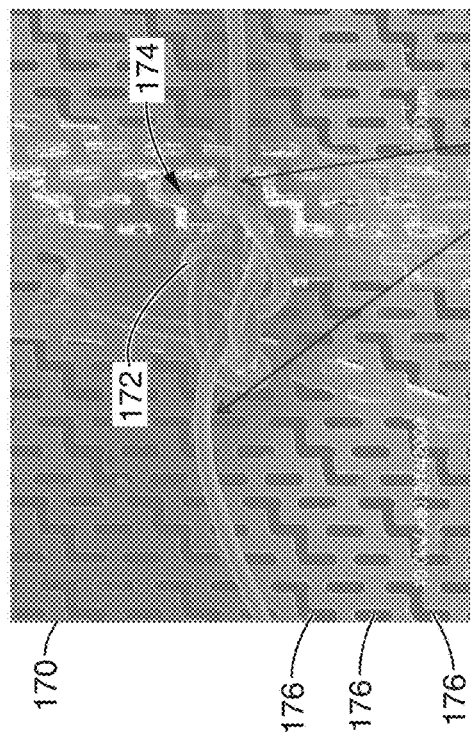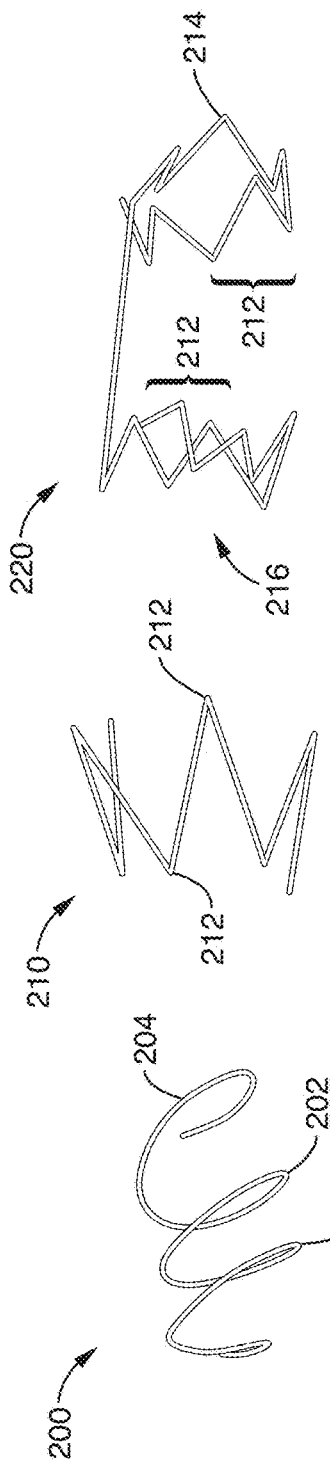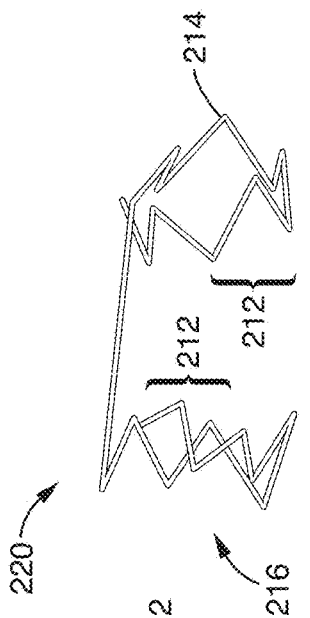
FIG. 13A
FIG. 13B
FIG. 14A
FIG. 14B
FIG. 14C

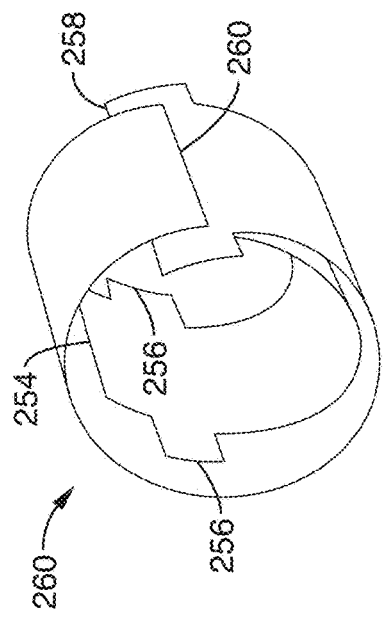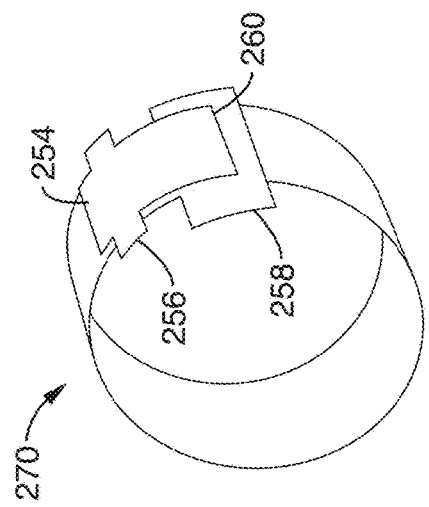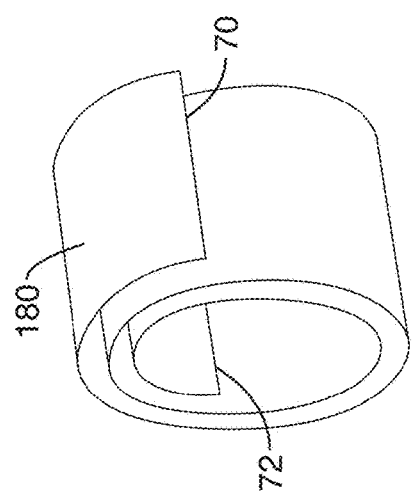

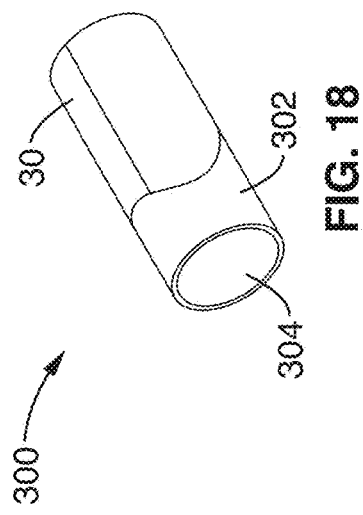
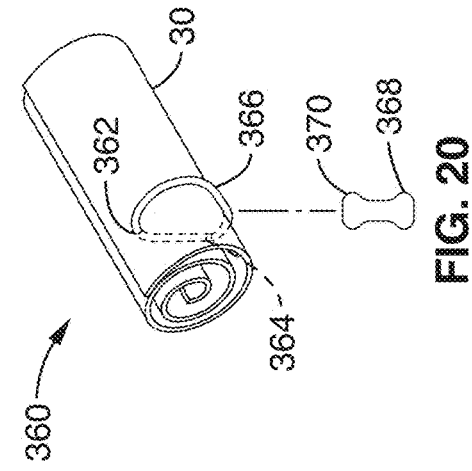
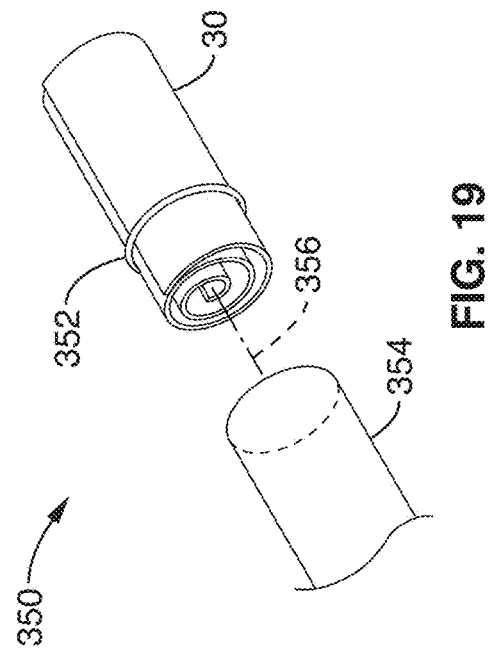

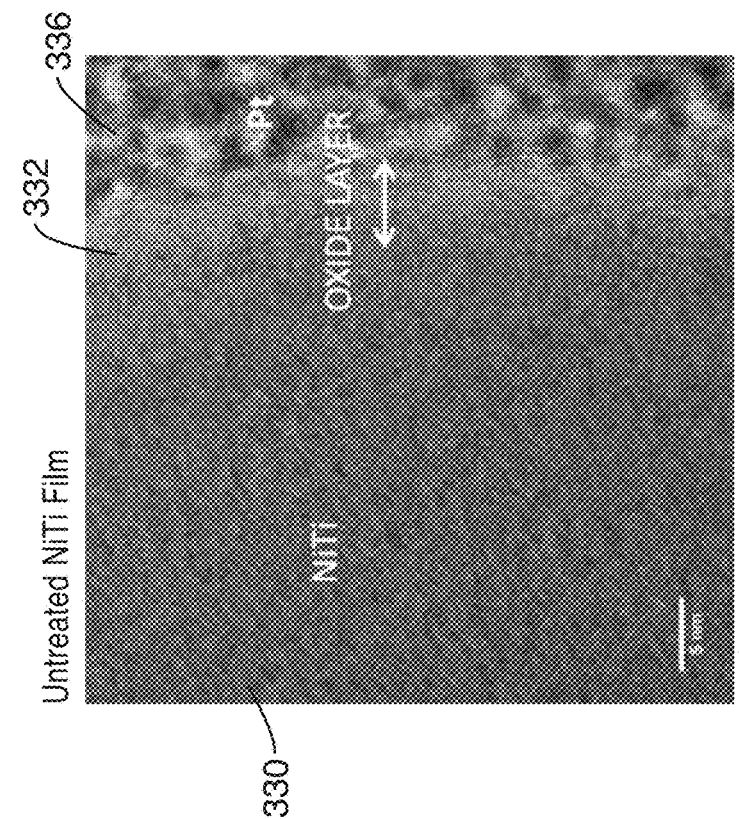
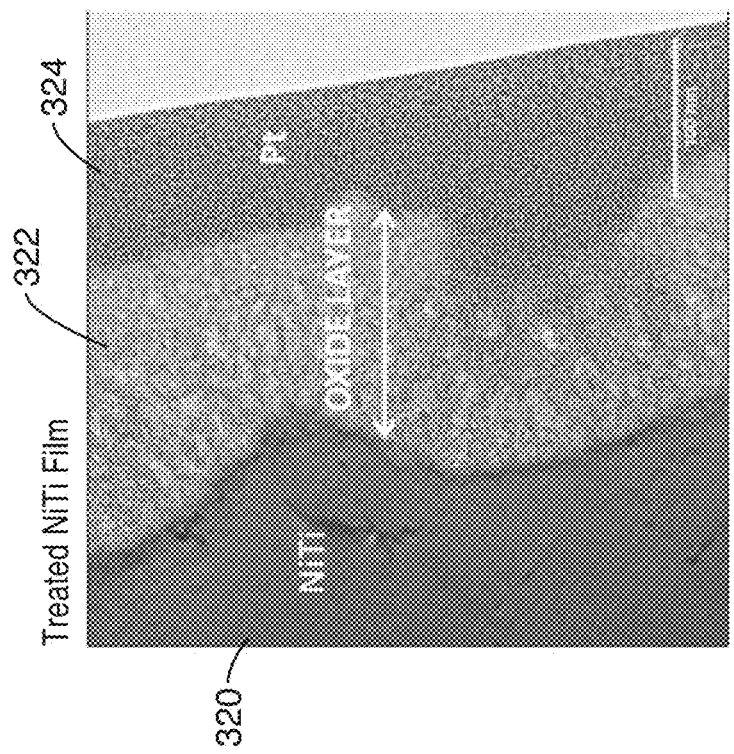
FIG. 30A
FIG. 30B

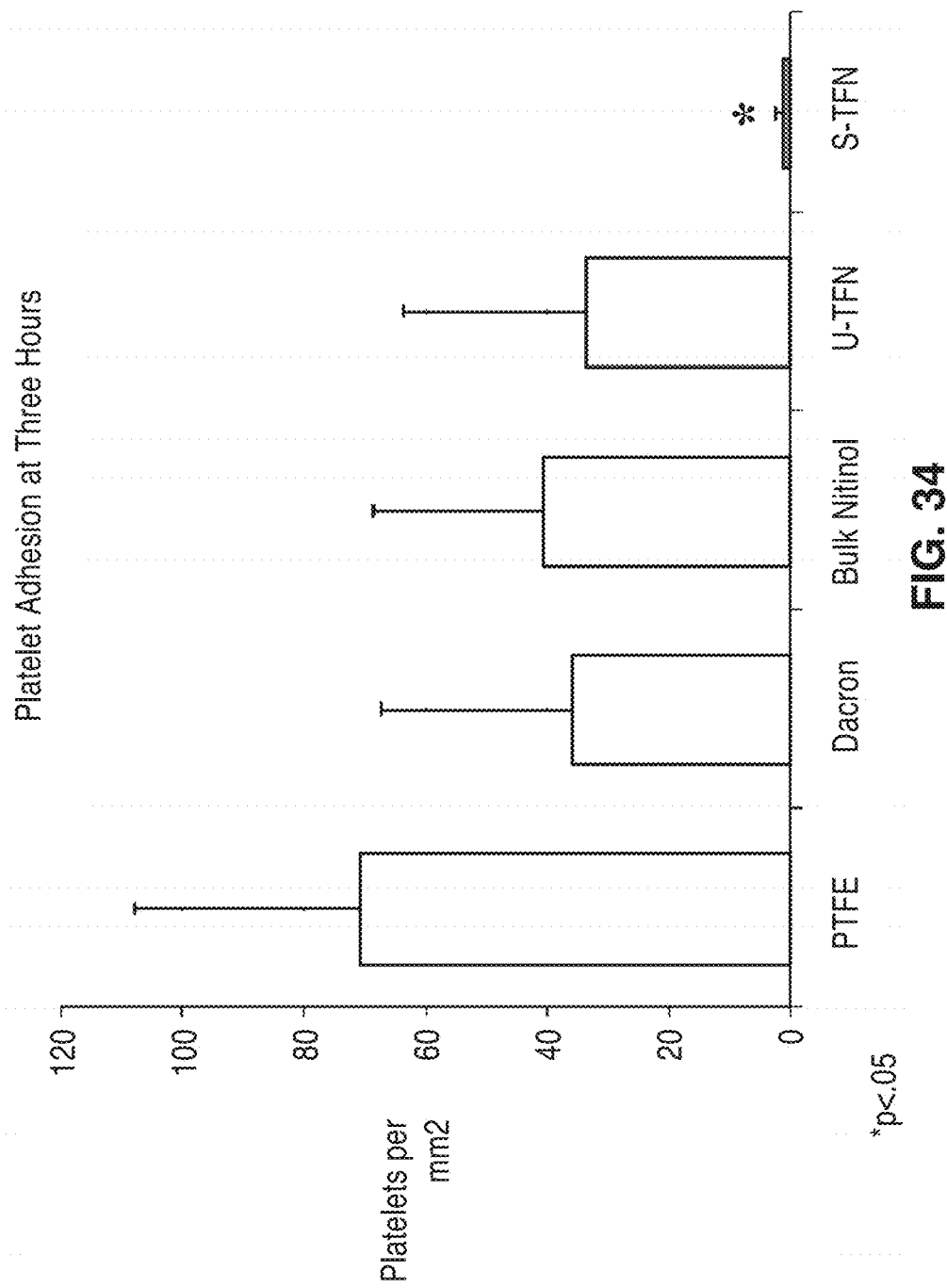

THIN FILM VASCULAR STENT AND BIOCOMPATIBLE SURFACE TREATMENT

CROSS-REFERENCE TO RELATED APPLICATIONS

This application a 35 U.S.C. §111(a) continuation of PCT international application number PCT/US2010/026430 filed on Mar. 5, 2010, incorporated herein by reference in its entirety, which is a nonprovisional of U.S. provisional patent application Ser. No. 61/158,200, filed on Mar. 6, 2009, incorporated herein by reference in its entirety, and from U.S. provisional patent application Ser. No. 61/158,221, filed on Mar. 6, 2009, incorporated herein by reference in its entirety. Priority is claimed to each of the foregoing applications.

The above-referenced PCT international application was published as PCT International Publication No. WO 2010/102254 published on Sep. 10, 2010 and republished on Jan. 20, 2011, and is incorporated herein by reference in its entirety.

STATEMENT REGARDING FEDERALLY SPONSORED RESEARCH OR DEVELOPMENT

This invention was made with Government support under Grant No. W81XWH-07-1-0672 awarded by the U.S. Army, Medical Research and Materiel Command. The Government has certain rights in this invention.

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to implantable devices, and more particularly to an implantable medical device, and surface treatments for the same, for treating diseases and disorders of blood vessels.

2. Description of Related Art

Aneurysms can occur in the neurovasculature. An aneurysm is a spherical out-pouching of blood vessels formed from a localized weakness in the wall of an artery. FIG. 1A illustrates an exemplary cerebral aneurysm 12, which is a localized dilation of the wall of a blood vessel 10. Aneurysms can occasionally rupture and cause a life threatening hemorrhage. Postmortem examinations indicate that 10–12 million people have brain aneurysms in the United States and 20–50% will potentially rupture. Aneurysm rupture carries a high rate of morbidity and mortality. Current approaches to prevent aneurysms from rupturing include both surgical and transcatheter methods.

A surgical approach to treat aneurysms by "clipping" the aneurysm neck has been used for a select group of aneurysms. In the open craniotomy or surgical clipping approach shown in FIG. 1B, a surgical clip 16 is used to isolate the aneurysm 14 from the artery 10, and thereby prevent uncontrolled bleeding upon rupture of the aneurysm 14. However, this procedure requires a craniotomy (an opening in the skull) and is not always applicable depending on the aneurysm size, location and complexity.

More recently, transcatheter procedures to treat vascular aneurysms have been developed. In the endovascular coiling or coil embolization approach shown in FIG. 1C, a wire 18 is introduced through the artery 10 and made to coil inside and fill the aneurysm 12. The coiled wire induces formation of a clot in the aneurysm 12, thereby preventing uncontrolled bleeding upon rupture of the aneurysm.

Because the coil embolization technique is less invasive and more cost-effective than surgery, it has become the standard of care for most aneurysms. The coils pack the aneurysm sac 12 densely to limit blood flow in the aneurysm and produce more local thrombosis within the aneurysm.

While coils are beneficial, they can only be used for aneurysms with "necks" narrow enough to hold coils in the aneurysm.

However, certain aneurysms are difficult to treat with the current endovascular coiling or coil embolization approach of FIG. 1C. For example, wide neck aneurysms 20 shown in FIGS. 2A and 2B are dangerous and difficult to treat with endovascular coiling FIG. 2B.

To address this issue, a stent can be placed across the neck of a broad-neck aneurysm and coils placed into the aneurysm through the cells of the stent. This procedure is complicated (it involves two types of devices—a stent and multiple coils) and is limited by the physical size of the stent's delivery system.

The treatment of many disease processes relies on the ability to use a stent that can hold blood vessels open and provides a barrier to the passage of body fluids. Such a stent can also provide a circumferentially occlusive boundary between the stent and the vessel. For example, these stents are useful for re-establishing the integrity of aneurysmal vessels at risk for rupturing. The potential applications of such covered stents are wide-ranging and include the treatment of carotid and coronary artery disease, aortic and central nervous system vascular aneurysms, carotid artery or pulmonary artery stenoses, carotid artery atheromas, and even treatment of ruptured vessels or vessels at risk to rupture.

In the palliation of congenital heart disease, the appropriate stent would be useful for stenting the ductus arteriosus, coarctation of the aorta, or potentially in the treatment of pulmonary artery stenoses and in the stenting of pulmonary veins, an intervention often plagued by in-stent stenosis. Various materials have been used to cover stents, including silicone, polyurethane, and polytetrafluoroethylene. Examples of commercially available covered stents include the polytetrafluoroethylene (PTFE) covered JoStent made by JoMed, the iCAST stent made by Atrium Medical and the CP covered stent that is available from NuMed.

To date, the production of a highly flexible, durable, and thrombus-resistant stent material has not been achieved for all applications. Covered stents generally have a thick covering, making the profile of the stent unacceptably large for certain applications, such as implantation in small and/or tortuous blood vessels, such as found in the vasculature supplying the central nervous system. Accordingly, there are no commercially available covered stents that are low profile enough and flexible enough for use in the neurovasculature.

Thrombotic complications involving indwelling medical devices placed in the vascular are a challenge and burden to patients and our healthcare system as a whole. With the development of new devices as well as concomitant increase in the number of endovascular cases performed, there exists a need to identify ways to limit thrombotic complications associated with vascular devices. The successful treatment of many diseases via endovascular techniques is particularly limited by clot formation on indwelling devices (such as stents). This is especially true in small vessels.

In the 1950s, it was shown that native blood vessels carry a net negative charge. This led to the concept that hydrophilic or electronegative surfaces can provide thromboresistance. When vessel wall injury occurs, the native blood vessel charge at the area of injury turns positive, preferentially attracting negatively charged platelets to the site of injury. While charge is important for thromboresistance, it is not the only factor: surface roughness and binding of other blood products such as fibrinogen or leukocytes have been shown to activate the clotting cascade. Therefore, the ideal covering for indwelling devices would be both hydrophilic and very smooth. Because molecules such as fibrinogen have both hydrophilic and hydrophobic binding sites, both in vitro and in vivo studies are essential in demonstrating that a specific super hydrophilic surface treatment indeed provides a thrombotic advantage to an S-TFN covered stent.

Other surface treatments have been explored for vascular grafts to improve hydrophilicity. These include treatments such as polyethylene glycol and polyethylene oxide which have been shown to prevent platelet adhesion. However, these polymers bond poorly to grafts and have so far been relegated to laboratory science. In the case of ePTFE, the surface is electronegative, but hydrophobic, which has been hypothesized to cause thrombosis in low flow states.

It has been demonstrated that the degree of hydrophilicity, measured by surface wettability, is important in preventing platelet adhesion. While there is evidence that hydrophilic surfaces reduce thrombogenecity, a successful approach that produces a super hydrophilic surface on metals currently used in vascular applications has been absent.

C L. Chu, C Y. Chung, and P K. Chu, "Surface oxidation of NiTi shape memory alloy in a boiling aqueous solution containing hydrogen peroxide," 2006, Materials Science and Engineering A, 417, pp. 104-109, recently examined that surface treatment of NiTi with 30% $H_2O_2$ in a boiling aqueous solution produce approximately 500 nm thick TiO2 eliminating most Ni atoms from the surface in bulk NiTi. This method has been applied to thin film NiTi, but the results did not provide a superhydrophilic surface, and suggest that a superhydrohilic surface was not possible based on their methods. Chu et al. was primarily directed to releasing Ni atoms.

Accordingly, an object of the present invention is a stent having both a low profile and flexibility for use in the neurovasculature.

Another object is a stent having a material and surface treatment for generating a super hydrophilic surface to prevent platelet adhesion. At least some of these objectives will be met in the description below.

BRIEF SUMMARY OF THE INVENTION

An aspect of the invention is a vascular implant, comprising: a sheet comprising thin film nickel titanium (NiTi), wherein the sheet comprises at least one super-hydrophilic surface. In a preferred embodiment, the super-hydrophilic surface has a water contact angle of less than approximately 5 degrees, and is configured to deter platelet adhesion at a rate of less than 3 parts per $mm^2$ when subjected to platelet rich plasma for 3 or more hours.

In another embodiment, the hydrophilic surface is fabricated by a method comprising immersion of the thin film in a hydrogen peroxide solution.

In another embodiment, the method further includes passivation of the thin film in a nitric acid solution prior to immersion of the thin film in a hydrogen peroxide solution. Such passivation may follow immersion of the thin film in a buffered oxide etchant to eliminate the native oxide layer prior to passivation of the thin film. Furthermore, the method may include immersion of the thin film in a cleaning pretreatment dip comprising one or more of the following: acetone, methanol, and alcohol. Such cleaning pretreatment dip may comprise sequential dipping of acetone, methanol, and alcohol.

In another preferred embodiment, the thin film is generated using DC sputter deposition.

Preferably, the thin film has a thickness of less than about 30 µm. More preferably, the thin film comprises a stent configured to be installed adjacent a vascular aneurysm, wherein the thin film has a thickness ranging between about 4 µm and about 12 µm. In another case, the implant comprises a stent configured to be installed adjacent a cerebral aneurysm, wherein the thin film has a thickness ranging between about 6 µm and about 8 µm.

In another embodiment, the stent comprises a generally rectangular thin film sheet wrapped into a generally tubular shape having a longitudinal and radial direction, with two distal edges of the sheet defining two ends of the tubular shape, and two longitudinal edges of the sheet overlapping, wherein the sheet has a compacted form with a first internal diameter and a deployed form with a second internal diameter larger than the first internal diameter.

In one mode of the current embodiment, the stent is configured to be delivered into a blood vessel in the compacted form and expanded to its deployed form at a treatment location within the blood vessel such that it expands onto an internal surface of the blood vessel and exerts a radial force on the internal surface.

In another embodiment, the treatment location is an aneurysm, and the stent is configured to deploy at the aneurysm to cover at least a portion of the aneurysm.

In yet another embodiment, the stent comprises a truss comprising one or more members configured to be disposed in a compressed form when constrained inside a catheter; wherein the truss is configured to automatically expand at the treatment site when not constrained inside said catheter; wherein the thin film sheet is disposed over the truss covers the truss in the compacted from; and wherein the thin film sheet is configured to expand with expansion of said truss.

Another aspect is a method for generating a super hydrophilic layer on the surface of a vascular implant, comprising: fabricating a sheet comprising thin film nickel titanium (NiTi); and immersing the thin film in a hydrogen peroxide solution to generate at least one hydrophilic surface on the thin film.

In one embodiment, the hydrophilic surface comprises a super-hydrophilic surface having a water contact angle of less than approximately 5 degrees, and wherein the super-hydrophilic surface is configured to deter platelet adhesion at a rate of less than 3 parts per $mm^2$ when subjected to platelet rich plasma for 3 or more hours.

In another embodiment, the method includes: immersing the thin film in a cleaning pretreatment dip comprising one or more of the following: acetone, methanol, and alcohol, immersing the thin film in a buffered oxide etchant to eliminate the native oxide layer prior to passivation of the thin film, and passivating the thin film in a nitric acid solution prior to immersing the film in the hydrogen peroxide solution.

In a preferred embodiment, the method further includes storing the thin film in a high-humidity environment to maintain the super-hydrophilic surface. For example, the environment comprises a container comprising deionized water.

Another aspect is a method of forming a hydrophilic thin film sheet of nickel titanium, comprising: generating a sheet of thin film nickel titanium; subjecting the sheet of thin film nickel titanium to a surface treatment to remove the native titanium dioxide layer; and generating a hydrophilic layer by immersion of the thin-film sheet in a concentration of $H_2O_2$. Ideally, the sheet is stored in a high-humidity environment prior to delivery within the body.

Another aspect is a hydrophilic thin film sheet of nickel titanium prepared by the process comprising the steps of: generating a sheet of thin film nickel titanium; subjecting the sheet of thin film nickel titanium to a surface treatment to remove the native titanium dioxide layer; and generating a hydrophilic layer by immersion of the thin-film sheet in a concentration of $H_2O_2$.

Another aspect is a system for treating a vascular condition, comprising: a sheet comprising thin film nickel titanium (NiTi); wherein the sheet comprises at least one super-hydrophilic surface; and means for storing the sheet in a high-humidity environment. In one embodiment, the means for storing the sheet in a high-humidity environment comprises a container configured to house the thin film and a humidifying element.

In another embodiment, the system includes a catheter configured to be delivered into a blood vessel, wherein the container is configured to house the catheter with the stent installed in a compacted form inside said catheter.

Another aspect is a vascular implant, comprising: a sheet comprising thin film nickel titanium (NiTi); the sheet having a compacted form having a first internal diameter and a deployed form having a second internal diameter larger than the first internal diameter; wherein the sheet is configured to be delivered into a blood vessel in the compacted form; wherein the stent is configured to expanded to its deployed form at a treatment location within the blood vessel; and wherein the stent is configured to expand onto an internal surface of the blood vessel and exert a radial force on said internal surface.

In one embodiment, the thin film comprises a stent configured to be installed at a treatment site associated with a vascular aneurysm, wherein the thin film has a thickness ranging between about 4 µm and about 12 µm.

In another embodiment, the implant comprises a stent configured to be installed at a treatment site associated with a cerebral aneurysm, wherein the thin film has a thickness ranging between about 6 µm and about 8 µm.

In another embodiment of the current aspect, sheet comprises at least one super-hydrophilic surface having a water contact angle of less than approximately 5 degrees.

In another embodiment, the sheet is configured such that the radial force is larger than a drag force imparted on said sheet from blood flow on said internal surface.

Another aspect is a method for treating a vascular condition, comprising: wrapping a sheet comprising thin film nickel titanium (NiTi) into a generally tubular shape having a longitudinal and radial direction; the sheet having a compacted form having a first internal diameter and a deployed form having a second internal diameter larger than the first internal diameter installing the sheet in the compacted form into a catheter; delivering the catheter to a treatment location inside the blood vessel; wherein the sheet is configured to be deployed out of the catheter and expanded to its deployed form at the treatment location; and wherein the sheet is configured to expand onto an internal surface of the blood vessel and exert a radial force on said internal surface.

In one embodiment, the radial force is larger than a drag force imparted on said sheet from blood flow on said internal surface. In another embodiment, the sheet comprises at least one super-hydrophilic surface, wherein the super-hydrophilic surface has a water contact angle of less than approximately 5 degrees.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 1A illustrates an external view of an artery with an aneurysm.

FIG. 1B illustrates an open craniotomy using surgical clipping of the aneurysm of FIG. 1A.

FIG. 1C illustrates a coil embolization approach for treating of the aneurysm of FIG. 1A.

Figure 12:
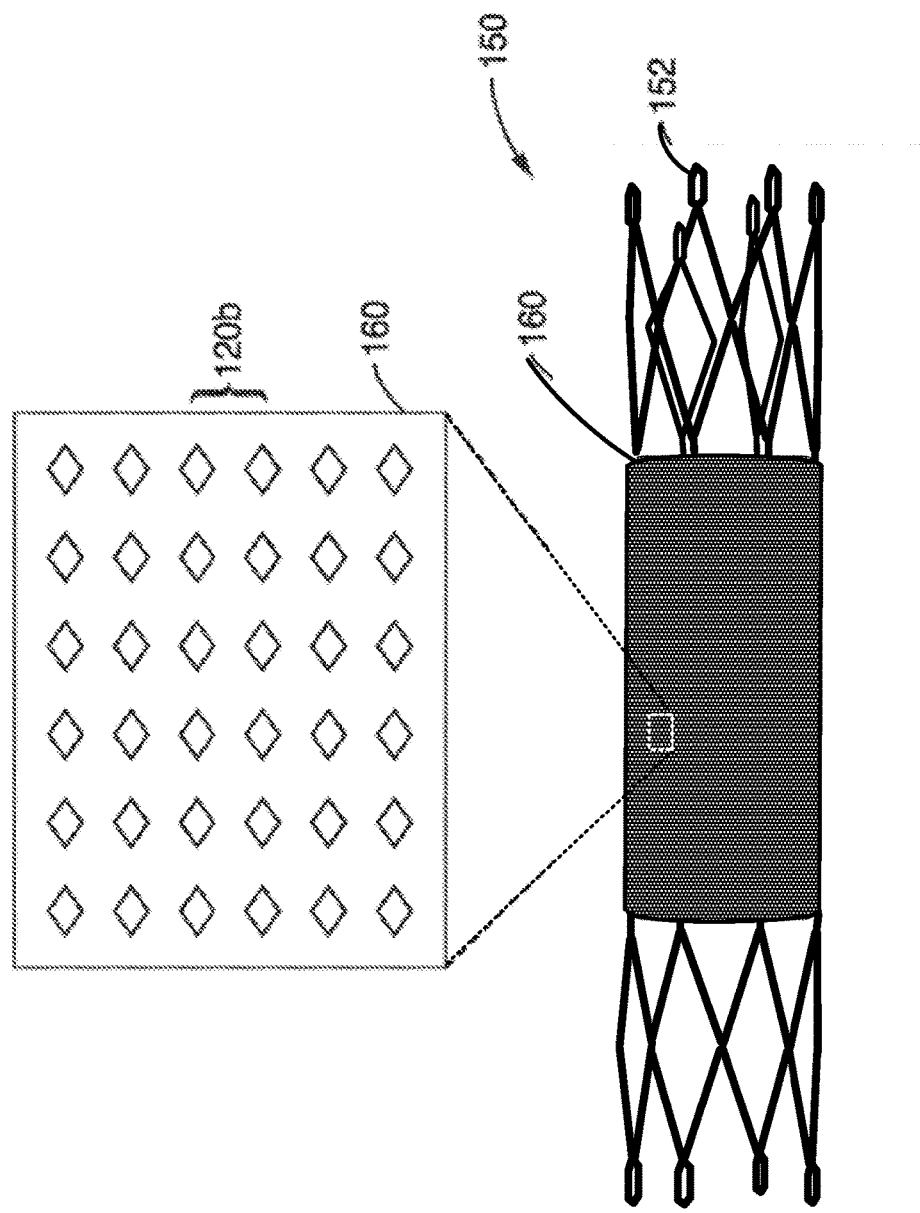

FIG. 12 comprises a thin film sheet fenestrated with a plurality of diamond shaped holes, and wrapped around a collapsible, truss-like stent in accordance with the present invention.

FIGS. 13A and 13B illustrate method for attaching a thin film having a plurality of fenestrations to a collapsible truss.

FIG. 14A shows a coil structure of a superelastic nitinol wire with a plurality of coils.

FIG. 14B shows a stent structure having a zigzag structure in accordance with the present invention.

FIG. 14C shows a stent structure having dual-zigzag structures in accordance with the present invention.

FIG. 15 illustrates a thin-film sheet having a length sufficient to form two coils.

FIG. 16 illustrates an embodiment of a thin-film stent according to the present invention having an inside roll tab-and-slot configuration.

FIG. 17 illustrates an embodiment of a thin-film stent according to the present invention having an outside roll tab-and-slot configuration.

FIG. 18 shows a system including a thin-film stent disposed around an inner tube.

FIG. 19 is a stent formed from a thin film sheet of memory metal held into a spiral form via a ring.

FIG. 20 shows an alternative system for retaining a thin film sheet of memory metal wrapped into a spiral in a compacted form using a loop.

Figure 21:
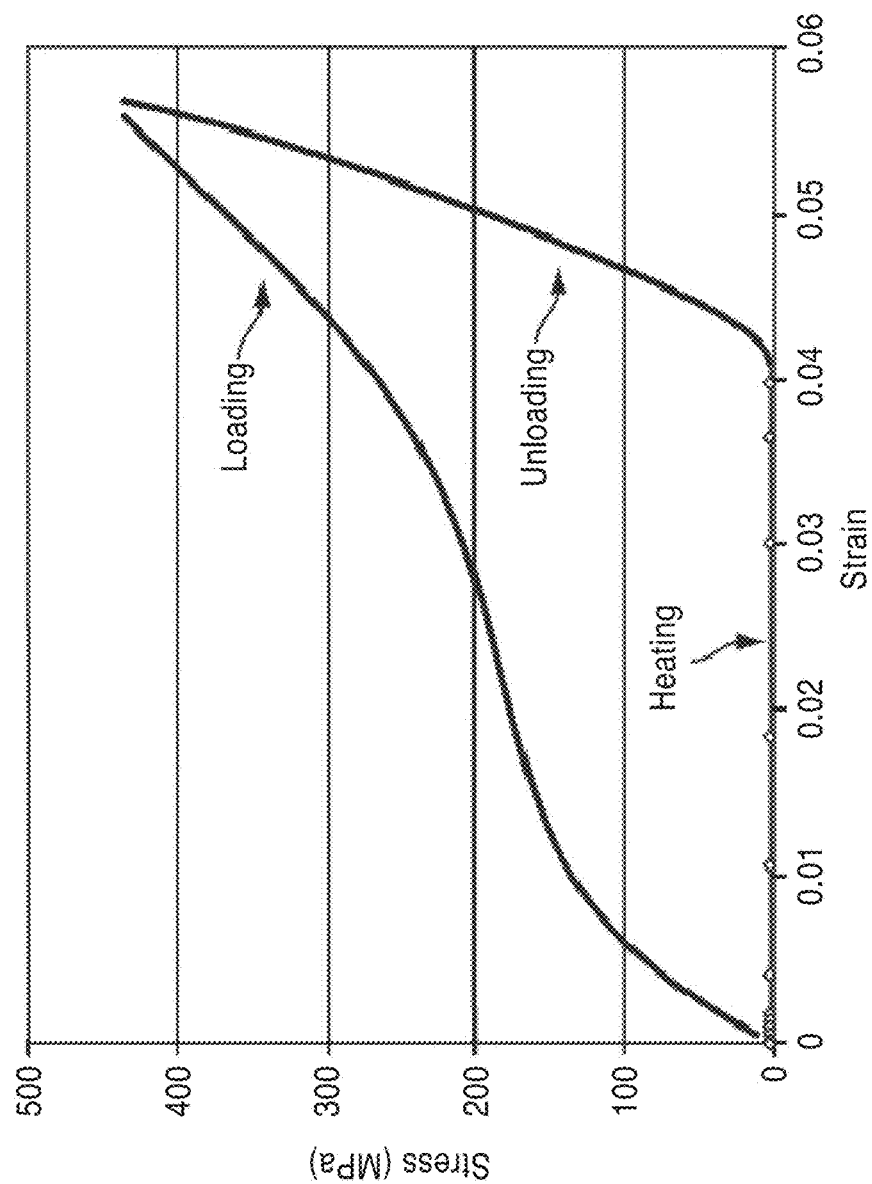

FIG. 21 illustrates a stress-strain curve quantifying the ductility and shape memory behavior of the thin film.

Figure 22B:
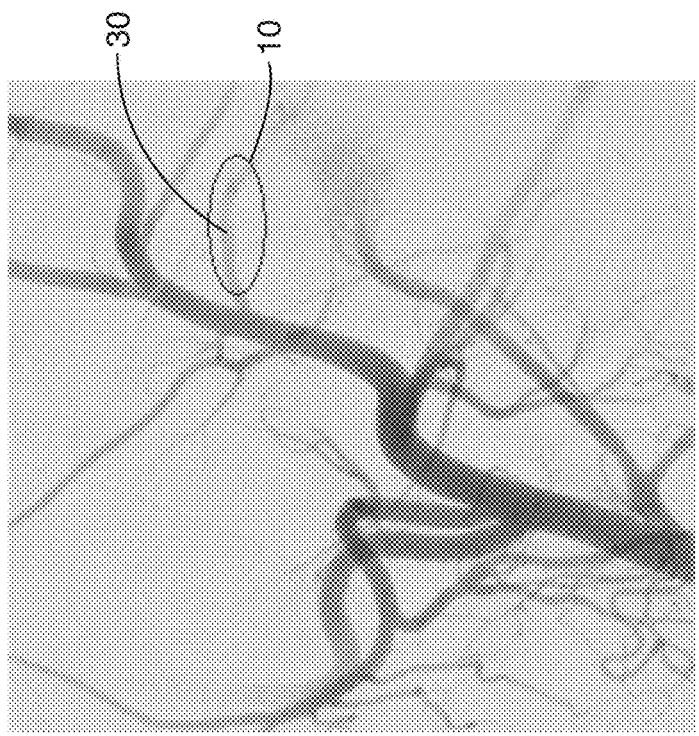
Figure 22A:
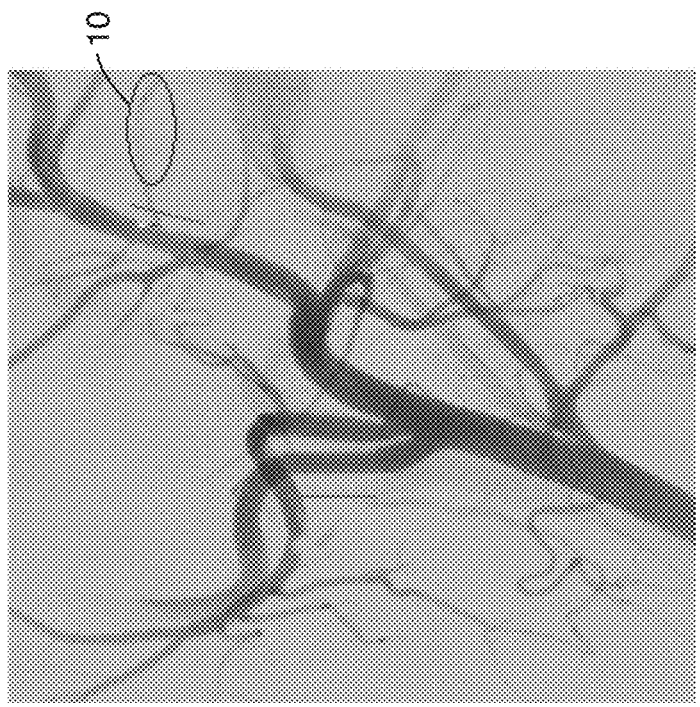

FIG. 22A shows an angiogram of swine cranial vasculature prior to thin film NiTi neurostent deployment.

FIG. 22B shows an angiogram of swine cranial vasculature taken after deployment of thin film NiTi neurostent of the present invention in the swine vasculature.

Figure 23:
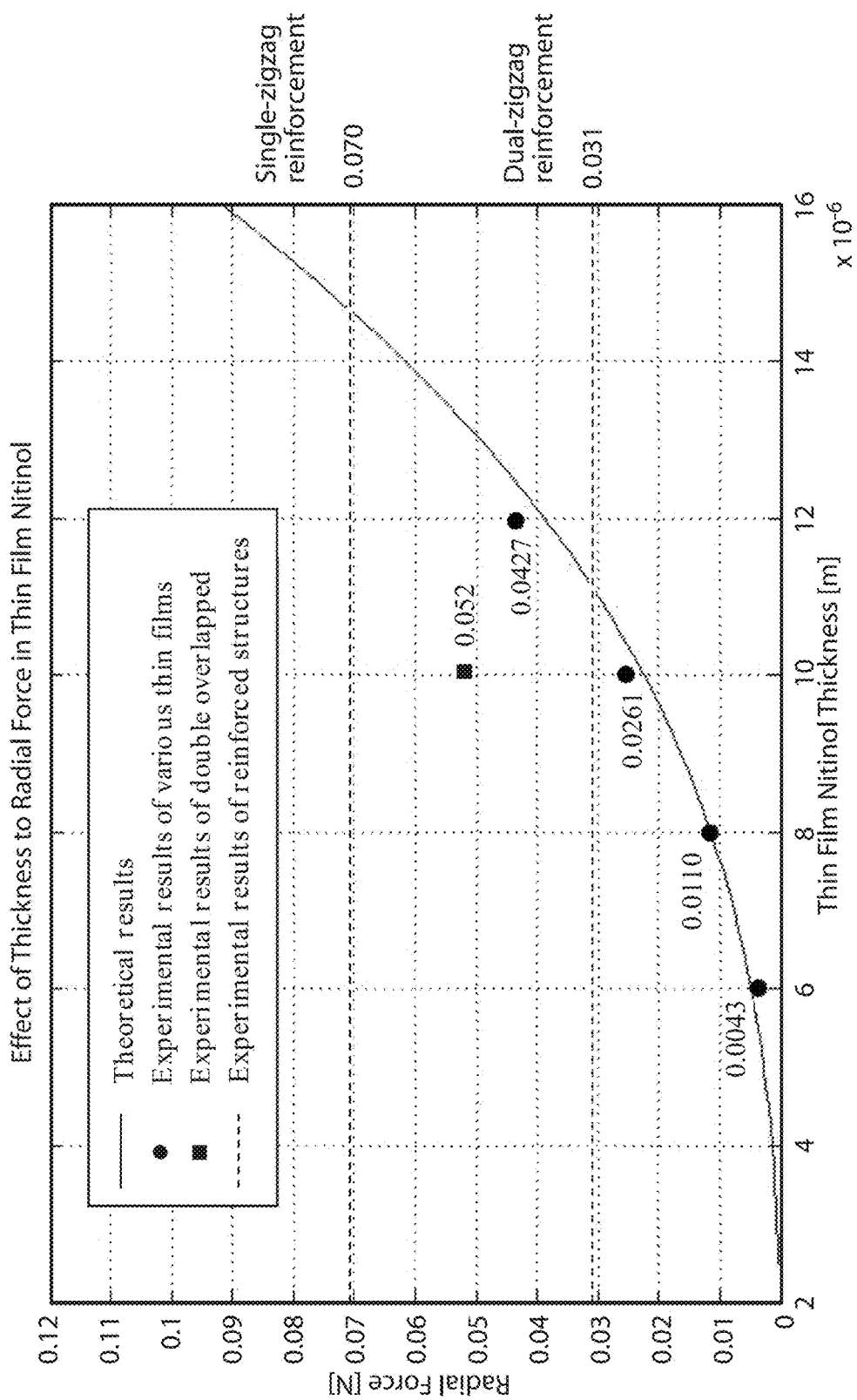

FIG. 23 shows a plot of the experimental (data points) and theoretical results (for radial force of different configurations and thicknesses of nitinol stents.

Figure 24:
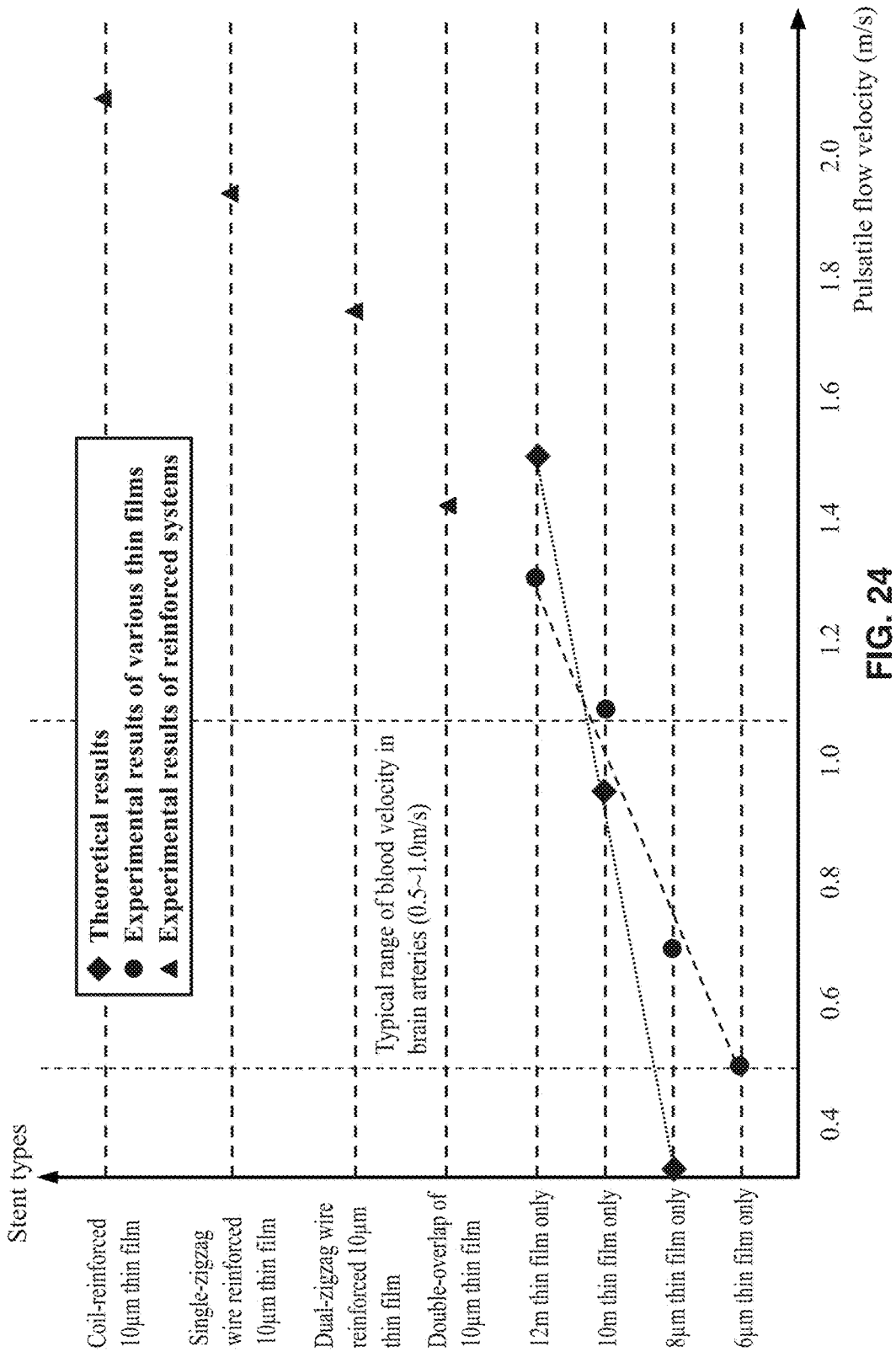

FIG. 24 provides experimental and theoretical results for the different stents studied in a flow loop.

Figure 25:
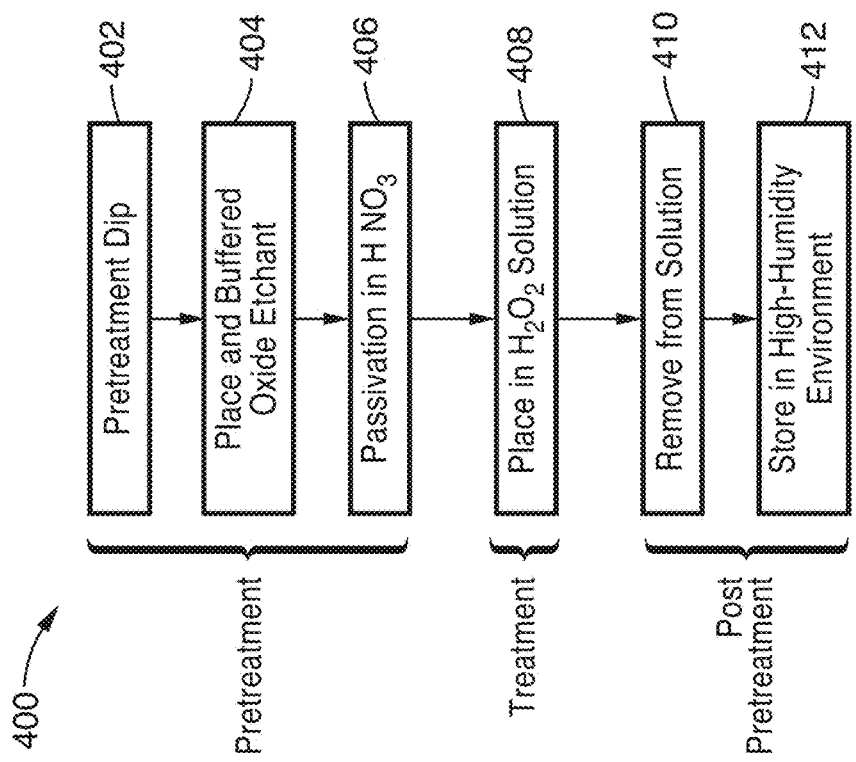

FIG. 25 is a flow diagram of an exemplary treatment method 400 for generating a super hydrophilic thin film NiTi stent in accordance with the present invention.

Figure 26:
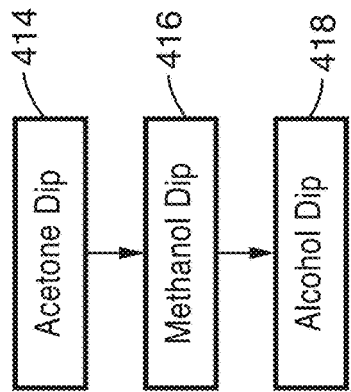

FIG. 26 is a flow diagram of a pretreatment dip used in the method of FIG. 25.

Figure 27A:
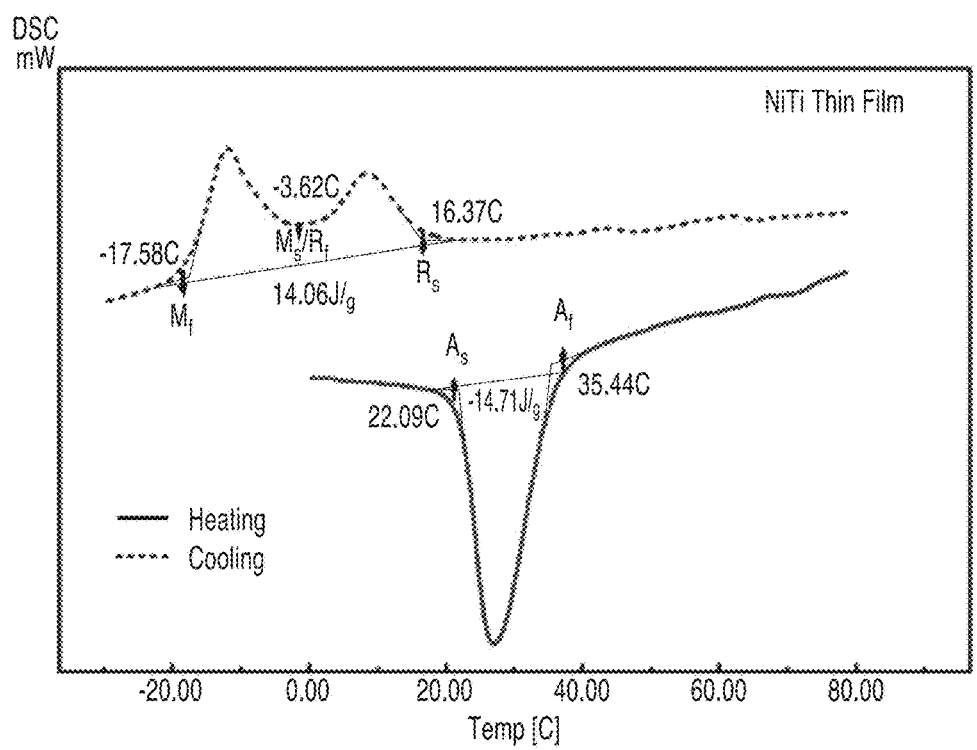

FIG. 27A illustrate a plot of DSC for thin film NiTi.

Figure 27B:
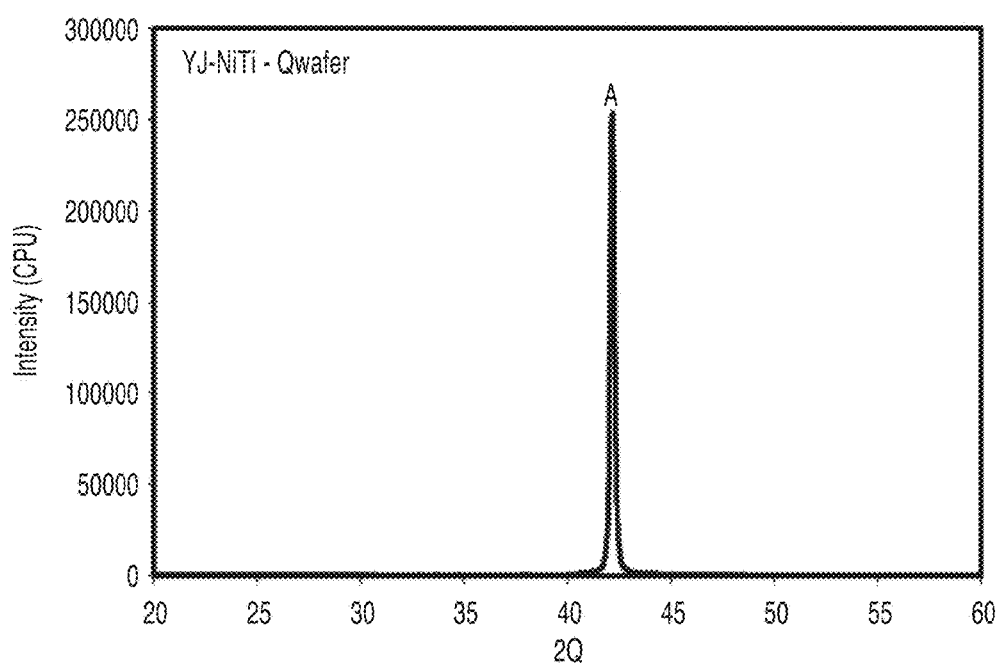

FIG. 27B shows the XRD pattern of thin film NiTi measured at room temperature.

Figure 28A:
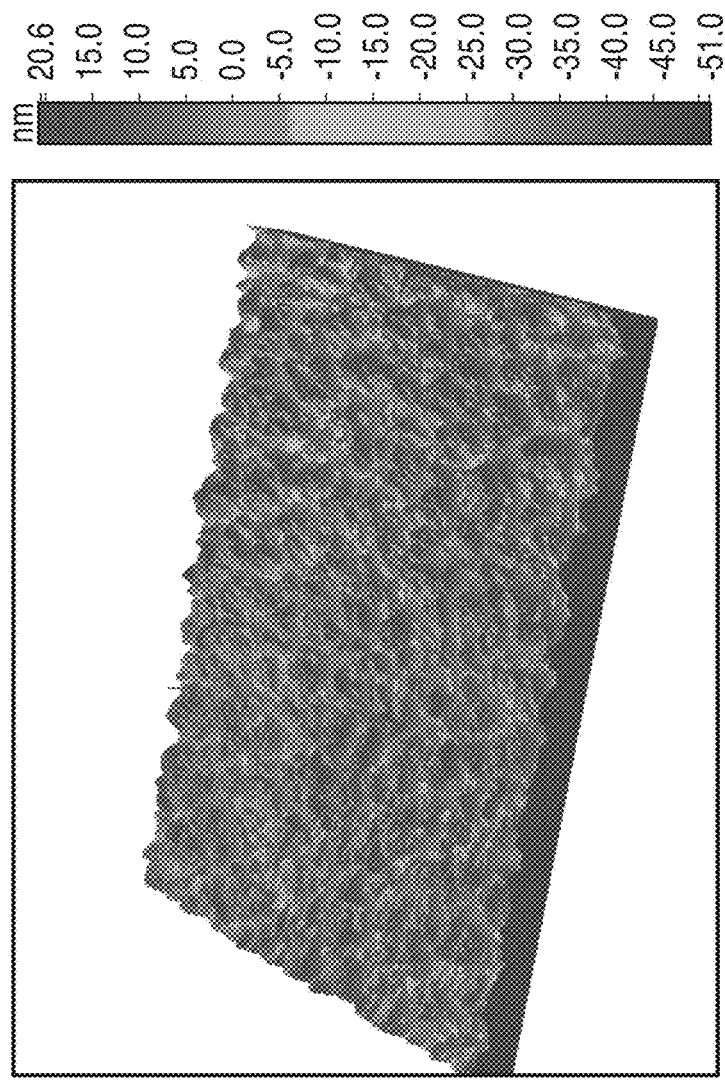

FIG. 28A shows 3D contour plot along with a line plot (FIG. 28B) of surface morphology of the Nitinol thin film in the B2 phase.

Figure 28B:
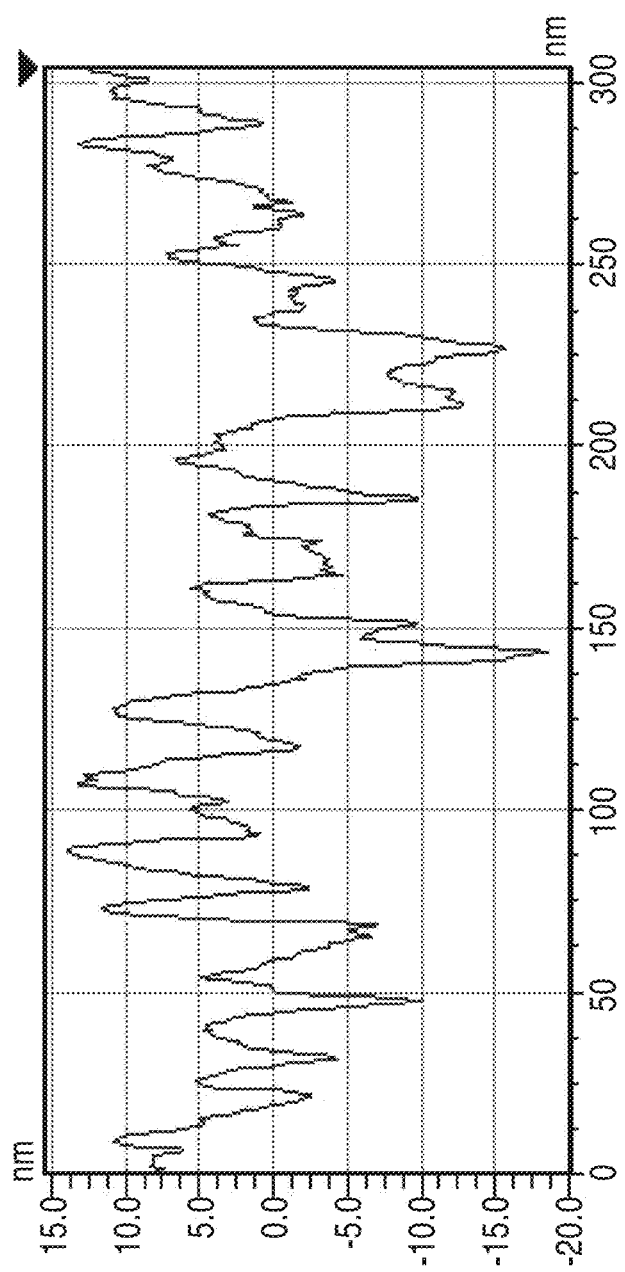

FIG. 28B shows more detail of the surface morphology of the thin-film sheet of FIG. 28A.

Figure 29:
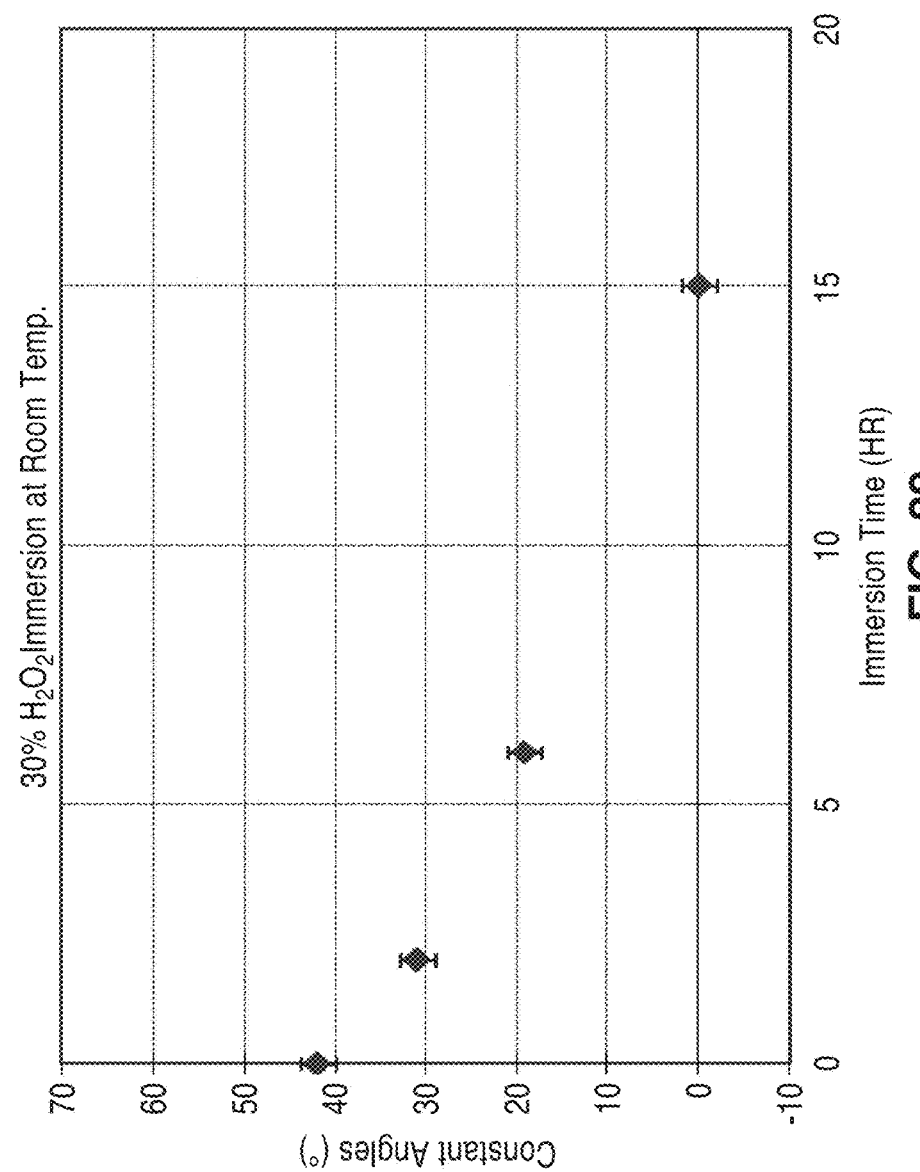

FIG. 29 is a plot showing the contact angle produced by hydrogen peroxide treatment (HPT) as a function immersion time in the $H_2O_2$ solution treatment step.

FIGS. 30A and 30B are TEM results between thin film NiTi treated in accordance with the present invention (FIG. 30A), and untreated NiTi (FIG. 30B)

Figure 31A:
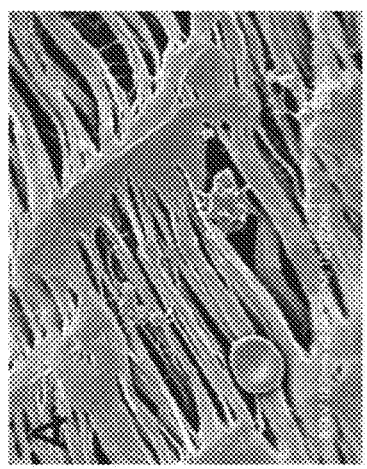
Figure 31B:
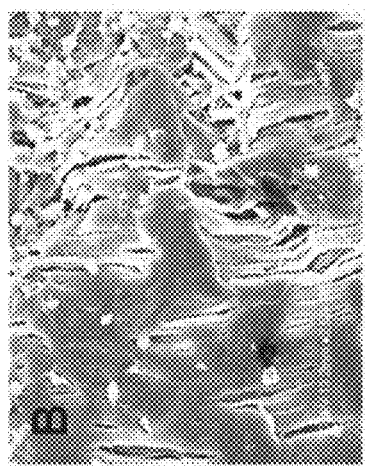
Figure 31C:
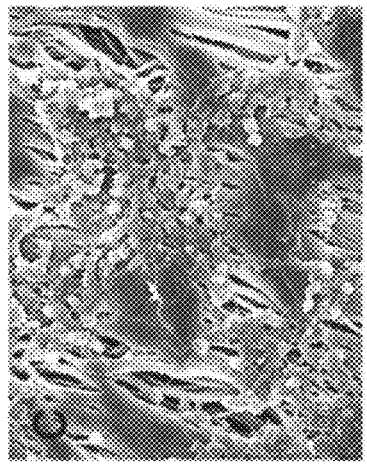

FIGS. 31A-C illustrate scanning electron micrograph images demonstrating increasing platelet adhesion on ePTFE after 30 minutes (FIG. 31A), 60 minutes (FIG. 31B) and 180 minutes (FIG. 31C) of contact with platelet rich plasma.

Figure 32A:
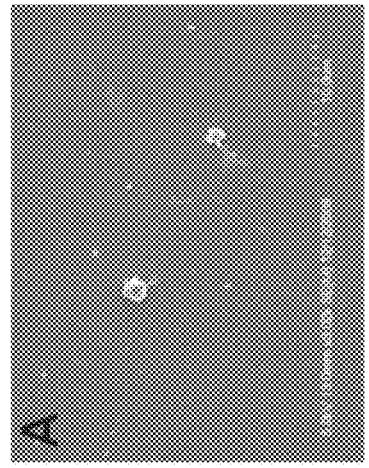
Figure 32B:
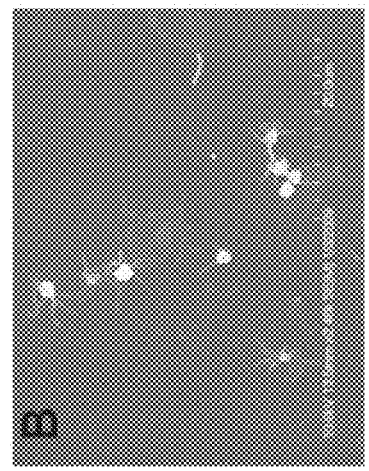
Figure 32C:
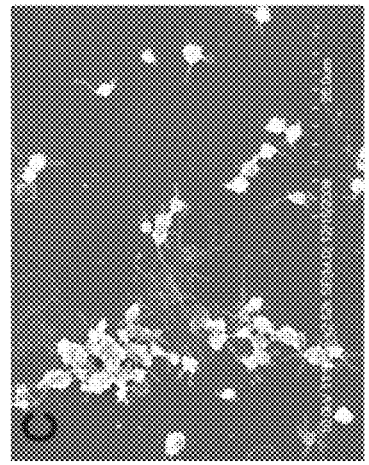

FIGS. 32A-C illustrate scanning electron micrograph images demonstrating increasing platelet adhesion on Untreated Thin Film Nitinol after 30 minutes (FIG. 32A), 60 minutes (FIG. 32B) and 180 minutes (FIG. 32C) of contact with platelet rich plasma.

Figure 33A:
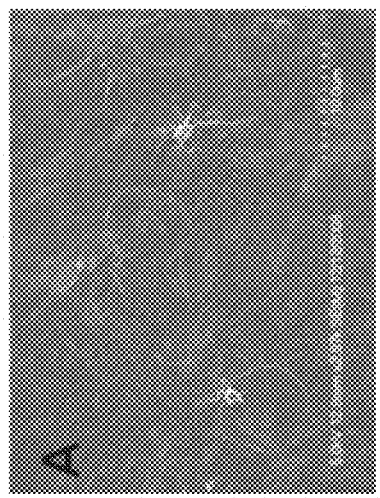
Figure 33B:
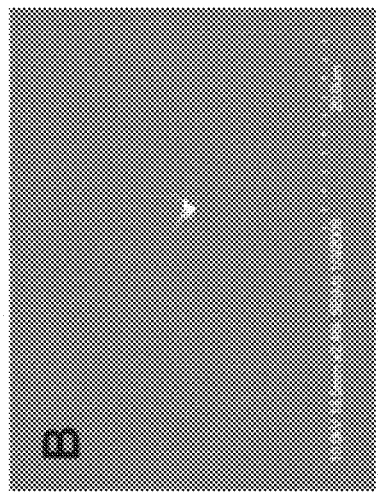
Figure 33C:
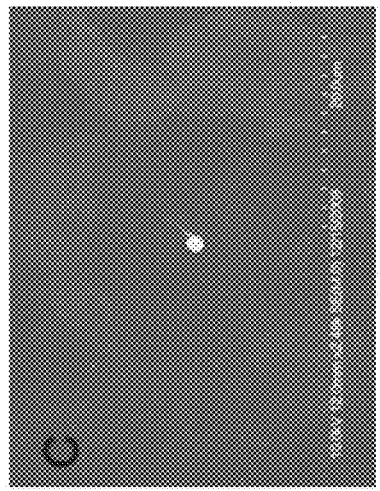

FIGS. 33A-C are scanning electron micrograph images of super hydrophilic thin film Nitinol of the present invention, demonstrating minimal platelet adhesion and no evidence of aggregation at 30 minutes (FIG. 33A), 60 minutes (FIG. 33B), and 180 minutes (FIG. 33C) after contact with platelet rich plasma.

FIG. 34 is a graph of platelet adhesion per $mm^2$ of surface area for various surfaces after 180 minutes of contact with platelet rich plasma. Platelet adhesion and aggregation on Dacron (n=3), ePTFE (n=3), bulk nitinol (n=3), U-TFN (n=3), and S-TFN (n=5) were quantified using a 180 minute time point as a marker.

Figure 35:
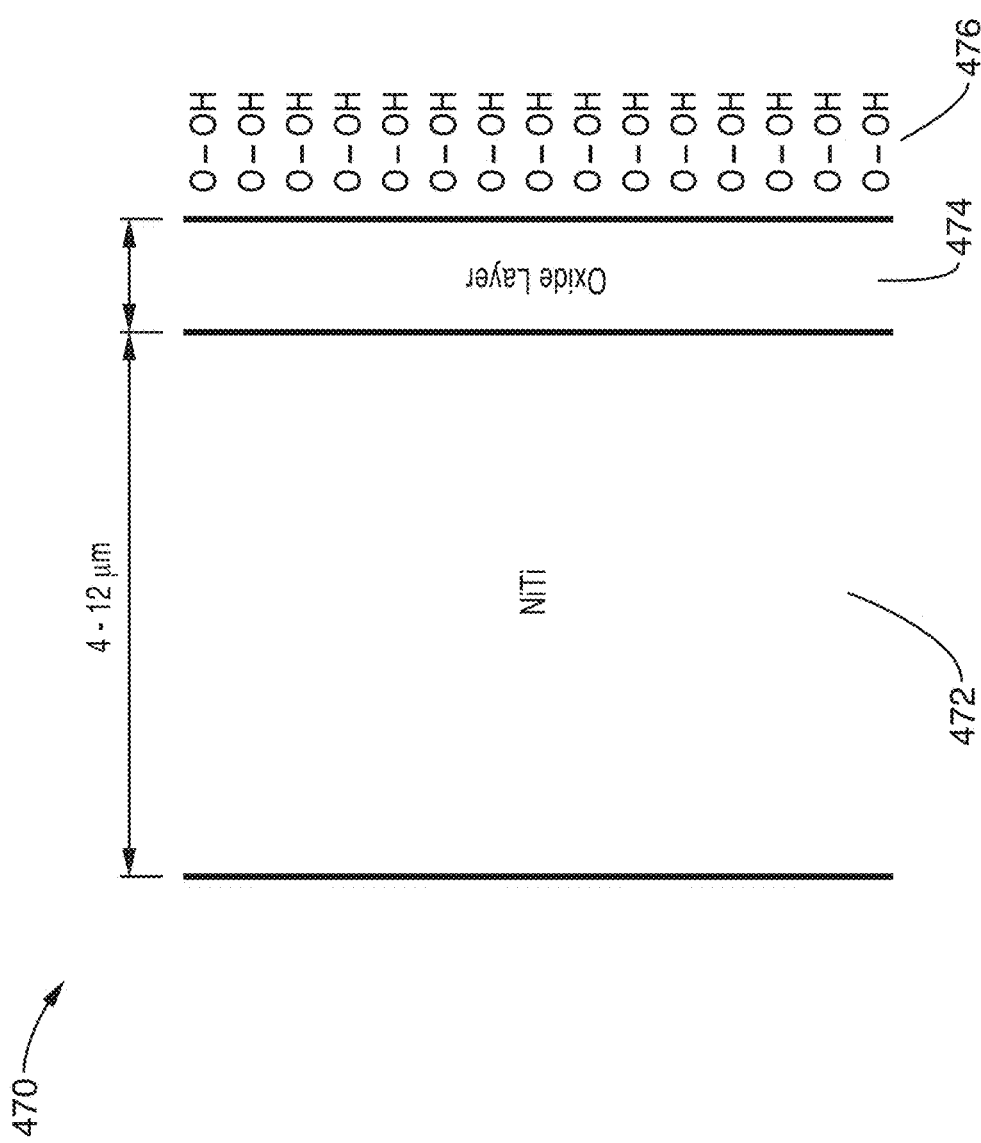

FIG. 35 is a schematic sectional view of the surface treated thin film Nitinol of the present invention.

Figure 36:
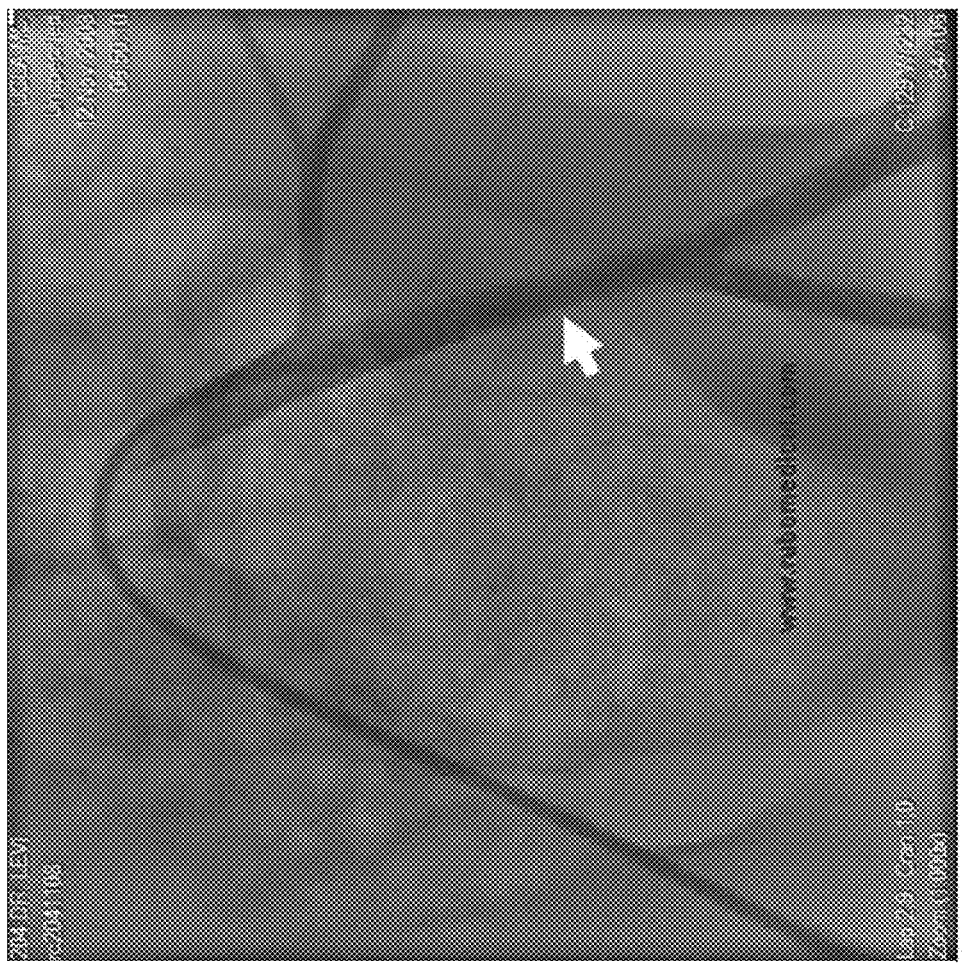

FIG. 36 illustrates an angiographic view of an artery with an implanted covered stent of the present invention.

Figure 37:
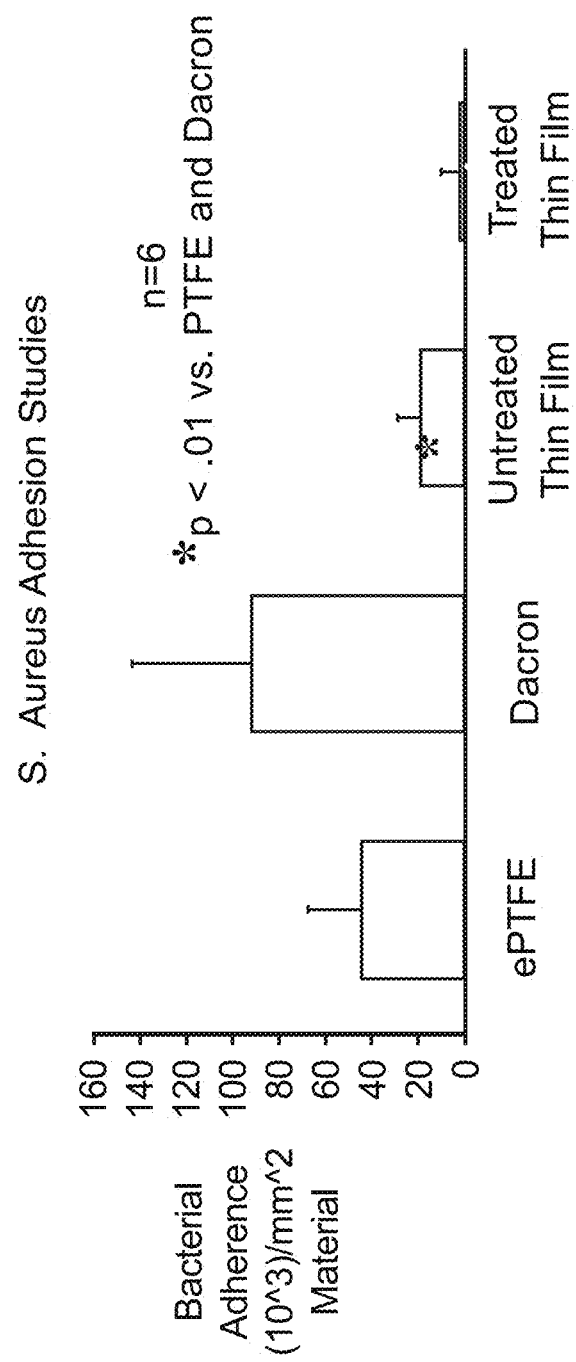

FIG. 37 illustrates results of an S. Aureus adhesion study on treated thin film Nitinol of the present invention as compared to ePTFE, Dacron, or untreated thin film Nitinol.

DETAILED DESCRIPTION OF THE INVENTION

Referring more specifically to the drawings, for illustrative purposes the present invention is embodied in the apparatus generally shown in FIG. 2C through FIG. 37. It will be appreciated that the apparatus may vary as to configuration and as to details of the parts, and that the method may vary as to the specific steps and sequence, without departing from the basic concepts as disclosed herein.

I. Thin Film Stent

Figure 2C:
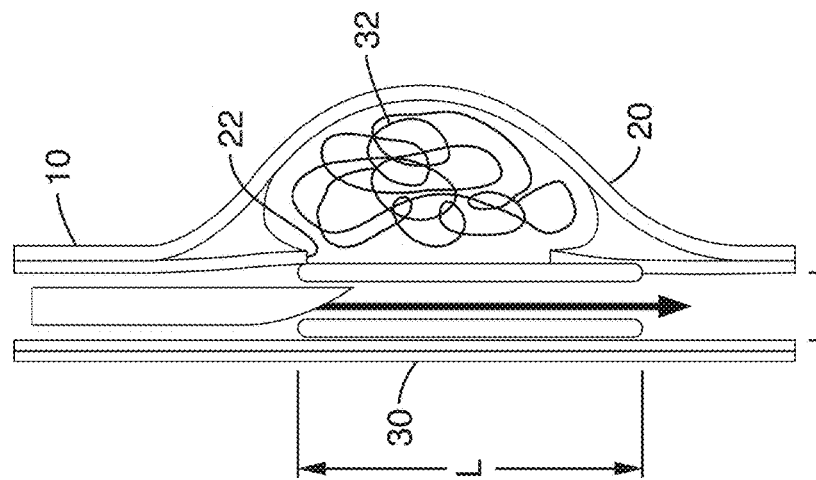
FIG. 2C illustrates an exemplary stent in accordance with the present invention for a wide-neck aneurysm.
Figure 2B:
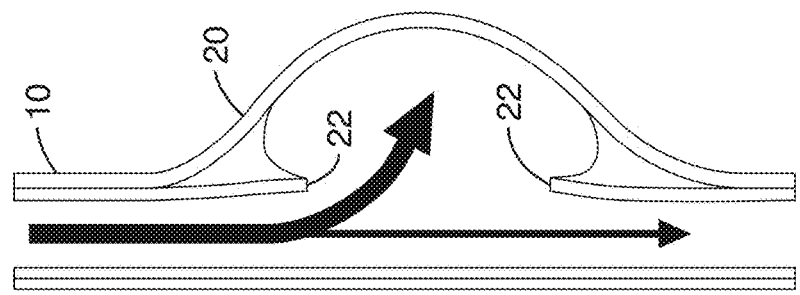
FIG. 2B illustrates an internal view of a wide neck aneurysm.
Figure 2A:
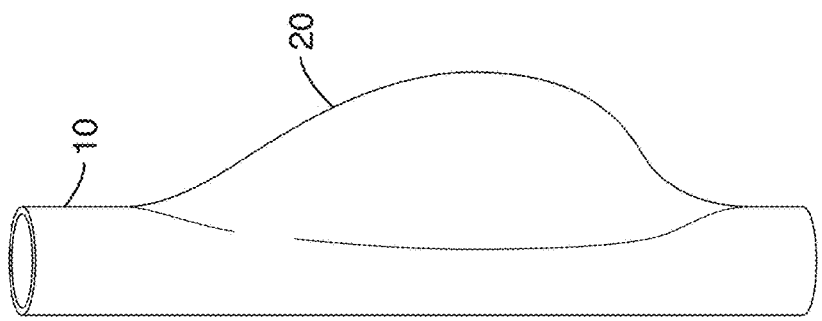
FIG. 2A illustrates an external view of a wide neck aneurysm.

FIG. 2C illustrates an exemplary stent 30 in accordance with the present invention for treating an aneurysm, such as a wide-neck aneurysm 20. As seen in FIG. 2C, the stent 30 is generally a cylindrical body having an expanded diameter D configured to contact the inner surface of lumen 10. The stent 30 has a length L configured to block the opening 22 of aneurysm 20 to form clot 32 within the aneurysm sac 20.

Figure 3:
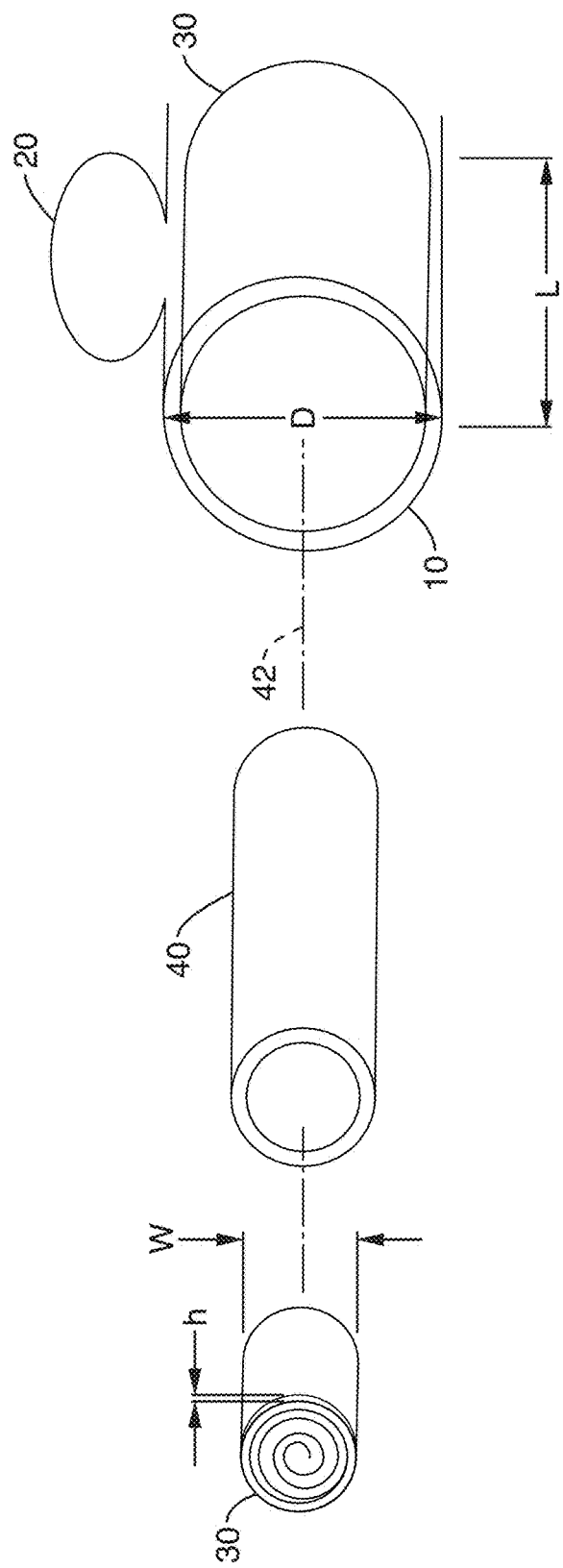
FIG. 3 illustrates a method in accordance with the present invention for preparing and delivering a thin-film microvascular stent to a location in a blood vessel/artery associated with an aneurysm.
Figure 4:
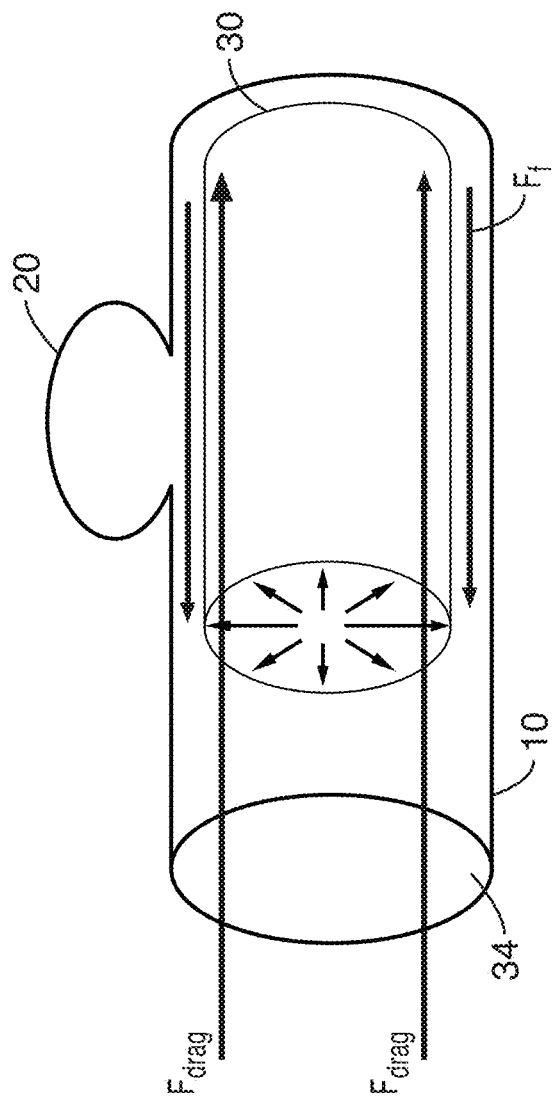
FIG. 4 illustrates the stent of FIG. 3 shown deployed in a vessel/artery.

FIGS. 3 and 4 illustrate a method in accordance with the present invention for preparing and delivering a thin-film microvascular stent 30 to a location in a blood vessel/artery 10 associated with an aneurysm 20. The stent generally comprises a sheet of thin film nitinol that has a thickness h of approximately 4 μm to 12 μm. The sheet 30 has a length L corresponding to the desired coverage at the aneurysm 20 within the artery 10, and width W corresponding to the inside diameter of the artery 10. The sheet is initially tightly rolled and placed into a small diameter catheter 40 (e.g., 0.69 mm ID).

The stresses induced in the film cause the material to become martensitic (i.e. stress induced phase transformation) and more malleable when compared to the austenitic film. Using an endovascular procedure, the catheter is guided through the vascular system to the aneurysm location 20 over a 0.014 inch (0.36 mm in diameter) guidewire 42. The thin film 30 is subsequently pushed out of the catheter 40 and deploys conformally with the artery 10 as shown in FIG. 3. When pushed out into the blood stream, the thin film 30 reverts to the higher stiffness austenite phase causing it to conformally deploy against the inner wall 34 of vascular blood vessel 20.

The stent 30 is sized to occlude the aneurysm 20 by completely wrapping around the vascular wall's interior surface 34 without migrating after deployment or blocking flow through the vessel 10. FIG. 4 illustrates the forces present in a deployed thin film stent 30. The forces consist of radial forces $F_{Radial}$, frictional forces $F_F$, and hemodynamic shear or wall drag force $F_{drag}$. The radial forces $F_{Radial}$ induced during stent deployment (from the stent reverting to its preformed shape) produce frictional or holding forces $F_{Radial}$ between the stent 30 and vascular wall 34. The blood flow through the stent 30 interior introduces hemodynamic shear stress or a drag force on the thin film. A balance of these forces is calculated to maintain the position of thin film microstent 30 so that it is immobilized and not free to migrate in the vascular system.

A basic fluid mechanics model is used to approximate the hemodynamic shear stress induced on the thin film from blood flow. These calculations assume that the vessel 10 is straight and the diameter is constant which limits the applicability of these results to some areas of the vascular system. The hemodynamic shear stress ($\tau_{wall}$) is calculated using Poiseuille's Law assuming a straight vascular wall. The total hemodynamic drag force $F_{Drag}$ on the film is:

$$F_{Drag} = \tau_{wall} \cdot A = \left(\frac{4\mu Q}{\pi r^3}\right) \cdot (2\pi r l) = 8\pi \mu \cdot l \cdot v \qquad \text{Eq. (1)}$$

where μ is blood viscosity, Q is blood flow rate, r is artery 10 radius, l is length (i.e., axial) of thin film stent, and v is velocity of blood flow. The velocity of fully developed pulsatile blood flow ranges between 0.5~1.0 m/s in human CNS (Central Nervous System) arteries, and the blood viscosity is approximately 0.004 Ns/m² (4 centipoise). The remaining two variables are functionally dependent upon artery size and thin film stent length. To immobilize the thin film stent, the frictional forces $F_F$ must be larger than the drag force $F_{Drag}$. The frictional force is proportional to the radial force developed between the thin film and vascular wall.

Estimating radial force $F_{Radial}$ from the microstent deployment is based on the assumption that the nitinol is thin, long and isotropic. Using these assumptions we argue that the deployment is similar to a long slender beam subjected to a internal bending moment. The radial force resultant $F_{Radial}$ is subsequently due to the bending moment produced by the nitinol unrolling in the austenite phase due to the shape memory effect. This radial force $F_{Radial}$ can be approximated by the following equation.

$$F_{Radial} = \left(\frac{E}{1-v^2} \cdot \frac{1}{24} \times h^3\right) \cdot \frac{1}{r} \cdot \frac{w}{l} \qquad \text{Eq. (2)}$$

where w is width, E is Young's modulus of the austenite phase of nitinol (83×10⁹ Pa), v is Poisson's ratio (v=0.33), and h is thin film thickness. The frictional force between the vascular wall and the thin film is related to the radial force and coefficient of friction. A conservative friction coefficient μ of 0.05 was used between thin film nitinol surface 30 and vascular wall 34 to estimate the frictional force (i.e., $F_F \propto \mu$).

The efficacy of a material used in a stent is subject to a number of criteria. Materials must not cause an excessive inflammatory response, must not be toxic to the body, and must not cause clotting in the blood stream. Strategies aimed at reducing or eliminating rates of thrombosis have included research into novel materials and surface treatments that prevent the adhesion of blood products.

Nickel-titanium alloys (NiTi or nitinol) are particularly beneficial for use in stents and for covering stents. NiTi is ideally suited as biocompatible material for use in many implantable medical devices, including stents and atrial septal defect occlusion devices. NiTi is biologically inert in physiological solutions; a titanium oxide layer forms on the metal's surface which prevents corrosion of the bulk material. Furthermore, nitinol is resistant to thrombus formation and does not calcify. When implanted within blood vessels and within the heart itself, NiTi has proven to be non-toxic, biocompatible, and non-thrombogenic.

The thin films that may be used to form stents in accordance with the present invention may be made from thin films of metal alloys that are phase transforming and/or exhibit twin boundary motion. For example, NiTi and other similar metal alloys exhibit a thermally induced crystalline transformation between a ductile martensite phase at low temperatures and a rigid austenite phase at high temperatures. NiTi exhibits both shape-memory and super-elastic properties. These metal alloys are referred to herein as thin-film memory or shape memory metal alloys. Upon cooling below the martensite temperature, unstrained NiTi has a twinned martensite structure. When placed under stress, the twin orientation is reorganized along the direction of stress. When heated above the austenite temperature, the material regains its rigid highly-ordered austenite phase and recovers the original shape in which it was crystallized. In the low temperature martensite phase, nitinol is exceedingly malleable and can be compressed into catheters. Upon heating (in many cases simply to body temperature), nitinol transforms into its austenite parent phase and recovers from the deformation induced in the martensite state. Thus, stents made from thin film NiTi (or other similar metal alloy) can make use of these shape memory properties. However, this does not preclude the use of purely martensite NiTi or possible other acceptable shape memory or pseudoelastic material.

Figure 5:
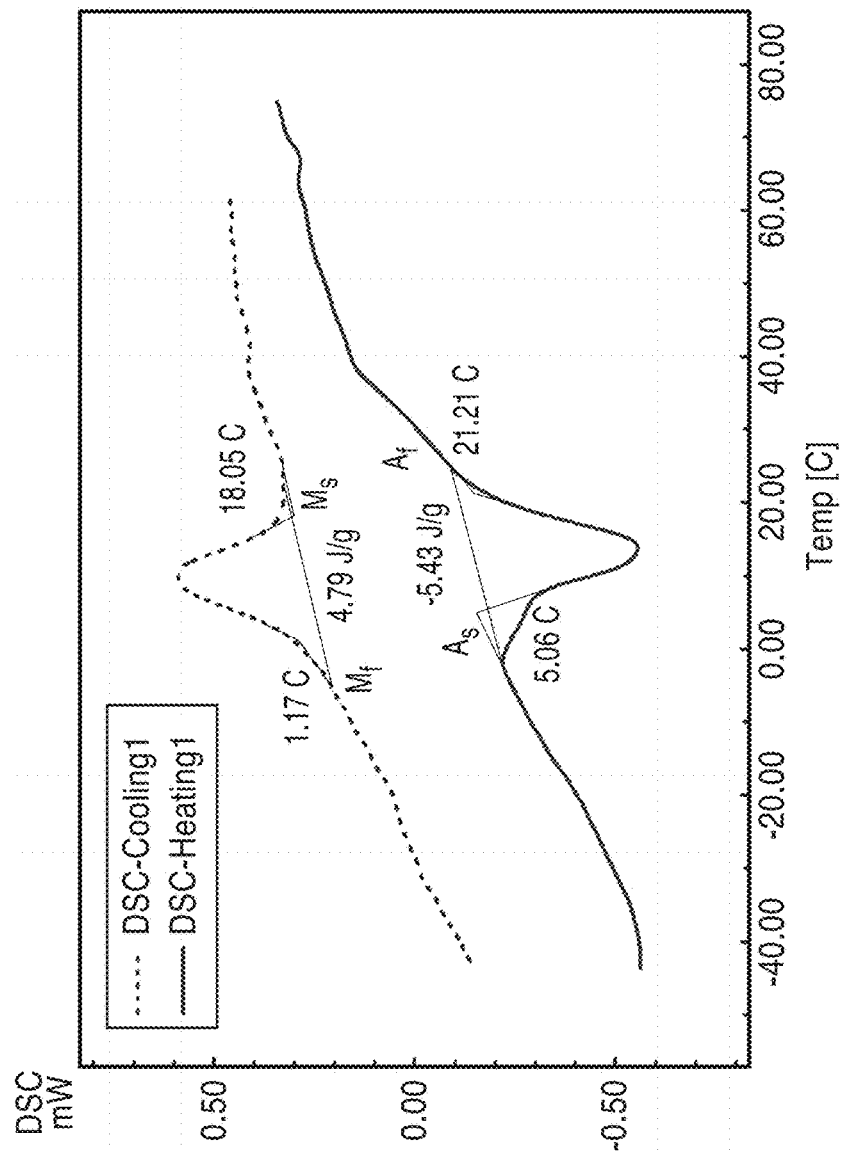
FIG. 5 is a graphic representation of a differential scanning calorimetry experiment.

In one embodiment, a shape memory alloy used to form a stent can have a starting temperature for transition to the austenitic phase of approximately 20° C. For example, a stent was made of thin film nickel-titanium alloy that was approximately 50.2 atom % titanium, and exhibited the following transition temperatures: (start of transition to austenitic phase) $A_s$=5° C.; (finish of transition to austentic phase) $A_f$=21° C.; (start of transition to martensitic phase) $M_s$=18° C.; and (finish of transition to martensitic phase) $M_f$=1° C. A graphic representation of the differential scanning calorimetry experiment from which these transition temperatures were determined is shown in FIG. 5.

Alternatively, the stent 30 may be configured so that it does not require the phase transformation, but rather solely relies on the malleability of the nitinol. In other words, the stent would produce the restoring deformation. The nitinol film can be in its martensitic state and rely solely on twin boundary motion.

Exemplary thin-film memory metal alloys useful in any of the embodiments of the present invention include the nickel-titanium alloys (NiTi), as well as alloys having the desired properties selected from the following: nickel-titanium-copper alloys (NiTiCu) and other copper-based alloys; gold-cadmium and other cadmium-based alloys (AuCd); nickel-titanium-platinum (NiTiPt) and other platinum-based alloys;

nickel-titanium-palladium (NiTiPd) and other palladium-based alloys; nickel-titanium-hafnium (NiTiHf) and other hafnium-based alloys; and nickel-magnesium-gallium alloys (NiMgGa), nickel-manganese-gallium alloys (NiMnGa) and other gallium-based alloys.

The thin film metal alloys of the present invention may be produced with various percentages of the constituent elements. For example, nickel-titanium alloys, such as nitinol, that contain about 50 atom percent nickel (atom % Ni) and about 50 atom percent titanium (atom % Ti) can be used. As another example, NiTi alloys that include from about 45 to about 55 atom percent nickel and from about 45 to about 55 atom percent titanium can be used. For example, the shape memory alloy can include from about 46 atom percent (atom %) to about 53 atom % of titanium. Nickel-titanium alloys with other atom percentages can also be used.

Although fabrication of thin film nitinol (about 8 microns in thickness) has been attempted using flash and vacuum evaporation, ion beam sputtering, and laser ablation, most of these fabrication methods have been unsuccessful in producing high quality uniform film required for medical applications. DC magnetron sputter deposition under ultra-high vacuum is a preferred method for the production of medical quality thin film nitinol, as it allows for high levels of process controllability and "batch-to-batch" consistency. The sputter deposition process involves ejecting atoms from a target material and directing them to form a thin film on a substrate. Target heating during sputtering creates films of uniform thickness and composition not achieved with conventional sputtering. This allows for precise process control of film composition.

For example, a film having a compositional variation of no more than about 1 atom percent can be produced. The target may be heated to a temperature of from about 200° C. to about 800° C., preferably to a temperature of from about 400° C. to about 700° C., and more preferably from about 550° C. to about 650° C.

In one embodiment, hot target sputtering was carried out as follows. A residual gas analyzer (Stanford Research Systems, Sunnyvale, Calif.) was used to monitor residual gas contamination levels prior to sputtering. Residual gases can deplete the amount of titanium reaching the substrate. The combined pressure of water, carbon dioxide, and carbon monoxide gases were maintained below $10^{-9}$ Torr during sputtering. An argon scrubber further cleaned the argon to 99.999% purity as required for the sputtering process. Sputtering of thin film nitinol onto a silicon wafer with 500 nm thick wet thermal oxide (other layers also used include barrier layers and lift off layers such as Cu, which can be lifted off the wafer using a chemical process) was accomplished with a 3-inch DC magnetron gun (MeiVac. Inc., San Jose, Calif.). A target made of bulk nitinol cut from a three inch boule of nitinol containing 49.5 atom % nickel and 50.5 atom % titanium (SCI Engineering, Columbus, Ohio) was used for the sputtering process. All films were deposited at base pressures below $5 \times 10^{-8}$ Torr and at an Ar pressure of $1.5 \times 10^{-3}$ Torr. The substrate-to-target distance was 4 cm and a sputtering power of 300 Watts was used. During deposition the substrate was translated back and forth in relation to the target at 45 degree arcs with 80 mm length to minimize compositional variation. The deposited amorphous film is crystallized by heating to 500 degrees Celsius for 120 minutes. Typically the film is annealed after removal from the wafer to prevent any diffusion or reactions with the substrate.

The thin memory metal alloy films of the present invention generally have a thickness of less than 50 microns, and preferably have a thicknesses ranging from about 0.1 microns to about 30 microns. Preferably, the thin films may have a thickness ranging from about 0.1, 1, 2, 4, 5, 10, 15, 20, 25, 30 or 50 microns to about 4, 5, 10, 15, 20, 25, or 30 microns. More preferably, the thin films may have a thickness of from about 4 microns to about 12 microns.

Thus, covering a stent with the thin memory metal film of the present invention (described in further detail below) will result in a minimal and inconsequential increase in the size of the overall device. For example, thin film NiTi can be manufactured in films of from about 5 to about 8 μm thickness, so that covering a stent with thin film NiTi adds very little bulk to the devices. For children, for neurointerventional applications, and for coronary applications, it is highly beneficial that covered stents maintain a very low profile. Many applications require that stents can be delivered through very small catheters even after covering them. The stent can have a thickness in the range of, for example, between about 2 μm, 4 μm, 6 μm, 7 μm, 10 μm, 17 μm, 18 μm, or 20 μm.

Thin memory metal alloy films 30 can be produced in a range of shapes and sizes. For example, thin memory metal alloy films can be made square or rectangular e.g. when laid flat, the sheet can have the appearance of a rectangle with a longer length dimension and a shorter width dimension. Each dimension of such a square or rectangle can be selected from a wide range. For example, the width W of such a square or rectangle may be in the range of, for example, between about 0.5 mm, 1 mm, 3 mm, 5 mm, 10 mm, 16 mm, 20 mm, 25 mm, 30 mm, or 40 mm. The width, W, is generally a function of the internal diameter of the lumen, and whether or not the film is wound as a spiral, single loop, double loop, etc. (described in further detail below).

Correspondingly, the length L of such a square or rectangle may be in the range of, for example, between about 0.5 mm, 2 mm, 5 mm, 15 mm, 20 mm, 30 mm, 50 mm, or 100 mm. Generally, the length L is a function of the vessel 10 and size of aneurysm 20 to be occluded.

Adjacent sides need not be perpendicular. The sheet 30 can have a form that is not an endless loop; for example, the sheet can have two distal edges as ends of the sheet, bounding the length dimension.

Thin memory metal alloy films may be made in a wide variety of shapes other than square or rectangular. For example, thin memory metal alloy films may be made to resemble other polygons, circles, ovals, crescents, or an arbitrary shape.

In one embodiment, photolithography and etching techniques may be used to generate precise two-dimensional shapes required to produce thin film nitinol sheets for covering the stents. For example, a positive photoresist may be spin coated onto an 8-micron thin film nitinol coated silicon oxide wafer. The photoresist (PR) may be exposed through a patterned glass mask (Computer Circuit Inc, Gardena, Calif.) and developed, leaving the desired PR pattern on the nitinol film. The unprotected portions of the thin film nitinol (areas without PR) may then be etched away in a 1:1:15 $HNO_3$:HF:$H_2O$ solution, and the remaining PR removed with acetone. The fabricated thin film nitinol sheets are then mechanically removed from the silicon oxide wafer. This photolithography approach reduces the number of imperfections on the edges of the thin film nitinol, thereby reducing/eliminating the incidence of tearing as compared to mechanical mechanisms.

After the thin film is formed, thin film nitinol may be removed from the substrate (e.g. wafer or silicon wafer) on which it was formed by using a crack and peel method to produce a free-standing film. Alternatively, a lift off method may be used, wherein the thin film nitinol is removed from the wafer by etching the sacrificial layer, for example, Cu. With the lift-off method, the Cu can be deposited onto a layer of silicon dioxide on top of the silicon wafer prior to depositing the NiTi thin film.

The thin film can then be annealed. For example, the thin film can be annealed after removal from the substrate for about 2 hours at approximately 500° C. The thin film can also be annealed on the substrate on which it was deposited through sputtering. However, this can result in diffusion of the atoms of the material of which the substrate is formed into the thin film, which can detrimentally affect the properties of the thin film.

After being annealed, the thin film 30 may be hot shaped to form a coil. For example, the thin film 30 may be hot shaped by heating the film to approximately 500° C. and holding it in a shape to which it is constrained for about 5 minutes. For example, the film 30 may be rolled into a cylinder having an outside diameter, that when in its expanded configuration, conforms with the inside diameter of the lumen and applies a radial force to the inner wall 34 of the lumen 10.

The thin film 30 may then be compacted into a form for delivery as shown in FIG. 3. For example, the thin film can be coiled more tightly into a compacted form for loading into and delivery through a catheter 40.

Figure 6:
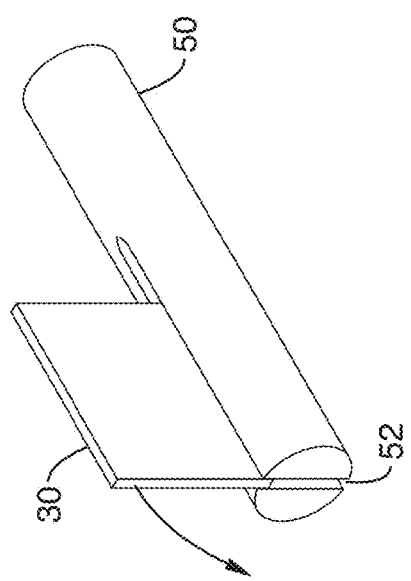
FIG. 6 illustrates a thin film stent coiled by using a cylindrical instrument.

As shown in FIG. 6, the thin film 30 may be coiled by using a cylindrical instrument, such as a split cylindrical instrument 50 having slot 52 at its distal end for retaining the film 30. An edge of the thin film 30 is be inserted into the slot 52 of the instrument 50, and the instrument 50 is then rolled to coil the thin film 30 into a cylindrical configuration for deploy.

The rolled thin film into the form of a coiled stent 30 is then delivered by a catheter 40 (e.g. size 3 French or less) as shown in FIG. 3. The stent 30 in its compacted form can be inserted into and deployed from a delivery tube, such as a catheter, having a diameter of about 1 mm or less, for example, from a delivery tube, such as a catheter, having a diameter of about 0.5 mm or less.

Once deployed, e.g. by being pushed out of the catheter 40, the stent 30 assumes (or attempts to assume) its shape prior to being compacted to fit into a catheter 40. As shown in FIG. 7A, the stent may assume the shape of a cylindrical tube 60 having an outer diameter D larger than the inner diameter of the catheter 40.

Because the stent 30 according to the present invention is very thin, it assumes a low profile when deployed in a blood vessel. Therefore, when deployed in a blood vessel, the stent 30 do not substantially impede the flow of blood through the vessel 10. The low profile of a stent according to the present invention is illustrated in FIG. 4 where it is shown in a configuration of deployment in a blood vessel 10.

In the generally tubular shape 60 shown in FIG. 7A, the inside of the tube 62 is hollow, so that, for example, a fluid can travel into the shape through a proximal end 66, through the shape (along the central axis 64), and out of distal end 68 of the tube 60.

The generally tubular shape 60 shown in FIG. 7A may also be varied to be other than a perfectly cylindrical shape. For example, in FIG. 7B, the tube may comprise an elliptical shape 80.

Figure 7C:
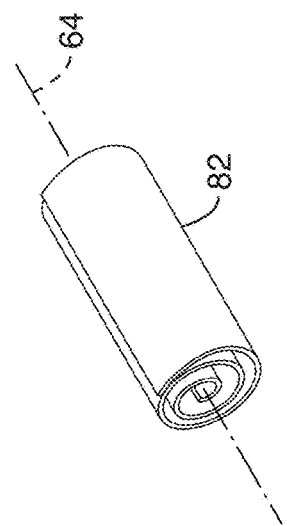
FIG. 7C shows a spiral shaped thin film stent curled to form a path around a central axis.
Figure 7B:
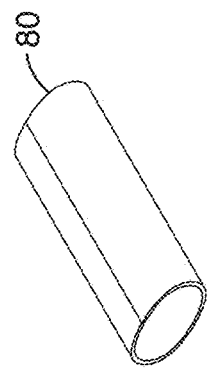
FIG. 7B shows an oval-shaped thin film stent.
Figure 7A:
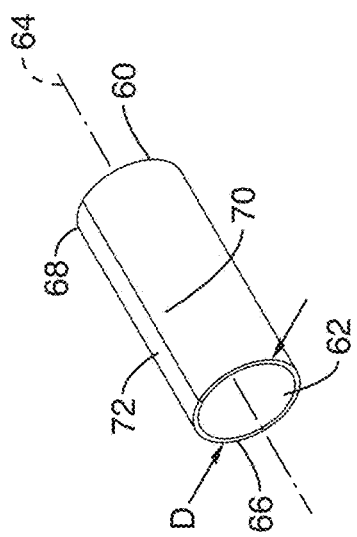
FIG. 7A, shows a thin film stent rolled into a cylinder with no overlap.

As shown in FIG. 7C, a spiral shape 82 can be formed by curling a sheet, so that if the sheet is traced from one end, a path around a central axis 64 is followed. As the path goes around the central axis 64, the path generally moves either continuously inward toward the central axis 64 or continuously outward away from the central axis 64. The path may also have excursions from such continuously inward or continuously outward movement.

A broken ring, as shown in FIG. 7A, is similar to a spiral, except that there is no overlap, i.e., the winding number is 1 or less. That is, a broken ring can have the ends 70 and 72 just touching (as shown in FIG. 7A), or can have the ends separated (e.g. forming a "c" shape (not shown)).

Compacted, for purposes of the present invention, means that an object, for example, a sheet, is temporarily shaped so that at least one dimension of the object is smaller than in the deployed form of the object.

For children or adults who require neurointerventional applications, it is highly beneficial that the stent maintains a very low profile. Many applications require that the stents be delivered through very small catheters. The use of thin film metal alloy for stents in accordance with the present invention allows for the construction of very low profile stents for use in the treatment of, for example, aneurysms of the central nervous system vasculature and brain vessel aneurysms.

The stent 30 can be used, for example, to support a body cavity, to maintain a passage through a body cavity, and/or to seal off a body cavity. For example, a stent 30 implanted into a blood vessel 10 can act to prevent the closing of the blood vessel. The stent can be hollow, so that fluid can travel through it along its central axis. For example, a stent implanted into blood vessel 10, for example, a blood vessel supplying the peripheral or central nervous system, can seal off an aneurysm 20 from the blood vessel. For example, the stent can be implanted in body cavities, such as blood vessels supplying the central nervous system, in peripheral blood vessels, and in coronary blood vessels, in order to treat diseases and disorders of the blood vessels such as peripheral artery disease (PAD).

When the stent 30 is deployed or placed inside a body cavity, for example, a blood vessel, it can distort somewhat. For example, the stent may not have a perfectly cylindrical shape, a perfect spiral shape, or another idealized shape, but may be distorted from this ideal shape, e.g., to conform to a support on the walls of the vessel.

The apparatus, e.g. stent 30 formed of the thin film can be advanced with a catheter 40, for example, on a 3 French (3 Fr) delivery system. The stent can be self-expanding. When the apparatus 30 is advanced into position within the body, the thin film NiTi stent can unravel, so that the stent expands to cover the inner surface 34 of the blood vessel 10 into which it was deployed. The inner surface 34 of the blood vessel 10 is that part of the blood vessel that can be in contact with fluid moving through the vessel when no stent is in place. A large fraction of the outer surface of the stent 30 can be in contact with the inner surface 34 of the blood vessel 10 into which the stent was deployed. For example, at least about 80% of the outer surface of the stent 30 can be in contact with the inner surface 34 of the blood vessel into which the stent is deployed.

The stent 30 can be deployed in a blood vessel adjacent to an aneurysm 20, so that in its deployed form, the stent covers at least a portion of the aneurysm. See, for example, FIG. 2C. In its deployed form, the stent can cover at least 40% of the area of a passage from the blood vessel to the aneurysm.

The apparatus, e.g. thin film stent 30, can then be advanced into a catheter 40. When the apparatus 30 is advanced into position within the body and released from the catheter 40, the thin film memory metal of the stent unravels as it is trained to do (as it is heated or as it simply uses twin boundary motion forced by the stent) and the stent expands. For example, when the thin film stent 30 is released from a delivery system 40, the austenitic shape memory of the thin film can allow the stent to expand and cover the inner surface 34 of a blood vessel 10 into which it is deployed.

The thin film 30 may be perforated or non-perforated. For example, the thin film can be solid, without holes, pores, or open slots. In this configuration, the thin film can be impermeable to body tissue and fluids.

For certain neurovascular applications, the thin film metal stent 30 is ideally configured to be able to bend around curves of small radii. This is because the blood vessel 10 to be treated can be of small radius and can be tortuous, or the blood vessels through which the stent must pass in order to reach the blood vessel to be treated are tortuous.

In order to allow the stent to bend around curves of small radii, for example, for the treatment of certain aneurysms, the stent 30 can be made to have a short length L. The stent can also be made to have a short length L to improve its ability to track around tortuous vessels, for example, over a guide wire 42.

Figure 9:
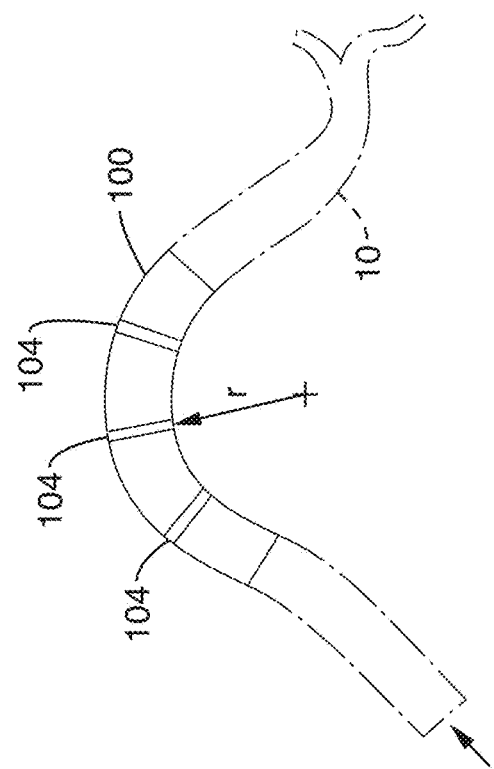
FIG. 9 shows the stent of FIG. 8 deployed in a portion of a blood vessel forming an arc.
Figure 8:
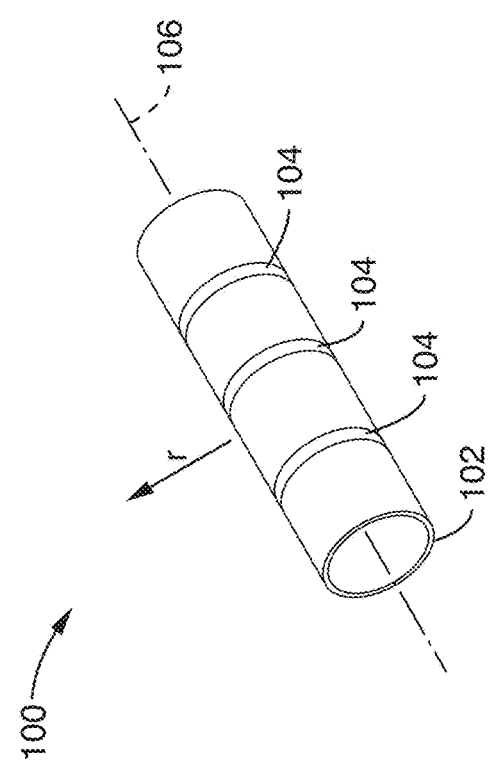
FIG. 8 shows a stent having a plurality of joints that allow the stent to bend more freely.

Referring to FIGS. 8 and 9, a stent 100 is shown having a plurality of joints 104 that allow the stent 100 to bend more freely, and thus allow the stent to bend around curves of small radii, and treat, for example, aneurysms which extend along a blood vessel. Thus, the thin film sheet 102 may have at least one joint 104 that allows the structure of the stent to bend about an axis in the radial direction.

As shown in FIG. 9, the stent 100 may be deployed in a portion of a blood vessel 10 forming an arc (e.g. 180 degrees) and having a radius r (e.g. 1.5 mm to 3 mm), in order to treat an aneurysm adjacent to or at arced portion of the blood vessel 10.

The stent 100 has a longitudinal direction or axis 106, which extends along the center of the tube formed by the stent. Thus, if the stent 100 is bent, the longitudinal direction 106 has the form of a curve. At a given point along the longitudinal direction, a radial direction r is perpendicular to the longitudinal axis 106. In bending around the curve of a blood vessel 10, the stent 100 bends around an axis in the radial direction.

The joint 104 may comprise a strip on the rectangular thin film sheet 102. For example, the strip can have a long direction and a short direction, with the long direction being parallel to the distal edges of the sheet, and the short direction can be perpendicular to the distal edges of the sheet. The ratio of the long direction over the short direction can be, for example, at least 2. Thus, when the thin film is rolled into a spiral to form the stent, a strip which forms the joint can have the form of a band around the stent (when the stent is formed from a spiral, the strip also has the form of a spiral rather than an endless loop).

In an embodiment, the thin film sheet has an average thickness. This average thickness can be the volume of the material of which the thin film sheet is formed divided by the area of the thin film sheet. The strip has an average thickness that is the volume of thin film sheet material in the strip divided by the area of the strip. The average thickness of the strip is no greater than about 90% of the average thickness of the thin film sheet.

In an embodiment, the memory metal of which the strip 104 is formed is continuous, that is, has no perforations. The strip 104 may have a different local thickness. In one embodiment, the local thickness of the strip 104 is no greater than about 90% of the thickness of the sheet 102, and preferably no greater than about 50% of the thickness of the sheet 102, and more preferably no greater than about 25% of the average thickness of the thin film sheet 102.

The strip 104 and/or the thin film sheet 102 may also be perforated, for example, in order to improve the flexibility of the stent formed. In one embodiment, the thin film sheet or strip is perforated with at least one hole. For example, the hole can have a profile area of less than about 2000 µm². The profile area is the area in the thin film sheet occupied by the hole. For example, the hole can have a maximum spanning distance of less than about 50 µm. The maximum spanning distance is the maximum distance from one point on the perimeter of the hole to another point on the perimeter of the hole. Thus, for example, the maximum spanning distance of a hole shaped as a circle is the diameter of the circle, and is less than the maximum spanning distance of a hole shaped as an ellipse that has the same area as the circle.

Figure 10B:
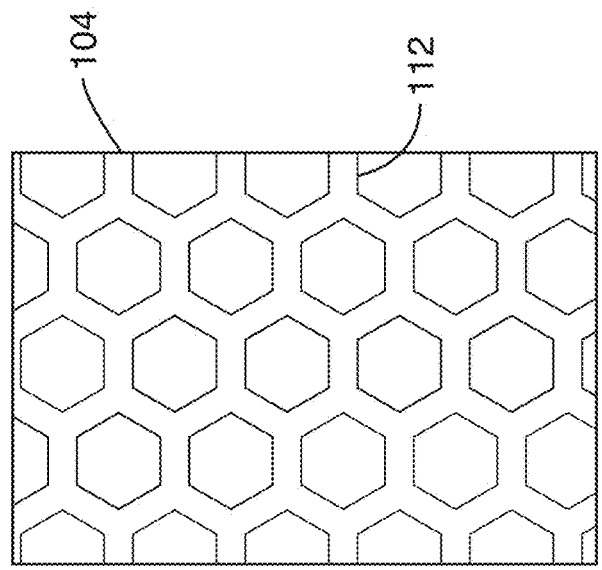
FIG. 10B shows a photograph of a joint in the form of a strip a having holes in a hexagonal array.
Figure 10A:
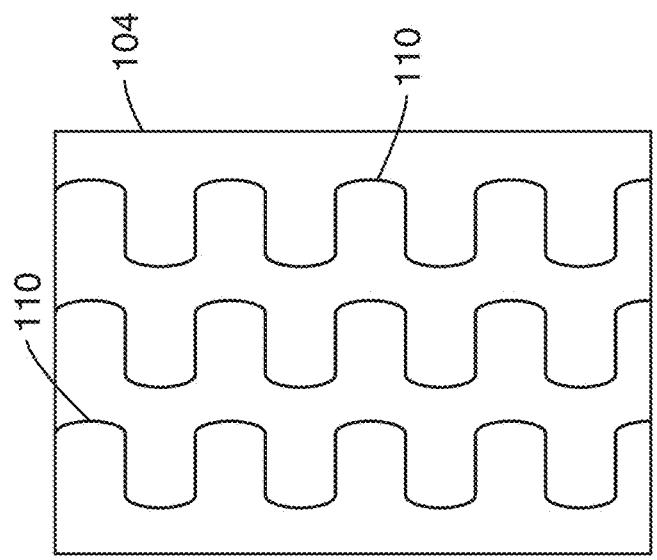
FIG. 10A shows a joint in the form of a strip having a series of holes separated by undulating wires of metal.

For example, FIG. 10A shows a joint in the form of a strip 104 having a series of holes separated by undulating wires of metal 110. Thus, the holes have the form of slots with "fingers" projecting perpendicularly from a long direction of the slot, the "fingers" of adjacent slots being interdigitated.

A hole that perforates the thin film sheet can have any one of a number of profiles. The profile is the form of the hole when the hole is viewed face on. For example, the hole can have a circular, elliptical, or diamond-shaped profile. FIG. 10B shows a photograph of a joint in the form of a strip 104 having holes 112 in a hexagonal array, where each hole 112 has an approximately hexagonal or oval form. Holes can also be positioned in other types of arrays, for example, periodic, quasiperiodic, and nonperiodic arrays. Holes can have other forms, such as polygonal or an arbitrary shape.

Figure 10D:
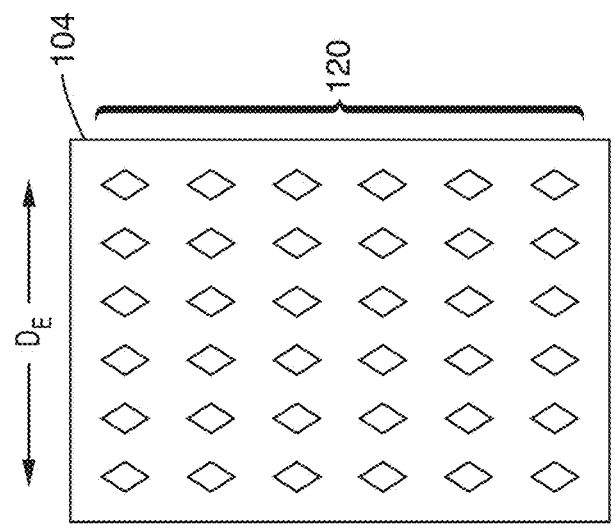
FIG. 10D illustrates a thin film strip having a plurality of diamond shaped fenestrations.
Figure 10C:
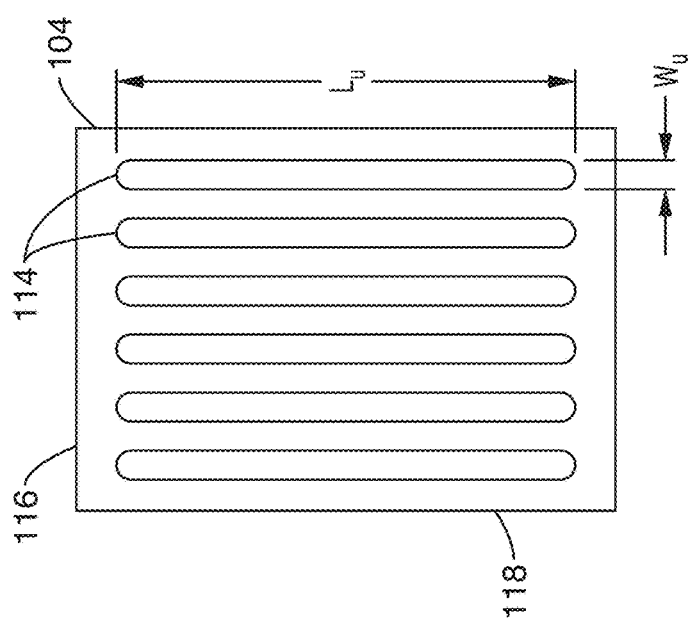
FIG. 10C shows a joint in the form of a strip that includes a series of holes having the form of slots.

FIG. 10C shows a joint in the form of a strip 104 that includes a series of holes having the form of slots 114.

The slots 114 have a long direction $L_u$ and a short direction $W_u$. The long direction $L_u$ may be parallel to a distal edge 118 of the thin film sheet. The short direction $W_u$ may be perpendicular to a distal edge 118 of the thin film sheet and parallel to a short edge 116 of the film 104. The short direction $W_u$ may be less than about 50 µm.

Figure 11B:
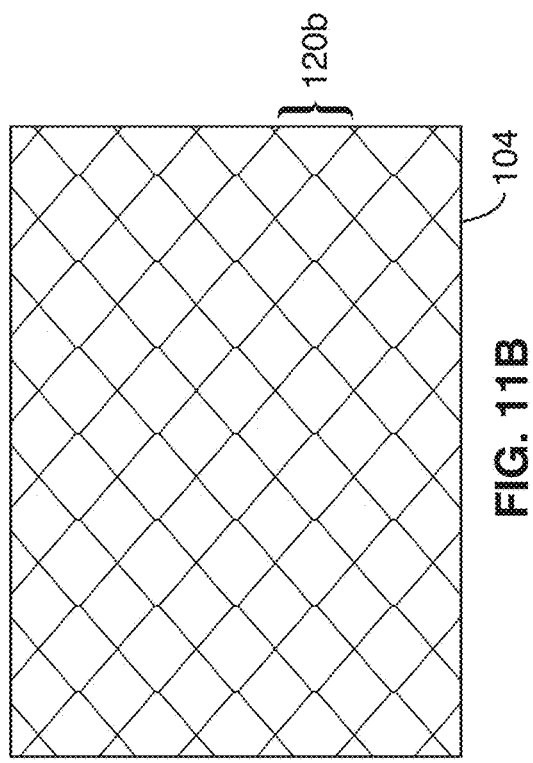
FIGS. 11A and 11B illustrate the strip of FIG. 10D elongated over 400% from a compressed state to an expanded state.
Figure 11A:
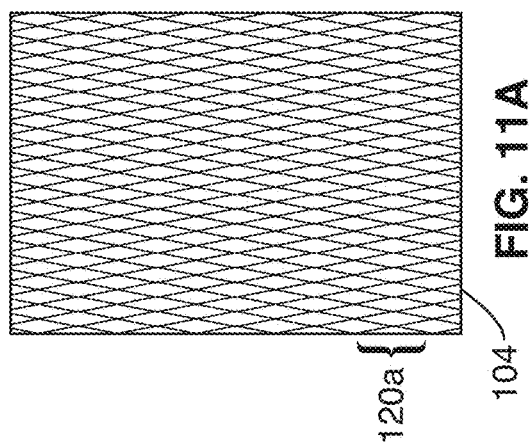

FIG. 10D illustrates a thin film strip 104 having a plurality of diamond shaped fenestrations 120 that allow further flexibility, and particularly expansion and compression in direction $D_E$. As shown in FIGS. 11A and 11B, the strip 104 may have elongation over 400% from a compressed state 120A to expanded state 120B.

As shown in the embodiment of FIG. 8, the thin film sheet 102 may be continuous, e.g. non-perforated, in a region outside of the joint strip 104, and is porous (e.g. fenestrated according to any of the patterns shown in FIGS. 10A-D) within the strip 104.

Alternative system 150 shown in FIG. 12 comprises a thin film sheet 160 fenestrated with a plurality of diamond shaped holes 120, and wrapped around a collapsible, truss-like stent 152 for additional rigidity.

FIGS. 13A and 13B illustrate method for attaching a thin film 170 having a plurality of fenestrations 176 to a collapsible truss 152. FIG. 13A shows the vessel side (outside surface) of the stent 150 with stitching 172 tied in a knot 174, and FIG. 13B showing the internal side of the stent 150 with the stitching 172 looped around the truss 152 and through the fenestrations 176.

FIGS. 14A-14C illustrate additional truss shapes that may be implemented along with a thin film 30 according to the present invention.

The coil structure 200 shown in FIG. 14A comprises a superelastic nitinol wire 204 with a plurality of coils 202.

The wire may be manufactured by winding a 0.13 mm diameter superelastic nitinol wire 204 around a cylinder (not shown) approximating the radius of the arterial wall, and heating at 500° C. for 30 minutes to shape set the nitinol wire 204. After hot shaping, the coil 200 may be pulled straight to induce a stress induced phase transformation and inserted into a delivery catheter 40 containing the rolled microstent 30 (as described above). The coil 200 may be positioned such that there is substantially equal length of coil 204 extending out both sides of the rolled microstent sheet 30. When deployed, one-third of the coil 200 may initially be pushed out of the catheter 40 prior to deploying the thin film microstent 30. Once the thin film portion 30 of the stent is delivered, the remainder of the wire coil 200 may then be deployed.

FIG. 14B illustrates a "zigzag" structure stent 210 having a plurality of folds 212. Stent 210 may be formed by setting 0.13 mm diameter superelastic nitinol wire on a cylinder approximating the radius of the arterial wall and heating at 500° C. for 30 minutes to shape set. After hot shaping, the structure may be physically compressed to induce a stress induced phase transformation and then inserted into the delivery catheter 40 as described above for coil. Inside the catheter, the wire skeleton 210 preferably has 3-4 mm of overhang length out of both ends of the rolled microstent sheet 30. This structure is configured to be collapsed into an ultra-low diameter catheter (i.e., 0.69 mm diameter) with a rolled microstent 30. The supporting nitinol 212 is designed to retain sufficient longitudinal flexibility to permit the catheter 40 and structural backbone to navigate through a tortuous cerebral vascular system.

FIG. 14C shows a stent structure 220 having dual-zigzag structures 214 and 216. This stent 220 provides radial force at the ends of the thin film nitinol stent 30, while preserving flexibility in the body of the stent.

The thin film sheet 30 may have a winding number that corresponds to the number of revolutions of the sheet about an axis, of greater than 1. Thus, with increasing radial distance from the center of the stent (the longitudinal direction), more than one layer of the thin film can separate the inner region of the stent through which fluid can pass from the outer environment of the stent. The longitudinal edges of the sheet can overlap each other.

FIG. 15 illustrates a sheet 180 having a length between end 70 and opposite end 72 sufficient to form two coils (e.g. winding number of 2+) when expanded within the lumen 10.

Alternatively the thin film sheet of the stent can have a winding number of less than about 1 (e.g. "c" shape). Thus, the stent can be formed to not close back on itself, so that in certain radial directions, the inner region of the stent through which fluid can pass is open to the outer environment of the stent.

A thin film sheet 60 having a winding number of about 1 is shown in FIG. 7A. For example, the stent can be formed so that the longitudinal edges 70 and 72 of the thin film 60 touch each other.

The thin film sheet of the structure of the stent can include a notch. For example, a notch can extend from where the strip meets a longitudinal edge of the sheet along a portion of the strip. For example, the notch can extend from the longitudinal edge and along the strip half-way across the thin film sheet.

FIG. 16 illustrates an embodiment of a thin-film stent 250 according to the present invention having a tab-and-slot configuration. The stent 250 is formed from a sheet that includes tabs 256 at first end 254, the tabs 256 projecting in the width direction, i.e., perpendicular to the length dimension of the sheet. The sheet 250 also comprises a slot 260 at second end 258 of the sheet. The first end 254 with the tabs 256 may be inserted through the slot 260 to secure the cylindrical shape of the stent 250.

As shown in FIG. 16, the first end 254 with the tabs 256 is inserted through the slot 260 such that the first end 254 extends into the internal radius of the stent 250 and wrapped around itself to have a spiral form, i.e. an inside roll tab-and-slot design. The sheet 250 generally has a tubular structure, wherein the spiral formed sheet 250 can be used alone as a stent.

A stent 250 having an inside roll tab-and-slot design can unroll in a belt/buckle design. The buckle maintains the sheet's alignment, and prevents the sheet from unraveling too far. A stent having an inside roll tab-and-slot design can have its sheet unraveling from the inside out, assuring proper stent coverage and alignment.

In an alternative embodiment shown in FIG. 17, a stent 270 comprises a sheet formed into a tab-and-slot design the first end 254 with the tabs 256 is inserted through the slot 260 such that the first end 254 extends outward from the internal radius of the stent 270 and wrapped around itself to have a spiral form with outside roll tab-and-slot design.

In other words, a stent 270 having an outside roll tab-and-slot design can unroll in a belt/buckle design. The buckle maintains the sheet's alignment, and prevents the sheet from unraveling too far. A stent having an outside roll tab-and-slot design can have its sheet unraveling on the outside of the belt, assuring proper stent coverage and alignment.

The sheet, whether in the form of a spiral 82 (FIG. 7C), an inside roll tab-and-slot design 250 (FIG. 16), an outside roll tab-and-slot design 270 (FIG. 17), or in another form not shown, can have a compacted form to facilitate its delivery into a body cavity, for example, either inside or on a catheter 40. By compacted, the sheet is temporarily shaped, so that at least one dimension of the generally tubular structure formed by the sheet is smaller than in the deployed form.

For example, the sheet can be wrapped tightly, so that it has a large winding number, or the sheet can be wrapped loosely. A sheet wrapped tightly, so that it has a large winding number, can be in a compacted form, because the diameter of the generally tubular structure formed by the sheet is smaller than it would be if the sheet were wrapped loosely. In a compacted form, a structure can have a first internal diameter. For example, when the sheet is wrapped tightly, the structure formed can have a first internal diameter extending from the inside surface of the innermost layer of the sheet, across the central axis, to an opposite point on the inside surface of the innermost layer of the sheet.

A sheet wrapped loosely, so that it has a small winding number, can be in a deployed form, because the diameter of the generally tubular structure formed by the sheet is larger than it would be if the sheet were wrapped tightly. In a deployed form, a structure can have a second internal diameter. For example, when the sheet is wrapped loosely, the structure formed can have a second internal diameter extending from the inside surface of the innermost layer of the sheet, across the central axis, to an opposite point on the inside surface of the innermost layer of the sheet. The second internal diameter can be larger than the first internal diameter. The sheet in its deployed form can be impermeable to body tissue and fluids.

A sheet formed of a thin film memory metal alloy can be induced to transition from its compacted form to its deployed form by a change in temperature. Alternatively, a sheet which is held under tension in its compacted form, e.g.

because it is inside a catheter, can be induced to transition to its deployed form by a release of the tension, e.g. after the sheet is placed in a blood vessel and the catheter is removed. When the sheet is induced to transition from its compacted form to its deployed form by a change in temperature or by a release of tension, no extrinsic force is required to expand the sheet to its deployed form.

The expansion of the sheet to its deployed form can be driven by a phase change of the shape memory alloy, and can be driven by super-elasticity of the shape memory alloy.

In its deployed form, a sheet formed of a thin film memory metal alloy can, for example, have the form of a spiral 82, an inner loop tab-and-slot design 250 (FIG. 16), an outer loop tab-and-slot design 270 (FIG. 17), a ring, 60 (FIG. 7A), a broken ring or another configuration. A broken ring is similar to a spiral, except that there is no overlap, i.e., the winding number is 1 or less. A ring can have the ends just touching, and a broken ring can have the ends separated.

A stent formed of a sheet of thin film memory metal alloy is not limited to a spiral, inside roll tab-and-slot, or outside roll tab-and-slot design. For example, a sheet of thin film memory metal alloy can be used to form a stent having a compacted form with any means for packaging the area of the sheet into a smaller circumference than the deployed circumference, such as folds, coiling, and layers. These include packaging means like a spiral, but also having outward protrusions to resemble a star, a twisted star, a keyed wheel, or other configurations.

Furthermore, even though the stent may be designed to have a particular shape for its compacted form, often, when the stent is placed in or on a catheter, the compacted form may be distorted from the designed shape. For example, a sheet of thin film memory metal, when placed in or on a catheter, may not have the ideal shape of a spiral, tab-and-slot, star, twisted star, keyed wheel, or other configuration. Rather, the sheet may be distorted from this ideal shape.

Referring to FIG. 18, system 300 may include a thin-film stent 30 disposed around an inner tube 302. The inner tube 302 comprises a hollow bore 304 to allow a fluid (e.g. blood) to travel into the inner tube 302 through one end, and out of the other end of the inner tube. The walls of the inner tube 302 may be porous or non-porous. For example, the inner tube 302 may be a coil or a mesh. The thin film sheet 30 is preferably wrapped around the inner tube 302. Thus, the inner tube 302 can serve as a support for the thin film sheet 30.

The inner tube 302 may be of such structure or material to have a compacted form and a deployed form. For example, the compacted form of the inner tube 302 can have a diameter less than or equal to the first internal diameter of the structure of the thin film sheet 30 in its compacted form. The deployed form of the inner tube 304 can have a diameter greater than the first internal diameter of the structure of the thin film sheet in its compacted form. The inner tube 302 in its compacted form can exert an outward directed radial force. This outward radial force can cause the inner tube 302 to expand, and can assist the structure of the thin film sheet 30 in expanding to its deployed form. The inner tube 302 in its deployed form can exert an outward radial force. The outward radial force exerted by the inner tube 302 can increase the pressure applied by an outer surface of the thin film sheet 30 onto a body cavity, such as the wall of a blood vessel 10. This outward radial force can help maintain the stent 300 in a given position in a body cavity, for example, in a blood vessel 10, without sliding, e.g., without blood flow causing the stent to slide.

To exert the outward radial force, the inner tube 302 may comprise an elastic material, e.g. a shape memory alloy. The change of the inner tube 302 from its compacted form to its deployed form can be induced by a change of temperature or can be caused by twin boundary motion.

In addition to its shape-memory and super-elastic properties, thin film nitinol possesses remarkably high tensile strength. These properties make it particularly amenable for use in transcatheter devices. Furthermore, thin film nitinol allows for the construction of extremely low profile stents. When this material is manufactured as a thin film, there is little room for fluctuations in surface texture, resulting in an extremely smooth surface. In contrast to bulk nitinol, a DC hot target sputtering process in accordance with the present invention produces thin films of nitinol that are free of contaminants and uniform in composition, in addition to being more resistant to corrosion in a biological environment.

Used alone as a stent, the sheet 30 of thin film memory metal alloy may be housed in a catheter 40 or sheath and delivered to the place in the body, e.g., a part of a blood vessel 10, where it is to be deployed. The stent 30 can then be unsheathed, so that the sheet of thin film memory metal alloy expands into its deployed form. The expansion can be driven, for example, by a temperature induced phase change in or by the super-elasticity of the sheet.

The stent 30 formed from thin film memory metal alloy can be made radio-opaque by the addition of radio-opaque markers of a dense metal. The radio-opaque marker can be formed of a bio-inert metal. For example, markers of gold, platinum, or palladium, metals which can appear opaque on radiographs and which are substantially bio-inert, can be added to the thin film memory metal alloy of a stent. Such markers can be added to thin film shape memory metal alloy by mechanical attachment, welding, bonding, or sputter deposition. For example, a sputtering mask with holes can be placed over a thin film sheet of memory metal alloy. The sputtering mask thus can define masked and non-masked areas on the thin film sheet. A radioopaque metal, such as gold, platinum, or palladium, can be sputtered through the holes to deposit on the non-masked areas of the thin film sheet to form markers. The sputtering mask can be formed with a photolithography technique. For example, a photoresist can be spin coated onto the thin film, the photoresist can be exposed to a pattern of light and developed to form the sputtering mask. Alternatively, a radio-opaque marker can be mechanically attached to the thin film.

In an alternative embodiment, a neurovascular stent 30 according to the present invention can be delivered to and deployed at a desired position in a blood vessel 10 or other body cavity without the use of a catheter. The stent can be maintained in its compacted form by a self-contained constraining device other than a catheter.

For example, for system 350 shown in FIG. 19, a stent 30 formed from a thin film sheet of memory metal wrapped into a spiral is held in a compacted form via a ring 352 circumscribing the spiral thin film sheet of the stent 30. The stent 350 in its compacted form can be delivered to a desired position in a blood vessel 10 or other cavity by any of a number of procedures, for example, pushing by a flexible rod 354 that can have a smaller diameter than a catheter, pulling by a wire, or, for a stent that includes a ferromagnetic material, maneuvering by an externally imposed magnetic field. When the stent is in the desired position, the ring 352 that maintains the stent 30 in its compacted form is removed, so that the stent expands 30 to its deployed form.

The removal of the ring 352 can be effected by any of a number of procedures and devices. For example, a wire 356 connected to the ring 352 can pull on the ring in the same direction as a flexible rod 354 maintaining the stent in the desired position, or a wire connected to the ring can pull on the ring in the opposite direction as a wire maintaining the stent in the desired position. The ring 352 may be flexible, like a wire, so that it can be easily retracted through the blood vessel 10 or other body cavity to an exit point. Alternatively, the ring can include a ferromagnetic material, and a magnetic field can be used to displace the ring from the stent, while the stent is maintained at the desired position with, for example, a flexible rod or a wire. Alternatively, the stent can include a ferromagnetic material, the ring can be maintained at the desired position with, for example, a flexible rod or a wire, and a magnetic field can be used to displace the stent to a desired position from the ring. Alternatively, the ring can be constructed of a biodegradable material, so that after a predetermined amount of time, the ring degrades and the stent expands to its deployed form.

FIG. 20 shows an alternative system 360 for retaining a thin film sheet of memory metal 30 wrapped into a spiral in a compacted form with a loop 366 that passes through a first hole 362 in one part of the sheet 30 and a second hole 364 in another part of the sheet. Thus, a stent 30 in its spiral compacted form comprises one or more aligned holes 362, 364 passing through the layers. The loop 366 passes through the several layers, preventing the layers from moving with respect to each other and preventing the spiral 30 from unraveling. The loop 366 can be formed by, for example, the loop passing toward the center of the stent through one set of aligned holes 362 and then passing toward the outside of the stent through another set of aligned holes 364, as shown in FIG. 20. Alternatively, the loop can be formed by, for example, the loop 366 passing toward the center of the stent through one set of aligned holes 362, out of an end of the tubular shape of the stent, and around to the outside of the stent, so that an endless loop is formed (not shown).

The stent may be delivered to a desired position in a blood vessel or body cavity by, for example, a flexible rod 354, wire, or magnetic field. When the stent is in the desired position, the loop 366 that maintains the stent in its compacted form can be broken and removed, so that the stent expands to its deployed form. This breaking and removal of the loop can be effected by any of a number of procedures and devices. For example, a wire connected to the loop 366 may pull on the loop in the same direction as a flexible rod maintaining the stent in the desired position, or a wire connected to the loop may pull on the loop in the opposite direction as a wire maintaining the stent in the desired position. The loop 366 itself may be flexible, like a wire, so that it may be easily retracted through the blood vessel or other body cavity to an exit point. Alternatively, the loop 366 may include a ferromagnetic material, and a magnetic field may be used to displace the loop from the stent, while the stent is maintained at the desired position with, for example, a flexible rod or a wire. Alternatively, the stent may include a ferromagnetic material, the loop may be maintained at the desired position with, for example, a flexible rod or a wire, and a magnetic field may be used to displace the stent to a desired position from the loop. Alternatively, the loop 366 may be constructed of a biodegradable material, so that after a predetermined amount of time, the loop degrades and the stent expands to its deployed form.

Instead of the loop 366 in FIG. 20, a rivet 368 may be used to maintain the stent 30 in its compacted form by passing through a set of two or more aligned holes in two or more layers, 362, 364 of the stent 30. The rivet 368 may be removed by pulling or pushing on the rivet or the stent by, for example, a flexible rod, wire, or magnetic field, similar to the ways in which a loop may be removed. So that the rivet is not prematurely displaced, the rivet may have a flange 370 at each end of the rivet with a diameter greater than the holes through which the rivet passes. Alternatively, the rivet may be constructed of a biodegradable material, so that after a predetermined amount of time, the rivet degrades and the stent expands to its deployed form.

For the embodiments of a self-contained constraining device in which the stent in its compacted form includes one or more sets of aligned holes in the layers of the thin film metal sheet that are in a spiral, the stent and the self-contained constraining device may be designed, so that after the self-contained constraining device allows the stent to expand to its deployed form, the holes (e.g. 362, 364) are no longer aligned, so that fluid in the interior of the stent is impeded from passing through the holes to the exterior of the stent.

In another embodiment, a stent 30 may be maintained in a compacted form with a clip (not shown) that fastens two portions of the sheet to each other. For example, a stent may include a first protrusion extending inward from the longitudinally running edge of the sheet at the innermost layer of the spiral and a second protrusion extending inward from a point on the sheet next to where the sheet becomes covered by the innermost layer of the spiral. When the stent is in its compacted form, the first protrusion and the second protrusion may be adjacent to each other and maintained adjacent to each other with a clip, so that the stent is maintained in its compacted form and the spiral of the thin film metal sheet does not unravel.

Alternatively, the first protrusion can extend outward from the longitudinally running edge of the sheet at the outermost layer of the spiral, the second protrusion can extend outward from a point on the sheet next to where the sheet becomes covered by the outermost layer of the spiral, and the first and second protrusions can be held together by a clip.

Alternatively, a clip can press together the distal edges of the layers of the spiral at an end of the tubular shape of the stent, or two clips can press together the distal edges of the layers of the spiral at each end of the tubular shape of the stent.

The stent may be delivered to a desired position in a blood vessel or body cavity by, for example, a flexible rod, wire, or magnetic field. When the stent is in the desired position, the clip or clips that maintain the stent in its compacted form may be removed, so that the stent expands to its deployed form. This removal of the clip or clips may be effected by any of a number of procedures and devices. For example, a wire connected to a clip can pull on the clip in the same direction as a flexible rod maintaining the stent in the desired position, or a wire connected to the clip can pull on the loop in the opposite direction as a wire maintaining the stent in the desired position.

Alternatively, the clip may include a ferromagnetic material, and a magnetic field can be used to displace the clip from the stent, while the stent is maintained at the desired position with, for example, a flexible rod or a wire. Alternatively, the stent may include a ferromagnetic material, the clip can be maintained at the desired position with, for example, a flexible rod or a wire, and a magnetic field may be used to displace the stent to a desired position from the clip. Alternatively, the clip may be constructed of a biodegradable material, so that after a predetermined amount of time, the clip degrades and the stent expands to its deployed form.

In another embodiment, a stent 30 may be maintained in a compacted form with glue that fastens two portions of the sheet to each other. When the stent is in its compacted form, the relative position of the adjacent layers can be maintained by the glue, so that the stent 30 is maintained in its compacted form and the spiral of the thin film metal sheet does not unravel. The glue can be constructed of a biodegradable material, so that after a predetermined amount of time, the glue degrades and the stent expands to its deployed form.

Thus, for example, a ring, loop, rivet, clip, or glue can be a self-contained constraining device. Other devices or features can serve as a self-contained constraining device for a stent. A self-contained constraining device can be a device that is a part of the stent, acts to maintain the stent in a compacted form, and then allows the stent to expand to its deployed form upon the passage of a predetermined period of time, upon exposure to a predetermined environmental condition, such as an environmental condition that exists within the body, and/or upon triggering by a stimulus having its origin outside of the body, such as a user controlled imposition or change of a magnetic field or application of a mechanical force. Two or more factors can be necessary for the self-contained constraining device to allow the stent to expand to its deployed form. For example, the self-contained constraining device may have the form of a clip made of a biodegradable material. The biodegradable material can be chosen or designed so that for the clip to allow the stent to expand to its deployed form, the clip must be within a blood vessel and exposed to blood and the clip must reside within the blood vessel for a sufficiently long period of time for the blood to dissolve enough of the clip material for the clip to release.

The term "biodegradable" as used herein to describe a material can mean a material that is chemically broken down by chemical or biochemical processes in the body. Alternatively, the term "biodegradable" can describe a material that is solubilized within the body. Alternatively, the term "biodegradable" can describe a material that, while exhibiting a predetermined strength at a temperature lower than body temperature, such as at room temperature, exhibits a lower predetermined strength at body temperature. Alternatively, the term "biodegradable" can describe a material that exhibits a predetermined structural integrity under a condition outside of the body, and exhibits a lesser predetermined structural integrity under a condition within the body.

In one embodiment, the stent 30 may be formed of a thin film sheet of shape memory alloy wrapped into a generally tubular shape. The stent, with its generally tubular shape, can be bent into an arc of more than 180 degrees having a radius of less than about 3 mm. When the force inducing the bending is released, the stent can recover its original shape. For example, the curvature, $1/r$, can be defined as the reciprocal of the radius of the arc, r. A stent having a generally tubular shape has a configuration initially like that of a cylinder. Because the axis of the cylinder is a straight line, its curvature is zero. The stent can be bent into an arc of radius $r_{bend}$, so that the curvature is $1/r_{bend}$. When the force inducing the bending is released, the stent can recover most of its original shape, so that its curvature is less than 5% of that when bent, i.e., is $0.1/r_{bend}$. For the purposes of this disclosure, when the curvature of the stent upon the release of the bending force is less than 5% of the curvature of the stent when bent, the stent is referred to as "recoverably bent".

For example, a stent 30 of the present invention having a generally tubular shape may be recoverably bent into an arc (e.g. as shown in FIG. 9 for stent 100) of at least about 180 degrees having a radius of less than about 3 mm. Ideally, the stent can be recoverably bent into an arc of at least about 180 degrees having a radius of less than about 1.5 mm.

The stent 30 may be passed through a portion of a blood vessel 10 having an arc of more than 180 degrees and a radius of less than about 3 mm and preferably less than about 1.5 mm.

The structure of the stent 30 in its compacted form can exert an outward directed, radial force. This outward directed, radial force can cause the stent to expand. For example, the outward directed, radial force of a 15 mm long stent in a 3 mm diameter artery may be configured to be larger than a drag force of 0.0015 Newtons. For the stent to deploy and anchor itself at the desired position, the radial force may be configured to range from about 0.01 Newtons to about 0.03 Newtons. For example, for stents used in studies, a 7 µm thick stent 15 mm long can produce a 0.016 Newton radial force in a 3 mm diameter artery, while a 15 µm thick stent can produce a 0.03 Newton radial force.

The structure of the stent 30 in its deployed form can exert an outward directed, radial force. When this outward directed, radial force is divided by the outer area of the thin film sheet forming the structure, a pressure is obtained. This outward directed pressure associated with the stent in its deployed form may be configured so that the stent is maintained at a given position in a body cavity, for example, in a blood vessel, without sliding, e.g., without blood flow causing the stent to slide. For example, the structure 30 in its deployed form exerts a pressure at an outer surface of the thin film sheet onto a body cavity, such as the wall of a blood vessel, of from about 70 Pascals to about 210 Pascals.

In an embodiment, the stent 30 is preferably configured to be bent into an arc without buckling. For example, when the stent is bent into an arc, blood can flow through the stent without being restrained from flowing through the stent. The stent has an internal area of passage. This is the area extending normal to the longitudinal direction bounded by the inner surface of the innermost layer of the sheet forming the stent. Thus, each point along the longitudinal direction has an associated internal area of passage. When the stent is bent into an arc, the minimum internal area of passage along the longitudinal direction can be less than about 80% of a circle having the second internal diameter associated with the deployed form of the structure of the stent before it is bent.

a. Experimental Results

1. Stress-Strain Testing

To characterize the stress-strain and shape memory properties of the thin film nitinol, an MTS Tytron (MTS, Eden Prairie, Minn.) was used. The MTS Tyron has a displacement resolution of 0.1 µm and a minimum force of 0.01 N. The film tested in this trial was removed from the wafer on which it was formed using a crack and peel method to produced a free-standing film. Tensile samples were fabricated using a razor blade and a strips of thin film nitinol with dimensions of 3 mm by 20 mm. The specimens were arranged in the grips such that the length of the specimen was 10 mm. All tests were conducted at room temperature. Prior to testing, a small load (0.01 lbs) was applied to eliminate slack in the test setup. The load on the thin film nitinol sample was ramped from 0.22 to 15.5 N (0.05 to 3.5 lbs) at a rate of 0.35 N/sec (0.08 lbs/sec). The load was then returned to 0.22 N and the film was heated to above the austenite finish temperature in order to record strain recovery.

A stress-strain curve quantifying the ductility and shape memory behavior of the thin film is shown in FIG. 21. The modulus of the film was calculated to be 17.8 GPa and the stress to induce twin boundary motion in the material was 136 MPa. The film withstood tensile forces above 425 MPa and was strained to above 5%. Upon unloading and heating, the thin film nitinol sample exhibited complete strain recovery showing excellent shape memory behavior.

2. Differential Scanning Calorimetry

A Shimadzu DSC-50 (Shimadzu, Kyoto, Japan) differential scanning calorimeter (DSC) was used to determine the transformation temperatures of the thin film nitinol formed for this study. The thin film nitinol had a composition of 50.02 atom % Ti. Thin film nitinol was mechanically removed from the wafer and a sample weighing 19 mg was cut from the freestanding film. The film was cut into small sections to reduce internal stresses that may develop in the film during DSC testing. The specimen was heated to 150° C. and then cooled to −20° C. at a constant rate of 10° C./min. Transformation temperatures were determined from the endothermic and exothermic peaks of the heating and cooling curves. The curves obtained from the differential scanning calorimetry testing are shown in FIG. 5. The start and finish transition temperatures of thin film nitinol for the martensite ($M_s$, $M_f$) and austenite ($A_s$, $A_f$) phases were determined from the exothermic and endothermic peaks of the cooling and heating curves.

3. Implanted Neurovascular Stent

A swine animal model was used for the testing of in vivo deployment of the thin film nitinol neurovascular stents. FIG. 22A shows an angiogram of swine cranial vasculature prior to thin film NiTi neurostent deployment. FIG. 22B shows an angiogram of swine cranial vasculature taken after deployment of thin film NiTi neurostent of the present invention in the swine vasculature.

4. Thin Film Stent Stability Experiments

FIGS. 23 and 24 illustrate experimental results of the stability of thin film stents of varying thicknesses and with or without supporting trusses.

By using a near equiatomic alloy target, a DC sputtering technique was used to produce thin films of NiTi with an austenite finish temperature well below body temperature. The films were deposited on a 4" silicon wafer covered with a 500 nm thick silicon oxide buffer layer to prevent diffusion of nickel-titanium atoms into the silicon (i.e., to prevent silicide formation) and reduce or eliminate adhesion of the thin film to the silicon substrate. Depositions were performed at a base pressure below $5\times10^{-8}$ Torr and Ar pressure of $1.5\times10^{-3}$ Torr. The deposition rate was 0.1 µm/min and several different thickness values were fabricated (i.e., t=6, 8, 10, and 12 µm thick). During deposition the target was heated and the substrate was translated in 80 mm lengths perpendicular to the sputtering direction to minimize compositional variations. Based on prior measurements, the compositional variations were expected to be less than 1 atomic % within a 3" diameter zone of the Si wafer. The deposited film was removed from the substrate and the stand alone film was crystallized at 500° C. for 120 minutes in a vacuum less than $10^{-7}$ Torr.

Following crystallization, the film was machined into rectangular sheets (t×15 mm×15 mm). Several approaches were used to roll the film into stents and to insert the microstent sheets into <3 Fr catheters (<0.69 mm inner diameter). In all cases, stents were rolled on 0.64 mm steel cylinders. After carefully rolling the film with the cylinder, the rolled thin film is inserted into the delivery catheter and the cylinder is removed. In vitro and in vivo studies utilized neuroform delivery catheters (Boston Scientific, Natick, Mass. 3 Fr). After loading the thin film stent into the tip of this catheter, it was guided into position over an 0.014' guidewire. Deployment is then accomplished by removing the guidewire and simply pushing the stent out of the catheter with a 0.6 mm OD "push wire".

For deployment in arteries larger than 4-5 mm in diameter, calculations showed that thin film nitinol microstent (e.g. film 30), without further support, may have insufficient forces to prevent migration (radial force is inversely proportional to the radius). To address this issue, larger diameter thin film sheets were created similar to sheet 180 shown in FIG. 15. These stents 180 provided a double-wrap design that would allow the film to wrap twice around the interior of the vessel.

In addition to the double-wrap design, microstents containing reinforced superelastic nitinol wire scaffoldings as shown in FIGS. 14A-C were used. Although three different skeletal structures were considered, only the "zigzag" structure 210 of FIG. 14B was tested in vivo.

The deployment force of the nitinol sheets was measured in a specialized test setup (not shown) on a vibration isolation table. A 5 mm lumen plastic tube was cut in half along its axis to simulate the vascular geometry. The half plastic tube was placed over a force measurement system ($1.0\times10^{-5}$N resolution) and a nitinol stent was deployed into the plastic tube to measure the stent's deployment force $F_{radial}$ (see Eq. (2).). Four different thickness stents (i.e., 6 µm, 8 µm, 10 µm, and 12 µm) were evaluated and each nitinol stent was tested five times.

A Harvard Apparatus pulsatile pump (Harvard Medical, Holliston, Mass.) was used to approximate flow in small arteries to allow for in vitro testing of stent delivery, deployment and stability. The flow loop was constructed with 5 mm ID PVC tubing and the systole/diastole ratio was set to 40:60. The stroke volume was incrementally increased from 10 cc to 30 cc per stroke (600 to 2400 cc/min) to allow for evaluation of the stent's resistance to migration with flow velocities from 0.5~2.0 m/s. Prior to animal testing, all stents were evaluated with multiple deployments in the pulsatile flow loop using the exact wires and delivery catheters.

In-vivo tests were conducted in accordance with a protocol approved by the UCLA Animal Research Committee. Two 25 kg Yorkshire swine were prepared and draped in the usual sterile fashion. General anesthesia was administered via an endotracheal tube inserted via the direct laryngoscopy. A 6 French Pinnacle 10 cm introducer sheath (Terumo Medical, Tokyo, Japan) was inserted in the right femoral artery over an 0.035 inch guidewire using the Seldinger technique. A 4 Fr Angled Glidecath (Terumo Medical) was used to access and image the target vessel. Initial angiograms were performed by hand injections of 10 mls of Ominipaque contrast (GE Healthcare). After injections, digitally subtracted roadmaps of the target vessel were constructed. An 0.014 inch exchange length (300 cm) Hi-Torque Wisper guidewire (Guidant, Calif.) was positioned across the target vessel through the 4 Fr Angeled Glidecath. After removing the Glidecath, the Wisper wire was used to guide the thin film stent microdelivery catheter to the desired cerebral or femoral arteries. A 3 French neurocatheter with a 0.60 mm diameter push rod was used to deliver the stent. During the procedure heart rate, respiration rate, blood pressure, and oxygen saturation were monitored. The catheterization and stent implantation were visualized a continuous x-ray angiogram system (Philips Medical Systems, Andover, Mass.). All angiograms were recorded in single plane at 30 frames per second. After the final implantation, three dimensional angiograms with endoviews were constructed of the stents.

FIG. 23 shows a plot of the experimental (data points) and theoretical results (Eq. (2), solid line) for radial force of different thickness nitinol stents 30, as compared to double-overlapped thin film stent 180 (FIG. 15) and nitinol stents with skeletal backbones (single-zigzag structure 210 (FIG. 14B) and dual-zigzag structure 220 (FIG. 14C). By quantifying the radial force of the various stent designs, these results describe the ability of each stent to resist migration. The four thin film nitinol stents 30 (i.e., thickness ranging from 6, 8, and 12 µm) exhibit radial forces of 0.0043N, 0.011 N, 0.0261 N, and 0.0427N, respectively. The theoretical predictions presented calculated from Equation 2 agrees relatively well with the experimental data. FIG. 23 also shows the force measurement results for a double-overlap design 180 (with 10 µm thick film) doubles the radial force of its comparable single wrap counterpart. The single-zigzag 210 and dual-zigzag 220 wire reinforced segments (i.e., note these measurements are without film 30 attached) produce radial forces of 0.031 and 0.070N respectively (dashed lines). These two structures when combined with a 10 µm thick film exhibit 0.0781 N and 0.0961N radial force respectively.

The thin film microstents 30 with a skeletal backbone (210, 220) produce radial forces 3~3.7 times larger than a 10 µm thin film stent by itself (i.e. without skeletal backbone). According to these results, the thin film stents 30 should have sufficient force to immobilize the stent in small vessels while the reinforced stents (with skeletal backbones) certainly have enough force to seat themselves in larger vessels.

FIG. 24 provides experimental and theoretical results for the different stents studied in a flow loop. The ordinate lists the stent while the abscissa is the flow velocity at which stent migration occurs in tube diameters of 5 mm. The thin film experimental results are represented by circular data points while theoretical predictions are diamonds. There is qualitative agreement between the experimental and theoretical data but quantitative agreement is weak. This is attributed to the friction coefficient used in the analysis misrepresents the actual friction coefficient of the plastic tube.

The 6 and 8 µm thick films are immobilized at 0.5 and 0.65 m/s velocities respectively; while the 10 and 12 µm thick films show approximately 1.0 and 1.2 m/s migration starting velocities. Thus, for typical body flows the 6~8 µm thick films should only be used for lower velocity region (less than 0.5 and 0.65 m/s) and 10~12 µm thick films can be used for arteries in which flow velocities are in the range of 0.5~1.0 m/s. The double coil stent 180, and dual zig-zag structure 220, single zig-zag structure 210, coil structure 200 (all with 1o µm thick film) showed increasing migration starting velocities from over 1.3 m/s to almost 20.0 m/s. The maximum velocity of each stent to be immobilized were calculated from Eq. (1) and presented as 0.15, 0.4, 0.87 and 1.43 m/s respectively. This theoretical result shows linear tendency of frictional force by increase of flow velocity. However, the slopes from theoretical calculation and experimental data are most likely different because the assumed frictional coefficient is different than the actual coefficient.

In-vivo deployment test was also performed to evaluate the reinforced stent design. The swine's right femoral artery was selected as the target vessel for placement of thin film single-zigzag reinforced stent 210. As the scaffold was adequate to provide fluoroscopic visualization, the Td marker was not needed for enhanced visualization. The stents were easily deployed in 6 seconds and thin film and wire structures were well placed in the artery. Angiograms demonstrated well positioned and deployed stents which were easily visualized. All stents were well apposed to the vascular wall in the desired location. No migration and unstable motion were observed during stent deployment.

Accordingly, it is contemplated that one embodiment of the invention comprises a kit of thin film stents 30 ranging in thickness (e.g. from 6 µm to 12 µm) that may be selected for various diameter vessels within the body of a patient. It is further contemplated that such kit may also include a series of lengths depending on the type of treatment or anatomy desired for treatment (e.g. wide neck aneurysm, etc.).

II. Biocompatible Surface Treatment

For many stents, thrombosis is an issue, especially in small diameter vessels. Thrombosis in either NiTi or ePTFE is primarily related to platelets/fibrinogens/proteins adsorbed on the surface. Platelet-induced thrombosis is a major factor dictating success of vascular device implantation.

In general, the surface characteristics of bulk and thin film NiTi are substantially different. Bulk NiTi has grain size approximately five times larger than thin film NiTi and surface roughness values approximately 60~100 times higher. These will significantly influence the hemocompatibility of the system in an unpredictable manner. While both bulk and thin film NiTi's surface have a titanium oxide layer, it is not fully understood if and what differences exist between the titanium dioxide ($TiO_2$) formed on them. The oxide layer is important for two reasons. First, it is relatively hydrophilic (i.e. wetting angle of 50-100 degrees) reducing platelet adhesion on the surface minimizing thorombogenic behavior. Second, the $TiO_2$ layer acts as a barrier preventing the release of toxic Ni into the blood stream.

Untreated, sputter deposited thin film NiTi has a surface roughness that is two orders of magnitude smoother than bulk nitinol (5 nm vs. 500 nm), there is an interest in examining the thrombogenicity of thin film NiTi compared to both bulk nitinol and other commercially available graft materials.

The present invention details a surface treatment for generating a hydroxylated surface layer that confers surface electronegativity as well as super hydrophilicity. This surface treatment mimics the properties of endothelial cells lining blood vessels, which have a net negative charge and are also hydrophilic, two properties that decrease the attachment of blood products (specifically platelets, which carry a net negative charge). Therefore, the super hydrophilic treated thin film NiTi of the present invention represents a non-thrombogenic material that is vastly superior to existing material systems used in the treatment of vascular diseases. This finding has been confirmed in platelet rich plasma studies, whole blood flow loops, and in vivo animal studies as described in this patent. In addition to reducing thrombosis the super hydrophilic treated thin film NiTi (S-TFN) of the present invention reduces the adhesion of bacteria to the surface of the structure.

The potential applications of S-TFN are numerous. Because TFN can be fabricated to 5 micron thicknesses or less, delivery catheters can be miniaturized because of its ultra low profile. This low profile is also important for the delivery of covered stents into smaller arteries. For example, small diameter arteries may be able to be treated with S-TFN covered stents without thrombotic complications. Unlike heparin, whose administration is associated with known morbidity and mortality, the S-TFN stent of the present invention is non-pharmacologic, with nitinol based medical devices having a safe history of human implantation. Furthermore, S-TFN covered stents of the present invention avoid the need for mandatory and in most cases lifelong antiplatelet therapy after device implantation.

FIG. 25 illustrates an exemplary treatment method 400 for generating a super hydrophilic thin film NiTi stent in accordance with the present invention. A thin film NiTi sheet (e.g. sheet 30 generated using the DC sputter deposition technique described above) is first pretreated according to steps 402, 404, and 406. In one embodiment shown in FIG. 26, a cleaning pretreatment dip 402 comprises sequentially dipping the film in acetone at 414, methanol at 416, and finally alcohol at 418 for 5 minutes. At step 404, the film is subsequently placed in a buffered oxide etchant (BOE: aqueous $NH_4$-HF etchant) to eliminate the native oxide layer. Next, the film undergoes passivation in a nitric acid ($HNO_3$) solution (e.g. 30%) for 40 min at step 406. It is appreciated that while the above steps may be optimal for pretreating the film, one or more of the above pretreatment steps may be modified or omitted. For example, the total pretreatment process may simply comprise the passivation step 406.

At step 408, the thin film NiTi is then surface treated using a hydrogen peroxide treatment which comprises placing the film in a concentration of hydrogen peroxide ($H_2O_2$) solution mixed with deionized water at a specified temperature for a specified period of time. It is appreciated that the ideal treatment (e.g. for creating a super hydrophilic surface) is a function of the concentration of $H_2O_2$, time, and temperature (e.g. $HPT_{d,f,g}$, where d=$H_2O_2$ concentration, e.g. 3-30%, f=temperature, e.g. 25° C. or 110° C., and g=time, e.g. 0.5~15 hrs). For example, a super hydrophilic surface may be achieved by immersion of thin film NiTi in a $H_2O_2$ concentration of 30% at 25° C. for 15 hours. It is appreciated that in an increased temperature, e.g. boiling at 110° C., and/or concentration percentage, may result in a super hydrophilic surface being achieved in less time.

At step 410, the film is then removed from the $H_2O_2$ solution, and then stored in a high humidity environment at step 412. Step 412 is configured to maintain the surface condition of the super hydrophilic surface generated from the treatment step 408 without decaying of hydrophilicity. In one embodiment, step 412 comprises fully immersing the film in a deionized water (DI) solution. Alternatively, the film may be contained in high humidity air (e.g. >90% humidity) via a humidifying element, humidor, or the like.

a. Surface Treatment Experiment

Thin film NiTi was fabricated by a DC sputter deposition technique using a near equiatomic NiTi alloy target under UHV (ultra-high vacuum) atmosphere. The base pressure of the sputter chamber was below $5 \times 10^{-8}$ Torr and the Ar pressure was $1.5 \times 10^{-3}$ Torr. A 4" silicon wafer was used as a substrate with a 5000 Å thick silicon dioxide layer. To minimize compositional variations, the wafer was translated in 80 mm lengths perpendicular to the heated NiTi target. Films (i.e., 6 µm thick) were fabricated with a deposition rate of 0.1 µm/min. Following deposition, the film was mechanically removed from the wafer and crystallized at 500° C. for 120 minutes in a vacuum less than $10^{-7}$ Torr. Following this, the film was cut into 10×10 mm square specimens.

The fundamental properties of the film were also measured. The transformation temperature of the NiTi film was measured in a Shimazdu DSC-50 using approximately 10 mg of the film. Specimens were heated to 100° C. and then cooled to −60° C. at a constant rate of 7° C./min. To study crystallinity of the films x-ray diffraction spectra of the films are obtained using x-ray diffractometer with Cu $K_a$ (1.54 A) radiation. Surface morphology was characterized with a 3D optical profiling system (Wyko NT3300, VEECO). The PSI (Phase Shifting Interferometry) mode was used to produce the interference light on the thin film NiTi surface. Resolution was set to full mode and the objective was set to 20 times magnification on a 231.5 µm×304.2 µm area.

Following fabrication, the film was dipped sequentially in acetone, methanol, and finally alcohol for 5 minutes. The films were subsequently placed in a buffered oxide etchant (BOE: aqueous $NH_4$-HF etchant) to eliminate the native oxide layer followed by passivation in a 30% nitric acid ($HNO_3$) for 40 min. Following the above, the thin film NiTi was surface treated using one of the following processes: UV irradiation, thermal treatments, and hydrogen peroxide treatments ($H_2O_2$). For this patent we focus on the results of the hydrogen peroxide treatments which consist of placing the film in different concentrations of hydrogen peroxide ($H_2O_2$) solution mixed with deionized water at either room or boiling temperatures for different time periods. ($HPT_{d,f,g}$, where d=$H_2O_2$ concentration, 3 or 30%, f=temperature, 25 or 110° C., and g=time, 0.5~15 hrs).

The hydrophilicity was determined by measuring the wetting angles produced by a water droplet on the film surface (i.e., surface facing the target and not the surface in contact with the $SiO_2$ wafer). Contact angle measurements were performed in ambient air condition (i.e., humidity 65% and temperature 22.5° C.) with a First Ten Angstroms system (Edmund Industrial Optics). A deionized water droplet of 1 ml was used and a total of three measurements were made for each reported data. Average values along with maximum and minimum values are reported. For all tests performed, the samples were stored in a high humidity environment prior to measurements.

An energy dispersive spectroscopy (EDX: CAMBRIDGE STEREOSCAN 250, Cambridge Instrument) was used for surface element analysis (20 kV, 138 picoA, 200 sec incident, 25 mm working distance). Also TEM studies were performed to evaluate the oxide layer produces before and following treatment.

To evaluate thrombogenicity platelet adhesion assays, whole blood studies and bacterial studies were performed. All of these demonstrated the lack of adhesion of blood products on the thin film Nitinol material. To further demonstrate the lack of thrombosis, in vivo swine tests were conducted. A description of these tests are provided below.

Expanded polytetrafluoroethylene (ePTFE) and Dacron samples were taken from unused commercially available endografts using sterile technique, and cut into 1 cm×1 cm pieces. Bulk, electro-polished, medical grade nitinol (gift of Johnson Matthey, Inc., London, England) was also cut into 1 cm×1 cm pieces for platelet studies. These samples were used as controls to compare the results of the treated thin film Nitinol of the present invention.

Platelet rich plasma (PRP) was prepared by centrifuging 45 cc of fresh whole blood from a healthy adult donor with 5 cc of a 3.8 wt % citrate solution at 400 g for 15 min. The prepared PRP contained $3-3.5 \times 10^7$ platelets/ml. 1 cm×1 cm samples (ePTFE, Dacron, bulk Nitinol, untreated U-TFN, or surface treated S-TFN) were placed in 24-well microplates, and incubated with 1.0 ml of PRP. After contacting the substrate for 30, 60, or 180 min, the PRP was removed and the samples were gently rinsed three times with phosphate buffered saline (PBS) to remove platelets that were non-specifically adsorbed to the surface. Samples were fixed with 2% glutaraldehyde and 1% osmic acid at 4° C. for 1 hr before undergoing serial dehydration with increasing concentrations of ethanol (50/50, 60/40, 75/25, 90/10, 95/5, 100/0) twice for 10 min each. After dehydration, the substrates were critical point dried overnight.

Samples were evaluated using scanning electron microscopy (SEM). The number of platelets per unit area was quantified by randomly selecting ten images (1 mm×1 mm) on the 1 cm×1 cm surface. The results were quantified as the mean±sem. The significance of the difference among these mean values was statistically evaluated by the Student's t-test and compared against that of super hydrophilic S-TFN.

An example device was also evaluated for thrombosis both in vivo and in vitro. A self expanding stent 20 mm long and 4 mm in diameter, self-expanding nitinol Neuroform stent (Boston Scientific, Natick, Mass.) was covered with the superhydrophillic thin film nitinol. This covered stent was collapsed and inserted into a 4 French Terumo glide catheter (Terumo Medical).

For in vitro tests, two coverings were evaluated, i.e. neuroform type stents covered with either ePTFE or STFN. All stent coverings were of equal surface area and were weighed prior to deployment. The stents were exposed to whole human blood for 3 hours at a WSR of 2200 s$^{-1}$. Coverings were subsequently weighed again and analyzed by scanning electron microscopy (SEM). Coverings not used for SEM were placed in a thrombolytic buffer at 37° C. for 30 minutes.

In-vivo testing was conducted in accordance with a protocol approved by the UCLA Animal Research Committee. An 18 kg Yorkshire swine was prepared, placed under general anesthesia and percutaneous vascular access was obtained via the Seldinger technique and fifty units per kilogram of heparin was administered before stent deployment. The prepared S-TFN covered stent was percutaneously implanted into the external iliac artery (3.5 mm in diameter) and the swine was survived for two weeks. Prior to and following deployment, angiograms were performed with machine injections of contrast solution via marker calibrated pigtail catheters. The pig was not anticoagulated post procedure. Repeat angiography was performed two weeks following the procedure under general anesthesia. The swine was then euthanized and the stent specimen was collected for scanning electron microscopy (SEM) and histopathologic analysis.

FIGS. 27A and 27B illustrate plots of DSC (FIG. 27A) and XRD (FIG. 27B) for the thin film NiTi used in this experiment. FIG. 27A shows one endothermic peak during heating corresponding to the transformation from martensite to austenite (austenite start temperature, $A_s$=22.09° C. and the austenite finish temperature, $A_f$=35.44° C.). The $A_f$ temperature is slightly below human body temperature. During cooling, two exothermic peaks are observed corresponding to the transformation from austenitic to intermediate rhombohedral phase, R-phase, and subsequently to the martensitic phase ($R_s$=16.37° C., $M_s$=$R_f$=−3.62° C. and $M_f$=−17.58° C.). FIG. 27A clearly demonstrates that both the $A_f$ and $A_s$ temperatures are in the range needed for heat activation of thin film NiTi devices in the vascular system as desired for a self-expanding configuration in accordance with the present invention.

FIG. 27B shows the XRD pattern of thin film NiTi measured at room temperature after it was heated above $A_f$. A strong peak corresponding to 2θ=42.5° is observed between 20° and 60° corresponding to the (110) peak of the B2 phase. There is an absence of any martensite peaks indicating a material fully austenite. All subsequent data reported on wetting angle measurements were made on films fully in the B2 phase.

FIG. 28A shows 3D contour plot along with a line plot (FIG. 28B) of surface morphology of the Nitinol thin film in the B2 phase. FIG. 28A shows an average surface roughness $R_a$ of approximately 5 nm for the surface contour. FIG. 28B provides more detail on the surface morphology showing peaks and valleys of 14 nm and −19 nm, respectively. This ultra flat surface reduces platelet adhesion and fibrinogen adsorption which are known to generate thromobosis during contact with blood.

FIG. 29 is a plot showing the contact angle produced by hydrogen peroxide treatment (HPT) as a function immersion time in the $H_2O_2$ solution treatment step. FIG. 29 shows that a super hydrophilic surface is achieved using a treatment of 30% $H_2O_2$ solution at room temperature (25° C.) for 15 hours. A super hydrophilic surface is herein defined as a surface having zero or near zero (e.g. less than 5 degrees) degree wetting angle.

It is important to note that these large reductions in wetting angle are not observed in bulk NiTi and this is an unexpected result. The surface treatment of NiTi with 30% H2O2 in a boiling aqueous solution in Chu et al. did not result in a superhydrophilic surface It should also be noted that the super hydrophilic response of the thin film NiTi surface treatment of the present invention does not result in any increased brittleness as is associated with thermal treatments.

Tests were also performed to study the effect of increase temperature of the solution, and decrease concentration of the solution. For example, treatment with a solution of 30% $H_2O_2$ at boiling temperature (110° C.) showed reduced contact angles at about 10~15°, which became saturated at 3 hours, and did not improve with increase of time (up to 6 hours). Thus HPT in boiling solution is not believed to provide desired super hydrophilic surface, possibly due to titanium oxide (TiO) removal at higher temperatures. Furthermore, it was found that treatment with a solution of 3% $H_2O_2$ at room temperature did not achieve lower than 10% contact angle after 3 hours.

Pretreatment processes among three pretreatments (i.e., cleaning pretreatment, native oxide layer removal, and passivation) showed that the passivating process using $HNO_3$ solution after removing native oxide layer on thin film NiTi showed the best results (zero or near zero contact angle).

FIGS. 30A and 30B are TEM results between thin film NiTi treated in accordance with the present invention (FIG. 30A), and untreated NiTi (FIG. 30B), which illustrate a clear difference in the oxide layer. As seen in FIG. 30A, the treated thin film Nitinol 320 has an oxide layer 322 of approximately 100 nm. As shown in FIG. 30B, the untreated NiTi 330 has an oxide layer approximately 5-10 nm (note that different scales are presented with a higher magnification of the untreated film). The PT layer's 324, 336 are present merely for generating the TEM image, and are not generally associated with the treatment process of the present invention.

Thus, the super hydrophilic response is an unexpected result of the process of the present invention as applied to thin-film nitinol 470 (shown in FIG. 35). The thin film nitinol 470 results in a significantly increased oxide layer 474 covering the NiTi film 472. Attached to the surface are an approximately 1 atomic thick layer of hydroxyl groups 476 attached to the oxide layer 474.

The wetting angle observed on the film NiTi material after being surface treated with the method of the present invention is substantially different than reported previously on any NiTi material. This large reduction in wetting angle is attributed to one or more of: the relative smoothness of the thin film NiTi 472, the significantly larger oxide layer 474 (and possible presence of TiO), and/or the presence of hydroxyl groups 476 on the surface of the film.

It is important to point out that the oxide surface at least for bulk nitinol is presumed to be $TiO_2$. However, SEM images of the thin film nitinol treated in accordance with the present invention, revealed a lattice structure consistent with an oxide layer that comprises primarily, if not entirely TiO. This is significant because TiO has more bonds available for bonding the OH groups when compared to $TiO_2$. It is believed that that the forming of the TiO layer in the thin film Nitinol of the present invention, as opposed to the $TiO_2$ layer present in bulk film NiTi processed according to Chu et al., is a result of the thin film Nitinol, the pre-treatment removal of the native $TiO_2$ layer and/or passivation, the lower temperature of the hydrogen peroxide treatment dip (e.g. room temperature vs. boiling temperature), or a combination of one or more of the above.

It is thus contemplated that the room-temperature or non-boiling temperature hydrogen peroxide treatment process, along with native oxide removal and passivation process of the present invention, may be used to generate a super hydrophilic surface on bulk nitinol or other material with a nitinol layer.

Storage of the film in a high humidity environment, as detailed above in treatment method 400, aids in preventing the release of the hydroxyl groups. While reducing the wetting angle, the hydroxyl groups bound to the surface are unstable and are easily be decomposed in ambient air environment. By storing the surface treated thin film in a high humidity environment (e.g. step 412), decay of super hydrophilicity is prevented. In one embodiment, step 412 comprises placing a fully saturated deionized (DI) water cloth in a vacuum bagged container along with the treated thin film. The thin film may be coiled inside a catheter for ready installation for a desired procedure. While the above preservation approach may be the most practical, it is contemplated that other preservation/hydration processes may also be employed.

Platelet adhesion studies were done to compare three specific samples, ePTFE, U-TFN, and the S-TFN of the present invention, to assess the time dependent differences measured after 30, 60, and 180 minutes of platelet contact.

FIGS. 31A-C illustrate scanning electron micrograph images demonstrating increasing platelet adhesion on ePTFE after 30 minutes (FIG. 31A), 60 minutes (FIG. 31B) and 180 minutes (FIG. 31C) of contact with platelet rich plasma.

FIGS. 32A-C illustrate scanning electron micrograph images demonstrating increasing platelet adhesion on Untreated Thin Film Nitinol after 30 minutes (FIG. 32A), 60 minutes (FIG. 32B) and 180 minutes (FIG. 32C) of contact with platelet rich plasma.

FIGS. 33A-C are scanning electron micrograph images of super hydrophilic thin film Nitinol of the present invention, demonstrating minimal platelet adhesion and no evidence of aggregation at 30 minutes (FIG. 33A), 60 minutes (FIG. 33B), and 180 minutes (FIG. 33C) after contact with platelet rich plasma.

While platelets adhered in a non-uniform manner, the SEM images demonstrated clear differences between these three materials with increasing platelet adhesion and aggregation over time noted in the ePTFE group (FIGS. 31A-C) and the U-TFN group (FIGS. 32 A-C). However, there were very few adherent platelets in the S-TFN group of the present invention and there was evidence that platelet aggregation did not occur at any time point for the S-TFN (FIGS. 33 A-C).

FIG. 34 is a graph of platelet adhesion per $mm^2$ of surface area for various surfaces after 180 minutes of contact with platelet rich plasma. Platelet adhesion and aggregation on Dacron (n=3), ePTFE (n=3), bulk nitinol (n=3), U-TFN (n=3), and S-TFN (n=5) were quantified using a 180 minute time point as a marker. The S-TFN of the present invention demonstrated a significant decrease in the number of adherent platelets (range 0-3 in all images evaluated) with a mean value of 1±0.5 platelets per $mm^2$. In contrast, the mean platelet adhesion on ePTFE (71±21 platelets per $mm^2$), Dacron (36±18 platelets per $mm^2$), bulk nitinol (41±17 platelets per $mm^2$) and U-TFN (34±17 platelets per $mm^2$) were all significantly higher compared to S-TFN ($p<0.05$). For ePTFE, there were many instances where the aggregated platelets were very dense with >100 platelets per $mm^2$.

Bacterial studies have also been conducted on the similar representative samples. It is known that bacterial adherence is most prominent in surfaces which are hydrophobic, positively charged, and relatively rough. FIG. 37 illustrates results of an S. Aureus adhesion study on treated thin film Nitinol as compared to ePTFE, Dacron, or untreated thin film Nitinol. It was shown that treated thin film Nitinol of the present invention is the least prevalent as compared to ePTFE, Dacron, or untreated thin film Nitinol.

Following the platelet rich plasma and bacterial adhesion studies, in vitro flow loop studies using covered stents and whole blood was evaluated for ePTFE and S-TFN. Average weight measuring the degree of thrombosis was measured for each sample. The net change in weight for S-TFN before and after exposure to the flow loop was 1.85 $mg/cm^2$±0.63, compared to ePTFE with 7.15 $mg/cm^2$±1.23 (n=4, $p<0.01$). ELISA assay for fibrin showed an average of 51.9 $\mu g/cm^2$±6.7 for S-TFN compared to 466.9 $\mu g/cm^2$±73.6 for ePTFE (n=5, $p<0.001$). Qualitative and quantitative measurements of S-TFN covered stents exposed to an in vitro flow loop at a WSR designed to simulate a moderate vascular stenosis show significantly less thrombosis compared to ePTFE covered stents.

To better quantify these results, in vivo studies were conducted. It should be noted that the in vivo studies conducted on untreated TFN all yielded thrombotic complications within the first hour following deployment and these results are not repeated here. A swine model was used to obtain histopathology on S-TFN in vivo. An S-TFN covered stent was placed in a 3.5 mm in diameter left external iliac artery with angiography confirming proper placement and patency at the time of the initial procedure. Repeat angiography was performed two weeks after placement. The S-TFN covered stent remained completely patent with good flow demonstrated on angiography of FIG. 36. Histopathology demonstrated endothelialization of the S-TFN without thrombus formation and without excessive neointimal hyperplasia. The vessel wall was also pristine without damage from the S-TFN covered stent.

From the above results, it is clear that the super hydrophilic surface treated TFN in accordance with the present invention significantly reduces platelet adhesion and aggregation. In our in vitro platelet assays, S-TFN demonstrated neither platelet adhesion nor aggregation over time, suggesting that as long as the super hydrophilic surface layer is intact, platelet adhesion will be prevented. Furthermore, when placed in a small diameter artery (3.5 mm), an S-TFN covered stent remained patent and rapidly endothelialized which is in sharp contrast to untreated TFN materials that typically thrombus within an hour of placement in this small of diameter artery.

As can be seen, therefore, the present invention includes the following inventive embodiments among others:

1. A vascular implant, comprising a sheet comprising thin film nickel titanium (NiTi), wherein the sheet comprises at least one super-hydrophilic surface.

2. An implant according to embodiment 1, wherein the super-hydrophilic surface has a water contact angle of less than approximately 5 degrees.

3. An implant according to embodiment 1, wherein the super-hydrophilic surface is configured to deter platelet adhesion at a rate of less than 3 parts per mm$^2$ when subjected to platelet rich plasma for 3 or more hours.

4. An implant according to embodiment 1, wherein the hydrophilic surface is fabricated by a method comprising the following: immersion of the thin film in a hydrogen peroxide solution.

5. An implant according to embodiment 4, wherein the method further comprises: passivation of the thin film in a nitric acid solution prior to immersion of the thin film in a hydrogen peroxide solution.

6. An implant according to embodiment 5, wherein the method further comprises: immersion of the thin film in a buffered oxide etchant to eliminate the native oxide layer prior to passivation of the thin film.

7. An implant according to embodiment 6, wherein the method further comprises: immersion of the thin film in a cleaning pretreatment dip comprising one or more of the following: acetone, methanol, and alcohol.

8. An implant according to embodiment 6, wherein the thin film is generated using DC sputter deposition.

9. An implant according to embodiment 1, wherein the thin film has a thickness of less than about 30 μm.

10. An implant according to embodiment 9: wherein the thin film comprises a stent configured to be installed adjacent a vascular aneurysm; and wherein the thin film has a thickness ranging between about 4 μm and about 12 μm.

11. An implant according to embodiment 10: wherein the implant comprises a stent configured to be installed adjacent a cerebral aneurysm; and wherein the thin film has a thickness ranging between about 6 μm and about 8 μm.

12. An implant according to embodiment 10, wherein the stent comprises: a generally rectangular thin film sheet wrapped into a generally tubular shape having a longitudinal and radial direction; wherein two distal edges of the sheet define two ends of the tubular shape; wherein two longitudinal edges of the sheet overlap; and wherein the sheet has a compacted form with a first internal diameter and a deployed form with a second internal diameter larger than the first internal diameter.

13. An implant according to embodiment 12: wherein the stent is configured to be delivered into a blood vessel in the compacted form; wherein the stent is configured to be expanded to its deployed form at a treatment location within the blood vessel; and wherein the stent is configured to expand onto an internal surface of the blood vessel and exert a radial force on said internal surface.

14. An implant according to embodiment 13: wherein the treatment location is an aneurysm; and wherein the stent is configured to deploy at the aneurysm to cover at least a portion of the aneurysm.

15. An implant according to embodiment 12: wherein the stent comprises a truss comprising one or more members configured to be disposed in a compressed form when constrained inside a catheter; wherein the truss is configured to automatically expand at the treatment site when not constrained inside said catheter; wherein the thin film sheet is disposed over the truss covers the truss in the compacted from; and wherein the thin film sheet is configured to expand with expansion of said truss.

16. A method for generating a super hydrophilic layer on the surface of a vascular implant, comprising: fabricating a sheet comprising thin film nickel titanium (NiTi); and immersing the thin film in a hydrogen peroxide solution to generate at least one hydrophilic surface on the thin film.

17. A method according to embodiment 16, wherein the hydrophilic surface comprises a super-hydrophilic surface having a water contact angle of less than approximately 5 degrees.

18. A method according to embodiment 17, wherein the super-hydrophilic surface is configured to deter platelet adhesion at a rate of less than 3 parts per mm$^2$ when subjected to platelet rich plasma for 3 or more hours.

19. A method according to embodiment 16, further comprising: passivating the thin film in a nitric acid solution prior to immersing the film in the hydrogen peroxide solution.

20. A method according to embodiment 19, further comprising: immersing the thin film in a buffered oxide etchant to eliminate the native oxide layer prior to passivation of the thin film.

21. A method according to embodiment 19, further comprising: immersing the thin film in a cleaning pretreatment dip comprising one or more of the following: acetone, methanol, and alcohol.

22. A method according to embodiment 16, wherein the thin film is fabricated using DC sputter deposition.

23. A method according to embodiment 16, wherein the thin film has a thickness of less than about 30 μm.

24. A method according to embodiment 23: wherein the thin film has a thickness ranging between about 4 μm and about 12 μm.

25. A method according to embodiment 24: wherein the thin film has a thickness ranging between about 6 μm and about 8 μm.

26. A method according to embodiment 16, further comprising: storing the thin film in a high-humidity environment to maintain the super-hydrophilic surface.

27. A method according to embodiment 26, wherein the environment comprises a container comprising deionized water.

28. A method of forming a hydrophilic thin film sheet of nickel titanium, comprising: generating a sheet of thin film nickel titanium; subjecting the sheet of thin film nickel titanium to a surface treatment to remove the native titanium dioxide layer; and generating a hydrophilic layer by immersion of the thin-film sheet in a concentration of $H_2O_2$.

30. A method according to embodiment 28, wherein the sheet is stored in a high-humidity environment prior delivery within the body.

31. A hydrophilic thin film sheet of nickel titanium prepared by the process comprising the steps of: generating a sheet of thin film nickel titanium; subjecting the sheet of thin film nickel titanium to a surface treatment to remove the native titanium dioxide layer; and generating a hydrophilic layer by immersion of the thin-film sheet in a concentration of $H_2O_2$.

32. A system for treating a vascular condition, comprising: a sheet comprising thin film nickel titanium (NiTi);

wherein the sheet comprises at least one super-hydrophilic surface; and means for storing the sheet in a high-humidity environment.

33. A system according to embodiment 32, wherein the super-hydrophilic surface has a water contact angle of less than approximately 5 degrees.

34. An implant according to embodiment 33, wherein the super-hydrophilic surface is configured to deter platelet adhesion at a rate of less than 3 parts per mm$^2$ when subjected to platelet rich plasma for 3 or more hours.

35. A system according to embodiment 33, wherein the super-hydrophilic surface is fabricated by a method comprising: immersion of the thin film in a hydrogen peroxide solution.

36. A system according to embodiment 33, wherein the thin film has a thickness of less than about 30 μm.

37. A system according to embodiment 36, wherein the thin film comprises a stent configured to be installed adjacent a vascular aneurysm; and wherein the thin film has a thickness ranging between about 4 μm and about 12 μm.

38. A system according to embodiment 37: wherein the implant comprises a stent configured to be installed adjacent a cerebral aneurysm; and wherein the thin film has a thickness ranging between about 6 μm and about 8 μm.

39. A system according to embodiment 37, wherein the stent comprises: a generally rectangular thin film sheet wrapped into a generally tubular shape having a longitudinal and radial direction; wherein two distal edges of the sheet define two ends of the tubular shape; wherein two longitudinal edges of the sheet overlap; and wherein the sheet has a compacted form with a first internal diameter and a deployed form with a second internal diameter larger than the first internal diameter.

40. A system according to embodiment 39, further comprising: a catheter configured to be delivered into a blood vessel; wherein the stent is configured to be delivered in the compacted form inside the catheter; wherein the stent is configured to be deployed out the catheter and expanded to its deployed form at a treatment location associated with the aneurysm; and wherein the stent is configured to expand onto an internal surface of the blood vessel and exert a radial force on said internal surface.

41. A system according to embodiment 32: wherein the means for storing the sheet in a high-humidity environment comprises a container configured to house the thin film and a humidifying element;

42. A system according to embodiment 41, further comprising: a catheter configured to be delivered into a blood vessel; wherein the container is configured to house the catheter with the stent installed in a compacted form inside said catheter.

43. A vascular implant, comprising: a sheet comprising thin film nickel titanium (NiTi); the sheet having a compacted form having a first internal diameter and a deployed form having a second internal diameter larger than the first internal diameter; wherein the sheet is configured to be delivered into a blood vessel in the compacted form: wherein the stent is configured to expanded to its deployed form at a treatment location within the blood vessel; and wherein the stent is configured to expand onto an internal surface of the blood vessel and exert a radial force on said internal surface.

44. An implant according to embodiment 43: wherein the sheet comprises a generally rectangular thin film sheet wrapped into a generally tubular shape having a longitudinal and radial direction; wherein two distal edges of the sheet define two ends of the tubular shape; and wherein two longitudinal edges of the sheet overlap in the compacted form; and wherein the sheet comprises at least one super-hydrophilic surface.

45. An implant according to embodiment 43, wherein the thin film is generated using DC sputter deposition.

46. An implant according to embodiment 43, wherein the thin film has a thickness of less than about 30 μm.

47. An implant according to embodiment 46: wherein the thin film comprises a stent configured to be installed at a treatment site associated with a vascular aneurysm; and wherein the thin film has a thickness ranging between about 4 μm and about 12 μm.

48. An implant according to embodiment 47: wherein the implant comprises a stent configured to be installed at a treatment site associated with a cerebral aneurysm; and wherein the thin film has a thickness ranging between about 6 μm and about 8 μm.

49. An implant according to embodiment 47: wherein the stent comprises a truss comprising one or more members configured to be disposed in a compressed form when constrained inside a catheter; wherein the truss is configured to automatically expand at the treatment site when not constrained inside said catheter; wherein the thin film sheet is disposed over the truss covers the truss in the compacted from; and wherein the thin film sheet is configured to expand with expansion of said truss.

50. An implant according to embodiment 48, wherein the sheet comprises at least one super-hydrophilic surface having a water contact angle of less than approximately 5 degrees.

51. An implant according to embodiment 50, wherein the super-hydrophilic surface is configured to deter platelet adhesion at a rate of less than 3 parts per mm$^2$ when subjected to platelet rich plasma for 3 or more hours.

52. An implant according to embodiment 50, wherein the hydrophilic surface is fabricated by a method comprising: immersion of the thin film in a hydrogen peroxide solution.

53. An implant according to embodiment 43, wherein the sheet is configured such that the radial force is larger than a drag force imparted on said sheet from blood flow on said internal surface.

54. A method for treating a vascular condition, comprising: wrapping a sheet comprising thin film nickel titanium (NiTi) into a generally tubular shape having a longitudinal and radial direction; the sheet having a compacted form having a first internal diameter and a deployed form having a second internal diameter larger than the first internal diameter; installing the sheet in the compacted form into a catheter; and delivering the catheter to a treatment location inside the blood vessel; wherein the sheet is configured to be deployed out of the catheter and expanded to its deployed form at the treatment location; and wherein the sheet is configured to expand onto an internal surface of the blood vessel and exert a radial force on said internal surface.

55. A method according to embodiment 54, wherein the radial force is larger than a drag force imparted on said sheet from blood flow on said internal surface.

56. A method according to embodiment 55: wherein the thin film comprises a stent configured to be installed adjacent a vascular aneurysm; and wherein the thin film has a thickness ranging between about 4 μm and about 12 μm.

57. A method according to embodiment 56: wherein the implant comprises a stent configured to be installed adjacent a cerebral aneurysm; and wherein the thin film has a thickness ranging between about 6 μm and about 8 μm.

58. A method according to embodiment 56: wherein the sheet comprises at least one super-hydrophilic surface; and wherein the super-hydrophilic surface has a water contact angle of less than approximately 5 degrees.

59. An implant according to embodiment 4, wherein immersion of the thin film in a hydrogen peroxide solution is performed at a temperature below boiling temperature.

60. A method according to embodiment 16, wherein immersion of the thin film in a hydrogen peroxide solution is performed at a temperature below boiling temperature.

61. A system according to embodiment 35, wherein immersion of the thin film in a hydrogen peroxide solution is performed at a temperature below boiling temperature.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A vascular implant, comprising:
a thin film of nickel titanium (NiTi);
a non-native titanium monoxide (TiO) layer on the thin film of nickel titanium; and
a super-hydrophilic surface comprising a plurality of hydroxyl groups bonded to the non-native titanium monoxide layer.

2. The implant of claim 1, wherein the super-hydrophilic surface has a water contact angle of less than approximately 5 degrees.

3. The implant of claim 1, wherein the super-hydrophilic surface is configured to deter platelet adhesion at a rate of less than 3 parts per $mm^2$ when subjected to platelet rich plasma for 3 or more hours.

4. The implant of claim 1, wherein the thin film has a winding number greater than one.

5. The implant of claim 1, wherein the thin film has a winding number less than one.

6. The implant of claim 1, wherein the thin film is non-perforated.

7. The implant of claim 1, wherein the thin film comprises a plurality of sections, and wherein at least one section of the plurality of sections has properties distinct from at least one other section of the plurality of sections.

8. The implant of claim 7, wherein a first section of the plurality of sections is perforated and a second section of the plurality of sections is non-perforated.

9. The implant of claim 1, wherein the thin film has a tab-and-slot configuration.

10. The implant of claim 1:
wherein the vascular implant comprises a stent configured to be installed adjacent a vascular aneurysm; and
wherein the vascular implant has a thickness ranging between about 2 μm and about 12 μm.

11. The implant of claim 1:
wherein the vascular implant comprises a stent configured to be installed adjacent a cerebral aneurysm; and
wherein the vascular implant has a thickness ranging between about 4 μm and about 8 μm.

12. The implant of claim 10:
wherein the stent comprises a truss comprising one or more members configured to be disposed in a compressed form when constrained inside a catheter;
wherein the truss is configured to automatically expand at a treatment site when not constrained inside said catheter;
wherein the thin film is disposed over the truss covers the truss in the compacted from; and
wherein the thin film is configured to expand with expansion of said truss.

13. The implant of claim 10, wherein the stent comprises:
a generally rectangular thin film sheet wrapped into a generally tubular shape having a longitudinal and radial direction;
wherein two distal edges of the sheet define two ends of the tubular shape;
wherein two longitudinal edges of the sheet overlap; and
wherein the sheet has a compacted form with a first internal diameter and a deployed form with a second internal diameter larger than the first internal diameter.

14. The implant of claim 13:
wherein the stent is configured to be delivered into a blood vessel in the compacted form;
wherein the stent is configured to be expanded to its deployed form at a treatment location within the blood vessel; and
wherein the stent is configured to expand onto an internal surface of the blood vessel and exert a radial force on said internal surface.

15. The implant of claim 1, wherein the implant consists essentially of the thin film, the super-hydrophilic surface, and titanium monoxide layer.

16. The implant of claim 1, further comprising a self-contained constraining device.

17. The implant of claim 1, wherein the non-native titanium monoxide layer is approximately 100 nm thick.

18. A method for generating a super-hydrophilic surface of a vascular implant, comprising:
fabricating a thin film of nickel titanium (NiTi), wherein the thin film includes a native oxide layer of titanium dioxide;
removing the native oxide layer using a buffered oxide etchant; and
after removing the native oxide layer, generating a titanium monoxide (TiO) layer bonded to a plurality of hydroxyl groups by immersing the thin film in a hydrogen peroxide solution.

19. The method of claim 18, wherein the super-hydrophilic surface has a water contact angle of less than approximately 5 degrees.

20. The method of claim 19, wherein the super-hydrophilic surface is configured to deter platelet adhesion at a rate of less than 3 parts per $mm^2$ when subjected to platelet rich plasma for 3 or more hours.

21. The method of claim 18, further comprising:
passivating the thin film in a nitric acid solution prior to the immersing of the film in the hydrogen peroxide solution.

22. The method of claim 21, further comprising:
immersing the thin film in a cleaning pretreatment dip comprising one or more of the following:
acetone, methanol, and alcohol.

23. The method of claim 18, wherein the buffered oxide etchant comprises an aqueous $NH_4$-HF etchant.

24. The method of claim 18, wherein the thin film is fabricated using DC sputter deposition.

25. The method of claim 18, wherein the thin film has a thickness of less than about 30 μm.

26. The method of claim 25:
wherein the thin film has a thickness ranging between about 2 μm and about 12 μm.

27. The method of claim 26:
wherein the thin film has a thickness ranging between about 4 μm and about 8 μm.

28. The method of claim 18, further comprising:
storing the thin film in a high-humidity environment to maintain the super-hydrophilic surface.

29. The method of claim 28, wherein the environment comprises a container comprising deionized water.

30. The method of claim 18, wherein immersion of the thin film in a hydrogen peroxide solution is performed at a temperature below boiling temperature.

31. A method of forming a hydrophilic thin film sheet of nickel titanium, comprising:
obtaining a thin film of nickel titanium, the thin film having a native titanium dioxide layer;
removing the native titanium dioxide layer by applying a surface treatment to the thin film of nickel titanium; and
generating a titanium monoxide (TiO) layer having a super-hydrophilic surface by immersing the thin-film sheet in a concentration of hydrogen peroxide ($H_2O_2$).

32. The method of claim 31, wherein the thin film is stored in a high-humidity environment prior to delivery within a body.

33. A system for treating a vascular condition, comprising:
a vascular implant, comprising:
a thin film of nickel titanium (NiTi);
a titanium monoxide (TiO) layer on the thin film of nickel titanium; and
a super-hydrophilic surface comprising a plurality of hydroxyl groups bonded to the titanium monoxide layer; and
a storage container for the vascular implant, the storage container configured to maintain a high-humidity environment for the vascular implant.

34. The system of claim 33, wherein the super-hydrophilic surface has a water contact angle of less than approximately 5 degrees.

35. The system of claim 33, wherein the super-hydrophilic surface is configured to deter platelet adhesion at a rate of less than 3 parts per $mm^2$ when subjected to platelet rich plasma for 3 or more hours.

36. The system of claim 33, wherein the super-hydrophilic surface is fabricated by immersion of the thin film in a hydrogen peroxide solution.

37. The system of claim 33, wherein the thin film has a thickness of less than about 30 μm.

38. The system of claim 37,
wherein the thin film comprises a stent configured to be installed adjacent a vascular aneurysm; and
wherein the thin film has a thickness ranging between about 2 μm and about 12 μm.

39. The system of claim 38:
wherein the stent is configured to be installed adjacent a cerebral aneurysm; and
wherein the thin film has a thickness ranging between about 4 μm and about 8 μm.

40. The system of claim 38, wherein the stent comprises:
a generally rectangular thin film sheet wrapped into a generally tubular shape having a longitudinal and radial direction;
wherein two distal edges of the sheet define two ends of the tubular shape;
wherein two longitudinal edges of the sheet overlap; and
wherein the sheet has a compacted form with a first internal diameter and a deployed form with a second internal diameter larger than the first internal diameter.

41. The system of claim 40, further comprising:
a catheter configured to be delivered into a blood vessel;
wherein the stent is configured to be delivered in the compacted form inside the catheter;
wherein the stent is configured to be deployed out the catheter and expanded to its deployed form at a treatment location associated with the aneurysm; and
wherein the stent is configured to expand onto an internal surface of the blood vessel and exert a radial force on said internal surface.

42. The system of claim 33:
wherein the storage container comprises a container configured to house the thin film and a humidifying element.

43. The system of claim 42, further comprising:
a catheter configured to be delivered into a blood vessel;
wherein the container is configured to house the catheter with the stent installed in a compacted form inside said catheter.

44. A vascular implant, comprising:
a thin film of nickel titanium (NiTi) having a compacted form with a first internal diameter and a deployed form with a second internal diameter larger than the first internal diameter, wherein a native oxide layer of titanium dioxide has been removed from the thin film of nickel titanium; and
a non-native titanium monoxide (TiO) layer on the thin film of nickel titanium, the non-native titanium monoxide layer having a super-hydrophilic surface;
wherein the implant is configured to be delivered into a blood vessel in the compacted form;
wherein the implant is configured to expand to its deployed form at a treatment location within the blood vessel; and
wherein the implant is configured to expand onto an internal surface of the blood vessel and exert a radial force on said internal surface.

45. The implant of claim 44:
wherein the thin film comprises a generally rectangular thin film sheet wrapped into a generally tubular shape having a longitudinal and radial direction;
wherein two distal edges of the sheet define two ends of the tubular shape;
wherein two longitudinal edges of the sheet overlap in the compacted form; and
wherein the sheet comprises at least one super-hydrophilic surface.

46. The implant of claim 44, wherein the implant further comprises one or more radio-opaque markers.

47. The implant of claim 44, wherein the thin film comprises a phase transforming thin film.

48. The implant of claim 44:
wherein the vascular implant comprises a stent configured to be installed at a treatment site associated with a vascular aneurysm; and
wherein the vascular implant has a thickness ranging between about 4 μm and about 12 μm.

49. The implant of claim 48:
wherein the stent comprises a truss comprising one or more members configured to be disposed in a compressed form when constrained inside a catheter;
wherein the truss is configured to automatically expand at the treatment site when not constrained inside said catheter;
wherein the thin film is disposed over the truss covers the truss in the compacted from; and
wherein the thin film is configured to expand with expansion of said truss.

50. The implant of claim 44:
wherein the vascular implant comprises a stent configured to be installed at a treatment site associated with a cerebral aneurysm; and
wherein the vascular implant has a thickness ranging between about 4 μm and about 8 μm.

51. The implant of claim 50, wherein the super-hydrophilic surface has a water contact angle of less than approximately 5 degrees.

52. The implant of claim 51, wherein the super-hydrophilic surface is configured to deter platelet adhesion at a rate of less than 3 parts per mm² when subjected to platelet rich plasma for 3 or more hours.

53. The implant of claim 51, wherein the non-native titanium monoxide layer is approximately 100 nm thick.

54. The implant of claim 44, wherein the implant is configured such that the radial force is larger than a drag force imparted on said implant from blood flow on said internal surface.

55. A method for treating a vascular condition, comprising:
wrapping a sheet comprising thin film nickel titanium (NiTi) and a non-native titanium monoxide layer into a generally tubular shape having a longitudinal and radial direction, wherein the titanium monoxide layer comprises titanium monoxide bonded to a plurality of hydroxyl groups to form a super-hydrophilic surface;
the sheet having a compacted form having a first internal diameter and a deployed form having a second internal diameter larger than the first internal diameter;
installing the sheet in the compacted form into a catheter; and
delivering the catheter to a treatment location inside a blood vessel;
wherein the sheet is configured to be deployed out of the catheter and expanded to its deployed form at the treatment location; and
wherein the sheet is configured to expand onto an internal surface of the blood vessel and exert a radial force on said internal surface.

56. The method of claim 55, wherein the radial force is larger than a drag force imparted on said sheet from blood flow on said internal surface.

57. The method of claim 56:
wherein the thin film comprises a stent configured to be installed adjacent a vascular aneurysm; and
wherein the thin film has a thickness ranging between about 4 μm and about 12 μm.

58. The method of claim 57:
wherein the stent is configured to be installed adjacent a cerebral aneurysm; and
wherein the thin film has a thickness ranging between about 4 μm and about 8 μm.

59. The method of claim 57, wherein the super-hydrophilic surface has a water contact angle of less than approximately 5 degrees.

* * * * *

UNITED STATES PATENT AND TRADEMARK OFFICE
CERTIFICATE OF CORRECTION

PATENT NO. : 9,833,309 B2  
APPLICATION NO. : 13/224103  
DATED : December 5, 2017  
INVENTOR(S) : Levi et al.

Page 1 of 1

It is certified that error appears in the above-identified patent and that said Letters Patent is hereby corrected as shown below:

In the Claims

Claim 12, Column 40, Line 19, please delete "compacted from" and insert --compacted form--;

Claim 49, Column 43, Line 17, please delete "compacted from" and insert --compacted form--.

Signed and Sealed this
Sixth Day of February, 2018

Joseph Matal
*Performing the Functions and Duties of the*
*Under Secretary of Commerce for Intellectual Property and*
*Director of the United States Patent and Trademark Office*